(12) United States Patent
Koh et al.

(10) Patent No.: US 7,550,505 B2
(45) Date of Patent: Jun. 23, 2009

(54) PAN-ANTAGONISTS FOR THE ANDROGEN RECEPTOR AND ANDROGEN RECEPTOR MUTANTS ASSOCIATED WITH ANTI-ANDROGEN WITHDRAWAL

(75) Inventors: John Tze-tzun Koh, West Grove, PA (US); Paula Lynn McGinley, Langhorne, PA (US); Hongmu Pan, Newark, DE (US)

(73) Assignee: University of Delaware, Newark, DE (US)

( * ) Notice: Subject to any disclaimer, the term of this patent is extended or adjusted under 35 U.S.C. 154(b) by 0 days.

(21) Appl. No.: 11/880,725

(22) Filed: Jul. 24, 2007

(65) Prior Publication Data

US 2008/0064757 A1 Mar. 13, 2008

Related U.S. Application Data

(60) Provisional application No. 60/832,897, filed on Jul. 24, 2006.

(51) Int. Cl.
*C07C 317/32* (2006.01)
*A61K 31/277* (2006.01)

(52) U.S. Cl. ................................ 514/522; 558/413
(58) Field of Classification Search .................... None
See application file for complete search history.

(56) References Cited

U.S. PATENT DOCUMENTS

| 4,636,505 A | 1/1987 | Tucker |
| 5,872,150 A * | 2/1999 | Elbrecht et al. ............. 514/563 |
| 6,071,957 A * | 6/2000 | Miller et al. ................. 514/522 |
| 7,057,048 B2 | 6/2006 | Du et al. |

OTHER PUBLICATIONS

Murata, M. et al., "A General And Efficient Method For The Palladium-Catalyzed . . .", Tetrahedron, 60 (2004), pp. 7397-7403.
Zheng, N. et al., "Palladium-Catalyzed Synthesis Of Aryl Sulfides . . .", J. Org. Chem. 1998, 63, pp. 9606-9607.
Chen, B. et al., "Nucleophilic Aromatic Substituion Of Methacrylamide Anion . . .", J. Org. Chem. 2003, 68, pp. 10181-10182.
Tucker, H. et al., "Nonsteroidal Antiandrogens, Synthesis And Structure . . .", J. Med. Chem. 1998, 31, pp. 954-959.
Friden, PM et al., "Blood-Brain Barrier Penetration And In Vivo Activity Of An NGF . . .", Science, vol. 259, Issue 5093, pp. 373-377.
Davis, FF et al., "Enzyme-Polyethylene Glycol Adducts . . .", Enzyme Engineering, vol. 4, pp. 169-173.
Burnham, NL, "Polymers For Delivering Peptides And Proteins", Amer. J. Health-System Pharmacy, 1994, 51 (2), pp. 210-218.
Amselem, S. et al., "In Vitro Tests To Predict In Vivo Performance . . .", Chemistry And Physics Of Lipids, 64 (1993), pp. 219-237.
Hara, T. et al., "Novel Mutations Of Androgen Receptor . . .", Cancer Research, 63 (2003), pp. 149-153.
McGinley, P.et al., Circumventing Anti-Androgen Resistance by Molecular Design. J. Am. Chem. Soc. 129, 3822-3823, 2007.

* cited by examiner

*Primary Examiner*—Fiona T Powers
(74) *Attorney, Agent, or Firm*—Potter Anderson & Corroon, LLP

(57) ABSTRACT

Disclosed herein are novel antagonists of the androgen receptor and androgen receptor mutations associated with clinical failure of currently prescribed anti-androgens and use of said antagonists in the treatment of conditions associated with inappropriate activation of the androgen receptor.

6 Claims, 65 Drawing Sheets

PAN-ANTAGONISTS FOR THE ANDROGEN RECEPTOR AND ANDROGEN RECEPTOR MUTANTS ASSOCIATED WITH ANTI-ANDROGEN WITHDRAWAL

CROSS-REFERENCE TO RELATED APPLICATION

This application claims priority from U.S. Provisional Application Ser. No. 60/832,897, filed Jul. 24, 2006, which is incorporated by reference herein in its entirety.

GOVERNMENT INTERESTS

This invention was made with government support under Grant No. R01 DK054257-08A1 awarded by the National Institutes of Health. The government has certain rights in this invention.

FIELD OF THE INVENTION

Disclosed herein are novel antagonists of the androgen receptor and mutant forms of the androgen receptor associated with clinical failure of currently prescribed anti-androgens.

BACKGROUND OF THE INVENTION

Thirty to forty percent of prostate cancer patients become androgen independent (resistant to anti-androgen treatment) within five years. In many instances, androgen receptor mutations in androgen-independent prostate cancer cells cause anti-androgens to act as agonists or change receptor specificity. In these cases, alternative treatment regimes are needed. Exemplary treatments can be found in U.S. Pat. No. 4,636,505, which discloses acylanilides that have anti-androgenic properties, and U.S. Pat. No. 7,057,048, which discloses 6-sulfonamido-quinolin-2-one and 6-sulfonamido-2-oxo-chromene derivatives and their use as androgen antagonists.

Androgen receptor mutations are found in as many as 50% of metastatic, hormone refractory prostate cancer tumors. Studies suggest that 12-24% of hormone refractory tumors treated with flutamide contain the same T877A mutation.

Applicants herein disclose anti-androgens that are uniquely designed to target mutant forms of the androgen receptor that are known to impart resistance to known anti-androgens used in cancer chemotherapy. As such, these novel anti-androgens are believed to have the potential to delay the occurrence of anti-androgen resistance/anti-androgen withdrawal syndrome and to serve as a second line of defense in anti-androgen therapy when mutations to the androgen receptor give rise to anti-androgen withdrawal.

SUMMARY OF THE INVENTION

One aspect relates to a compound of the formula:

(I)

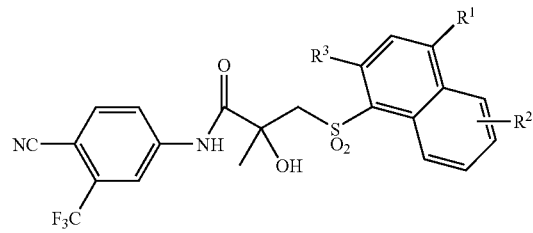

wherein $R^1$ is hydrogen, fluorine, chlorine, bromine, cyano, hydroxy, methyl acrylate, or $C_1$-$C_6$ alkyl optionally substituted with hydroxy; $R^2$ is hydrogen, hydroxy, fluoro, chloro, cyano, $C_1$-$C_5$ alkanoate, $C_1$-$C_5$ alkylamino, or $C_1$-$C_6$ alkyl optionally substituted with hydroxy or acrylate; and $R^3$ is hydrogen, $C_1$-$C_6$ alkyl, fluoro, chloro, bromo, or cyano.

Another aspect relates to a compound of the formula:

(II)

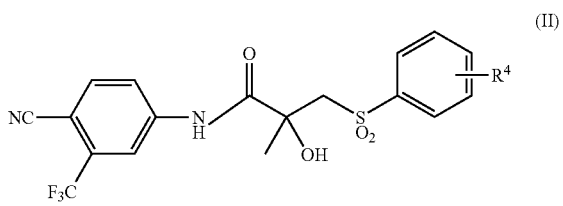

wherein $R^4$ is phenyl optionally substituted with hydroxy; $C_1$-$C_6$ phenylalkyl; $C_1$-$C_8$ alkoxy; or benzyl optionally substituted with hydroxy, $C_1$-$C_6$ alkoxy optionally substituted with methoxy or cyano, $C_1$-$C_6$ alkyl, $C_1$-$C_5$ alkanoate, or $C_1$-$C_5$ alkylamine.

A further aspect is for a method for the treatment of a mammal suffering from an androgen-dependent disorder comprising administering to the mammal in need thereof a therapeutically effective amount of a compound of Formula (I) or (II).

An additional aspect relates to a method for the treatment of a mammal suffering from an androgen-dependent disorder comprising administering to the mammal in need thereof a therapeutically effective amount of a compound of Formula (III), (IV), (V), (VI), (VII), (VIII), (IX), (X), (XI), (XII), (XIII), (XIV), (XV), (XVI), (XVII), (XVIII), (XIX), (XX), (XXI), (XXII), (XXIII), (XXIV), (XXV) or a combination thereof.

A further aspect is for a method for monitoring the effectiveness of treatment of a subject with a compound of Formula (I) or (II) comprising the steps of (i) obtaining a pre-administration sample from a subject prior to administration of the compound; (ii) detecting the level of androgen receptor activity in the pre-administration sample; (iii) obtaining one or more post-administration samples from the subject; (iv) detecting the level of androgen receptor activity in the post-administration samples; comparing the level of androgen receptor activity in the pre-administration sample with the post administration sample or samples; and altering the administration of the compound to the subject accordingly.

Another aspect is for a method for monitoring the effectiveness of treatment of a subject with a compound of Formula (III), (IV), (V), (VI), (VII), (VIII), (IX), (X), (XI), (XII), (XIII), (XIV), (XV), (XVI), (XVII), (XVIII), (XIX), (XX), (XXI), (XXII), (XXIII), (XXIV), (XXV) or a combination thereof comprising the steps of (i) obtaining a pre-administration sample from a subject prior to administration of the compound; (ii) detecting the level of androgen receptor activity in the pre-administration sample; (iii) obtaining one or more post-administration samples from the subject; (iv) detecting the level of androgen receptor activity in the post-administration samples; (v) comparing the level of androgen receptor activity in the pre-administration sample with the post administration sample or samples; and (vi) altering the administration of the compound to the subject accordingly.

Other objects and advantages will become apparent to those skilled in the art upon reference to the detailed description that hereinafter follows.

DETAILED DESCRIPTION OF THE INVENTION

Figure 1:
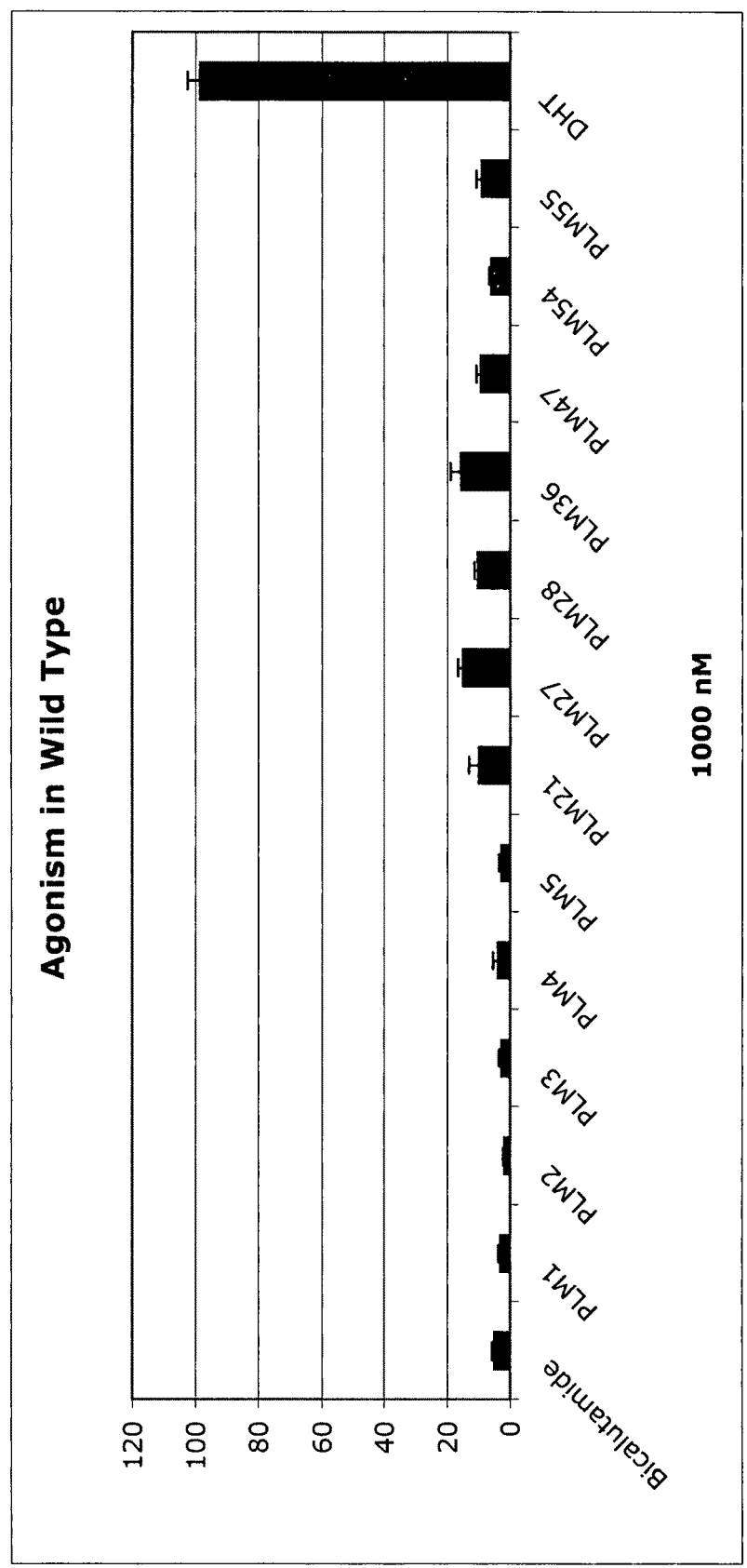
FIG. 1. Cellular transcriptional activity with AR(wild-type). RLU: relative light units of luciferase reporter gene wherein maximal activity of AR(wild-type) with dihydrotestosterone (DHT) is assigned a value of 100.
Figure 2:
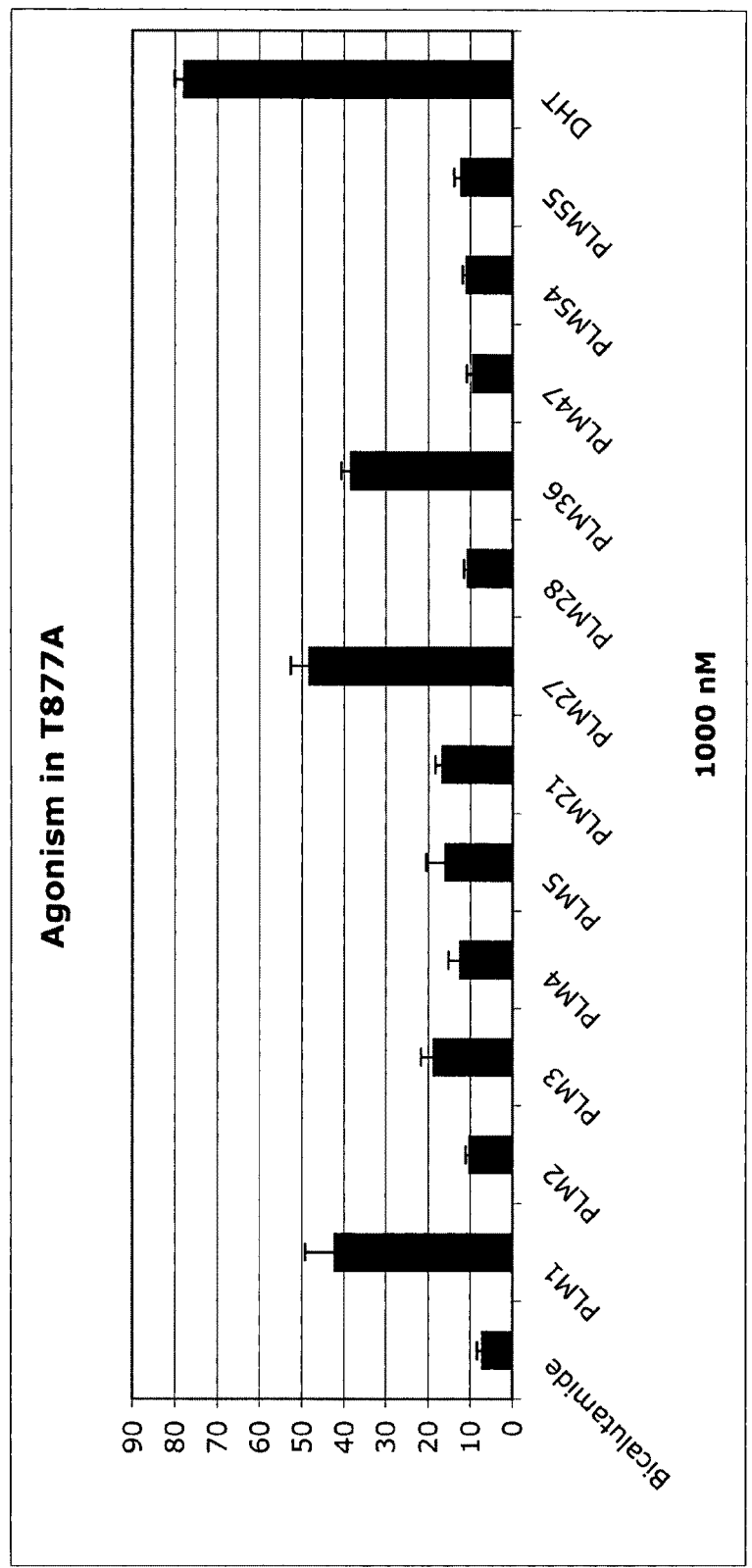
FIG. 2. Cellular transcriptional activity with mutant androgen receptor, AR(T877A). RLU: relative light units of luciferase reporter gene wherein maximal activity of AR(wild-type) with DHT is assigned a value of 100.
Figure 3:
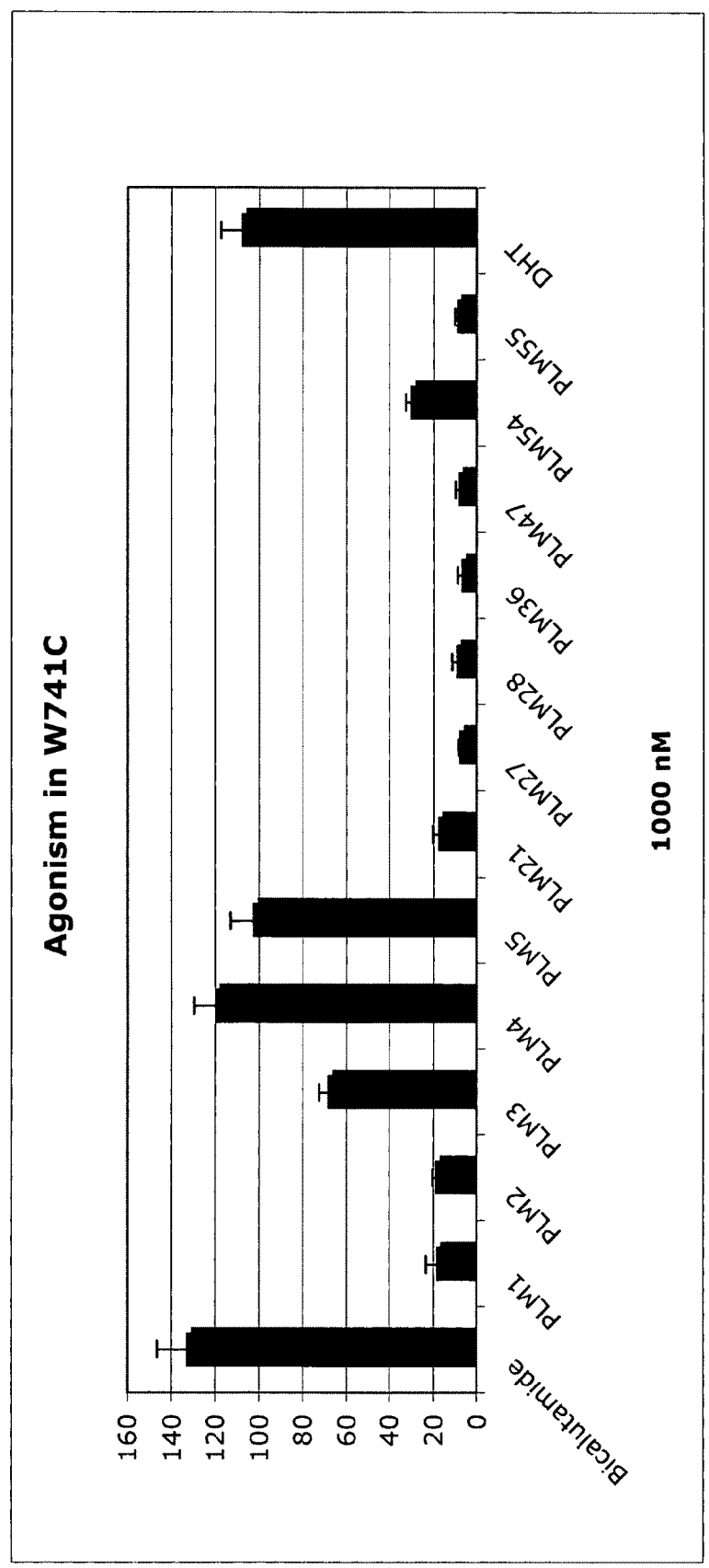
FIG. 3. Cellular transcriptional activity with mutant androgen receptor, AR(W741C). RLU: relative light units of luciferase reporter gene wherein maximal activity of AR(wild-type) with DHT is assigned a value of 100.
Figure 4:
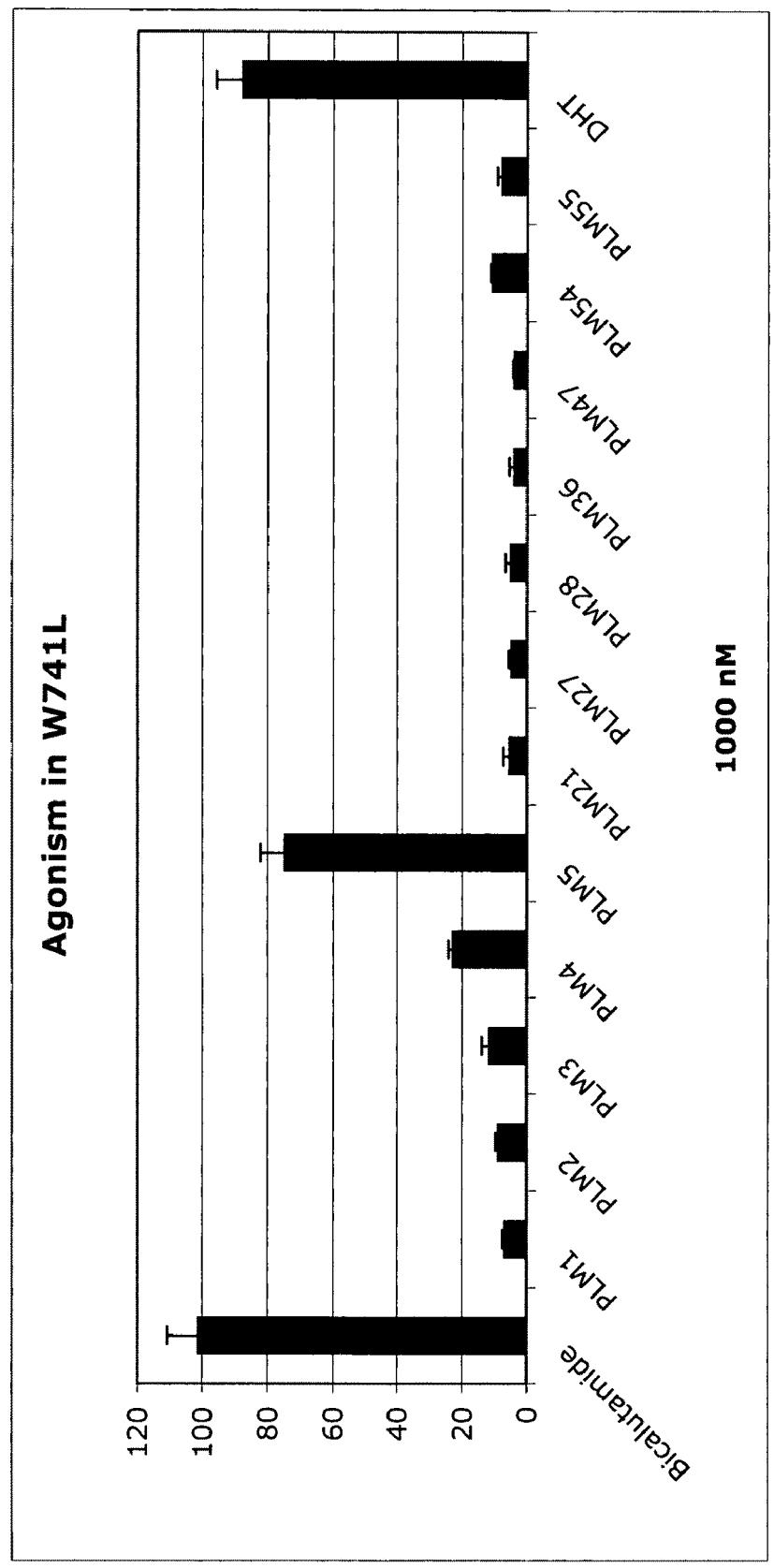
FIG. 4. Cellular transcriptional activity with mutant androgen receptor, AR(W741 L). RLU: relative light units of luciferase reporter gene wherein maximal activity of AR(wild-type) with DHT is assigned a value of 100.
Figure 5:
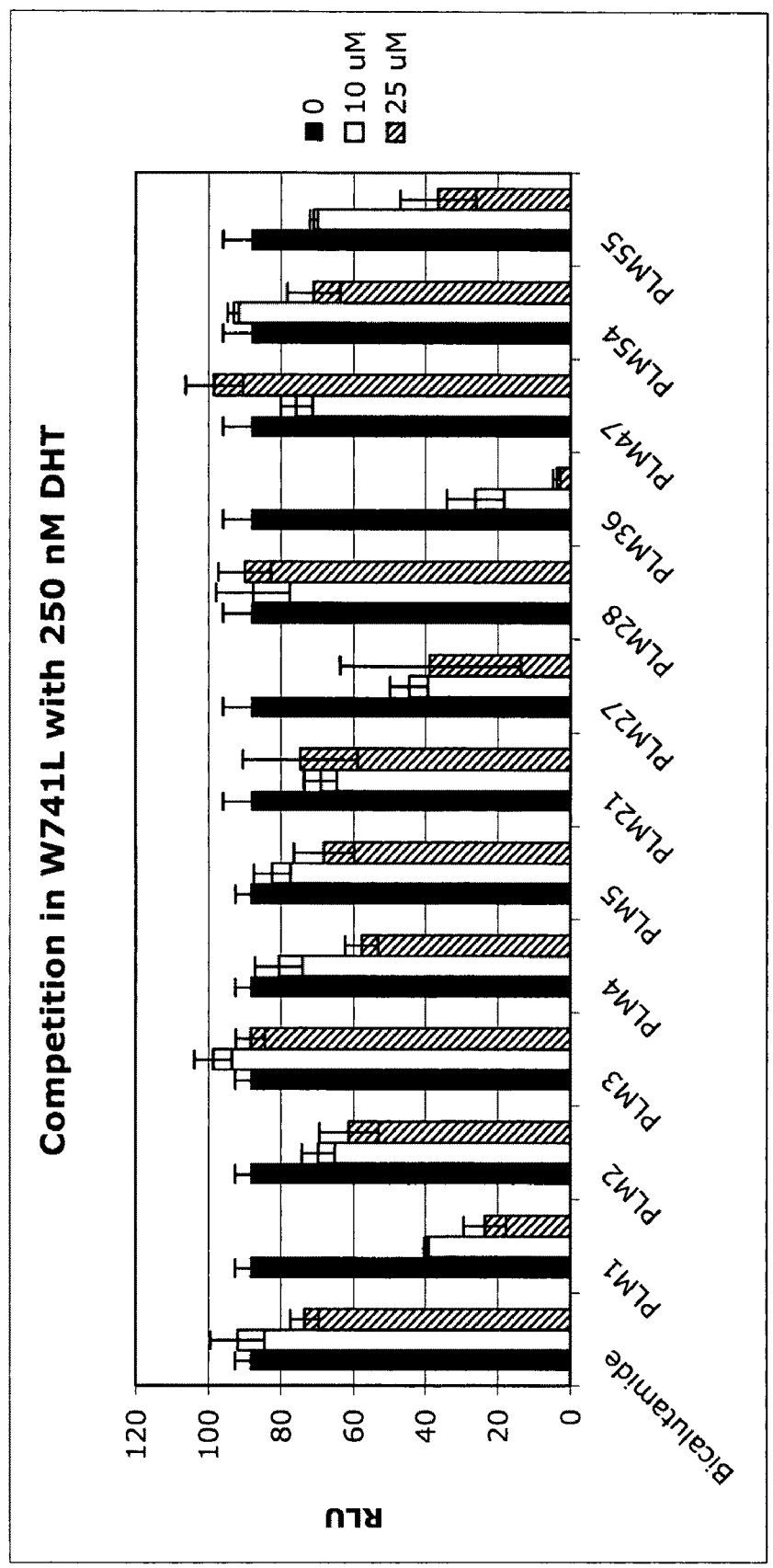
FIG. 5. Inhibition of DHT induced transcription with mutant androgen receptor, AR(W741L), in cell based assays. RLU: relative light units of luciferase reporter gene wherein maximal activity of AR(wild-type) with DHT is assigned a value of 100.
Figure 6:
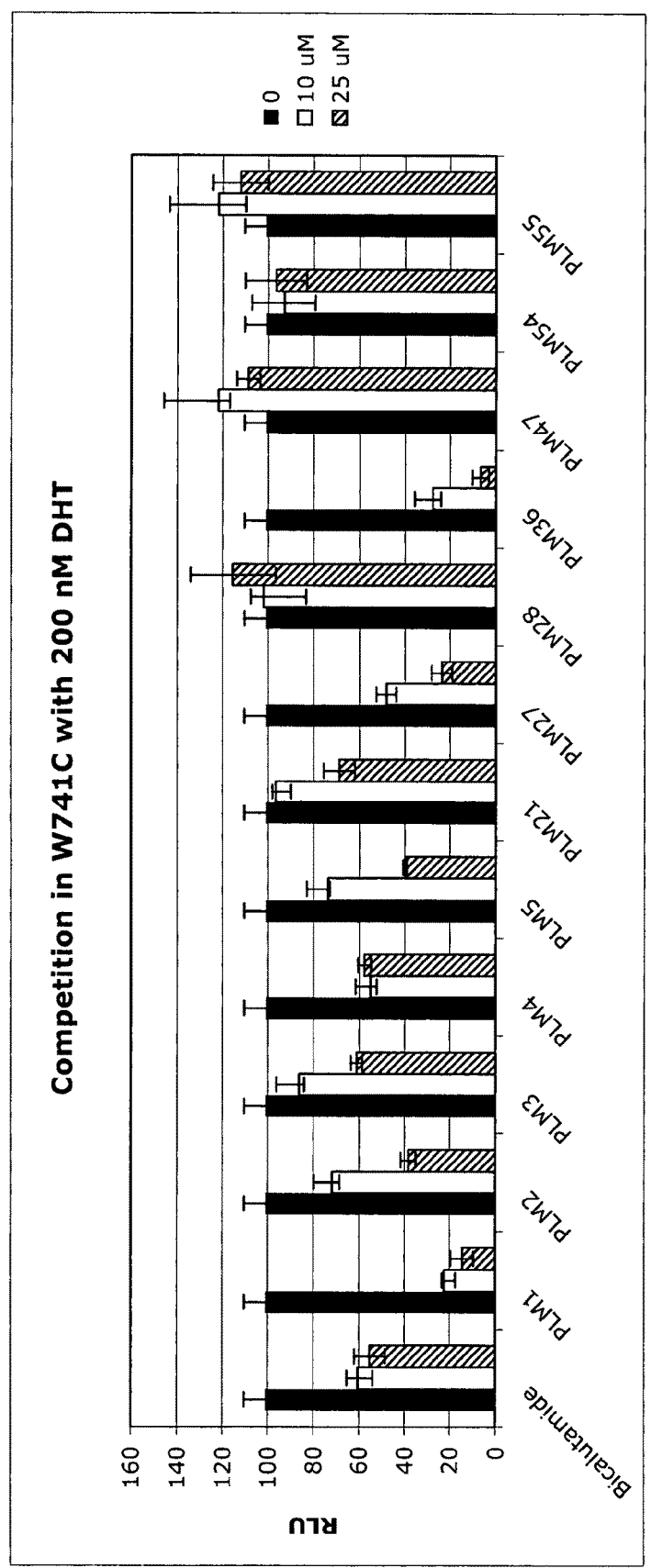
FIG. 6. Inhibition of DHT induced transcription with mutant androgen receptor, AR(W741C), in cell based assays. RLU: relative light units of luciferase reporter gene wherein maximal activity of AR(wild-type) with DHT is assigned a value of 100.
Figure 7:
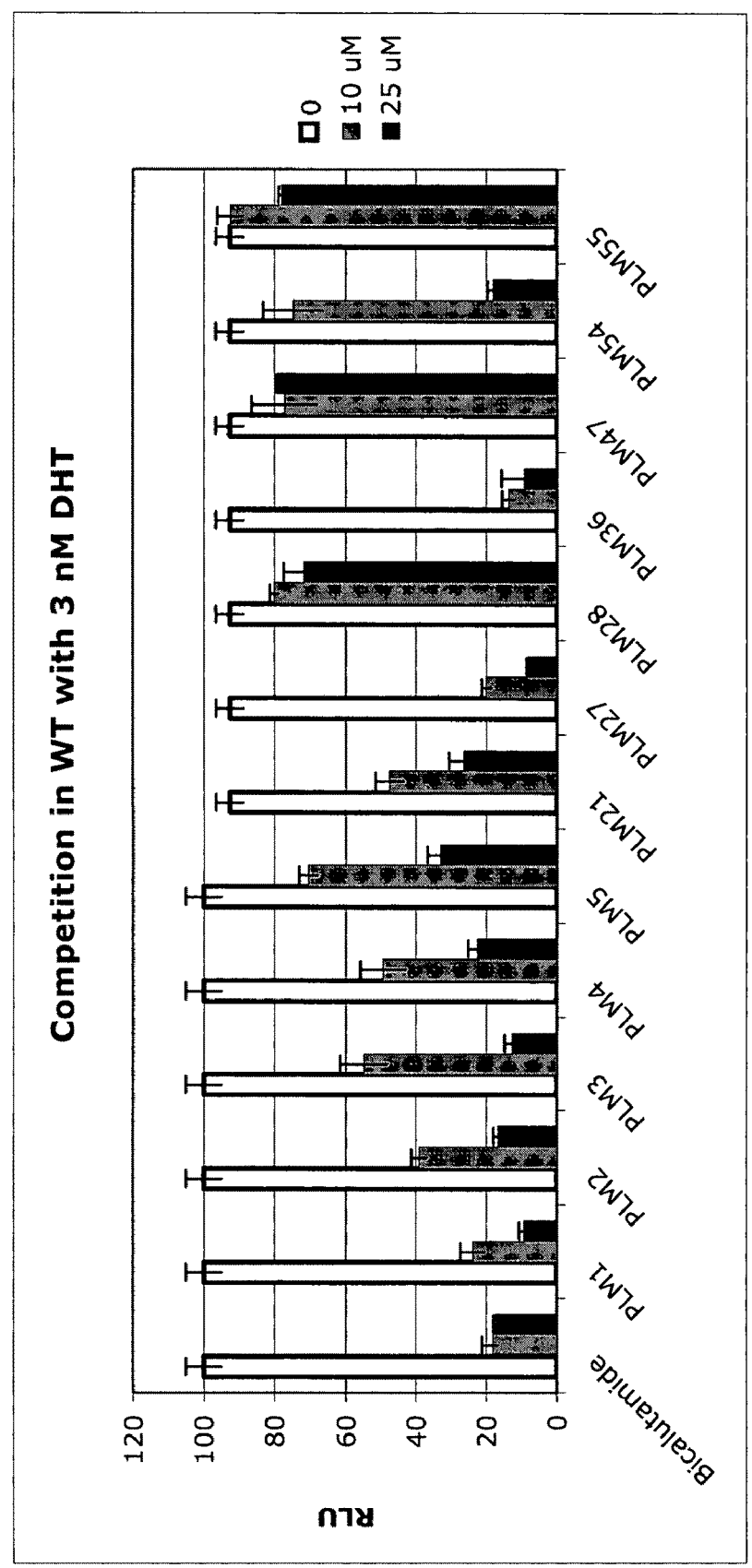
FIG. 7. Inhibition of DHT induced transcription with (wild-type) androgen receptor, AR(wt), in cell based assays. RLU: relative light units of luciferase reporter gene wherein maximal activity of AR(wild-type) with DHT is assigned a value of 100.
Figure 8:
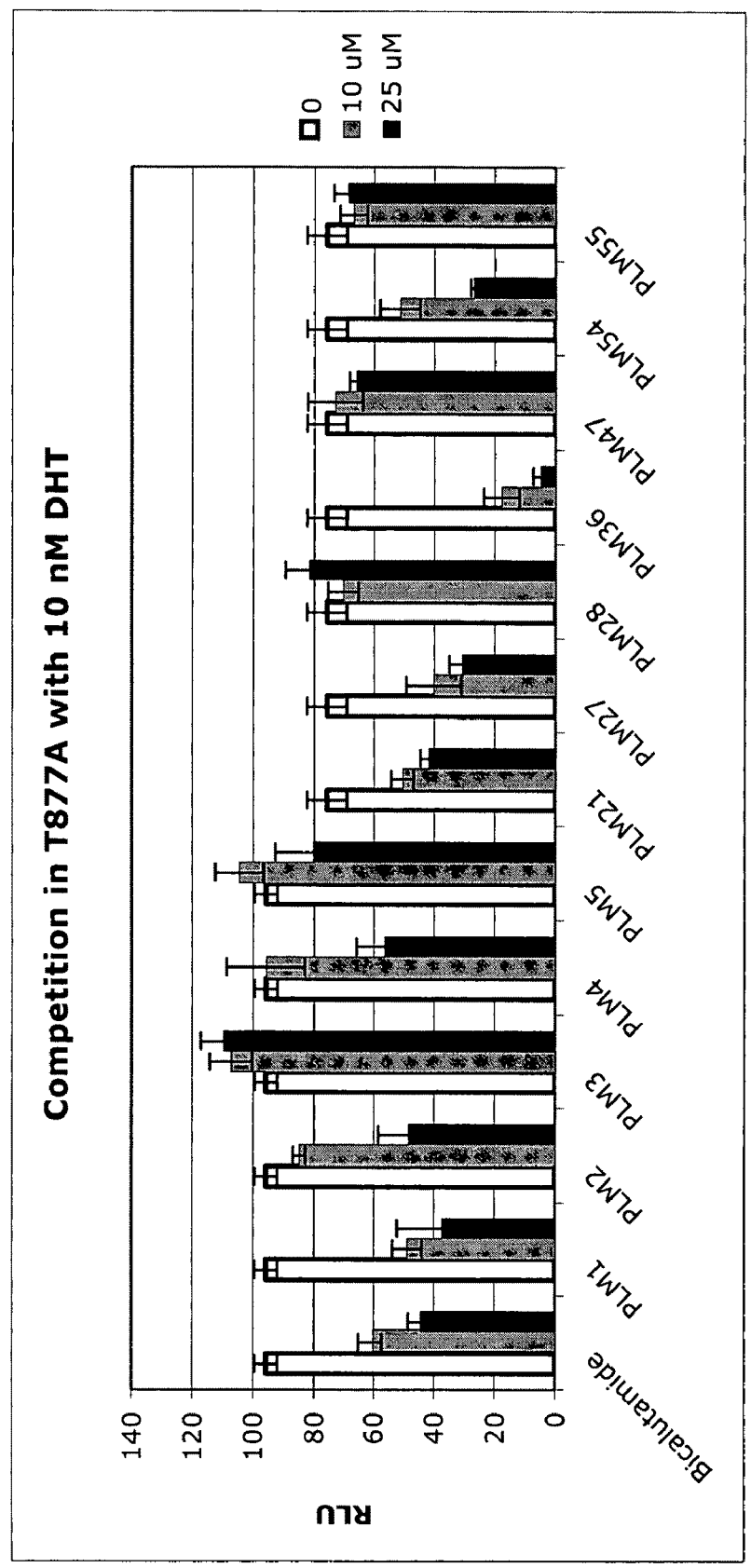
FIG. 8. Inhibition of DHT induced transcription with mutant androgen receptor, AR(T877A), in cell based assays. RLU: relative light units of luciferase reporter gene wherein maximal activity of AR(wild-type) with DHT is assigned a value of 100.

Applicants specifically incorporate the entire content of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

I. Definitions

In the context of this disclosure, a number of terms shall be utilized.

The term "androgen" includes all known compounds with androgenic activity. Androgenic activity of compounds may be determined in a variety of ways including in cell-based AR transcription assays and in biological activity assays where a compound can be demonstrated to have activity that is similar to the activity of known androgens. These assays can be performed using animals or tissues. For example, compounds with androgen activity in the prostate are able to stimulate prostate growth in rodents. Natural androgen metabolites that have biological activity can be used and include, for example, testosterone, and rostenedione, androstanedione, and dihydrotestosterone (DHT).

The term "androgen-dependent disorder" refers to any disorder that can benefit from a decrease in androgen stimulation and includes pathological conditions that depend on androgen stimulation. An "androgen-dependent disorder" can result from an excessive accumulation of testosterone or other androgenic hormone, increased sensitivity of androgen receptors to androgen, or an increase in androgen-stimulated transcription. Examples of "androgen-dependent disorders" include prostate cancer and skin disorders such as, for example, acne, seborrhea, hirsutism, alopecia, or hidradenitis suppurativa.

The term "androgen receptor" or "AR" refers to the androgen receptor protein as defined by its conserved amino acid coding sequence in an active or native structural conformation. Nucleic acid sequences encoding androgen receptors have been cloned and sequenced from numerous organisms. Representative organisms and GenBank® accession numbers for androgen receptor sequences therefrom include the following: frog (*Xenopus levis*; U67129), mouse (*Mus musculus*, 109558), rat (*Rattus norvegicus*, 292896), human (*Homo sapiens*, 105325), rabbit (*Oryctolagus cuniculus*, 577829), cow (*Bos taurus*, Z75313, Z75314, Z75315), canary (*Serinus canaria*, 414734), whiptail lizard (*Cnemidophous uniparens*, 1195596), and canine (*Canis familiaris*, AF197950).

The term "anti-androgen" as used herein refers to Formula I or Formula II compounds that specifically block the entry of androgens into cells of the body. Anti-androgens are believed to act by competitively inhibiting the action of androgens by binding to androgen receptors and/or mutant forms of the androgen receptor, and preventing androgens from binding to the receptors and entering the cell nucleus.

The terms "effective amount", "therapeutically effective amount", and "effective dosage" as used herein, refer to the amount of a Formula I or II compound that, when administered to a mammal in need, is effective to at least partially ameliorate a condition from which the mammal is suspected to suffer.

The term "mammal" refers to a human, a non-human primate, canine, feline, bovine, ovine, porcine, murine, or other veterinary or laboratory mammal. Those skilled in the art recognize that a therapy which reduces the severity of a pathology in one species of mammal is predictive of the effect of the therapy on another species of mammal. The skilled person also appreciates that credible animal models of human prostate cancer pathologies are known.

II. Anti-Androgen Compounds

One aspect is for a compound of the formula:

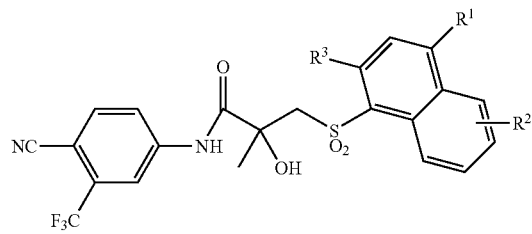
(I)

wherein $R^1$ is hydrogen, fluorine, chlorine, bromine, cyano, hydroxy, methyl acrylate, or $C_1$-$C_6$ alkyl optionally substituted with hydroxy;

$R^2$ is hydrogen, hydroxy, fluoro, chloro, cyano, $C_1$-$C_5$ alkanoate, $C_1$-$C_5$ alkylamino, or $C_1$-$C_6$ alkyl optionally substituted with hydroxy or acrylate; and $R^3$ is hydrogen, $C_1$-$C_6$ alkyl, fluoro, chloro, bromo, or cyano.

Formula I compounds of particular interest include, for example,

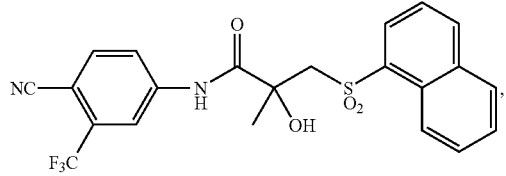
(III)

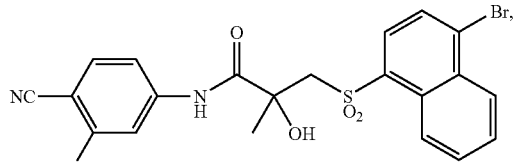
(IV)

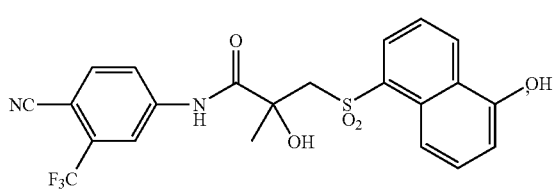
(V)

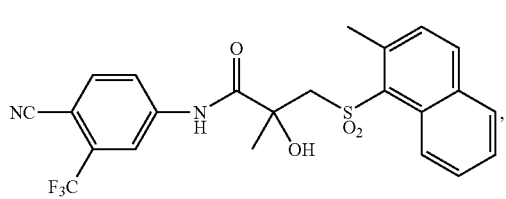
(VI)

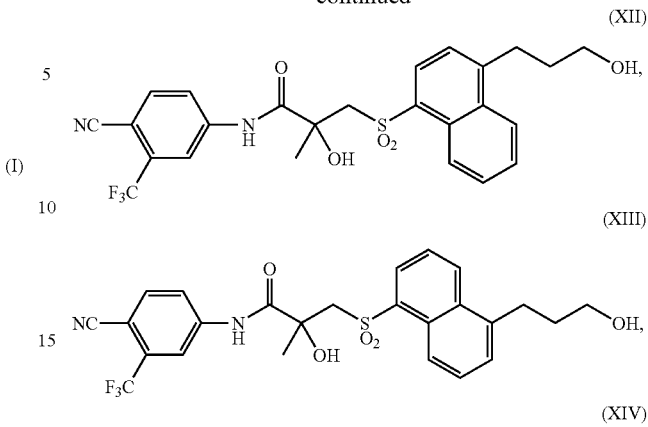
(XII)

(XIII)

(XIV)

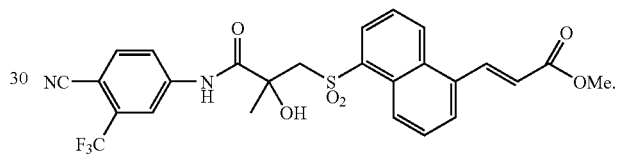
(XV)

Another aspect is for a compound of the formula:

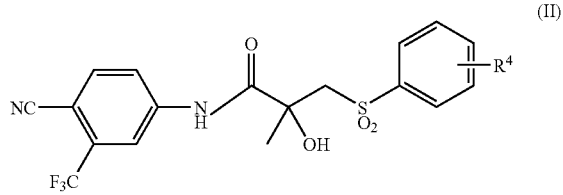
(II)

wherein $R^4$ is phenyl optionally substituted with hydroxy; $C_1$-$C_6$ phenylalkyl; $C_1$-$C_8$ alkoxy; or benzyl optionally substituted with hydroxy, $C_1$-$C_6$ alkoxy optionally substituted with methoxy or cyano, $C_1$-$C_6$ alkyl, $C_1$-$C_5$ alkanoate, or $C_1$-$C_5$ alkylamine.

Formula II compounds of particular interest include, for example,

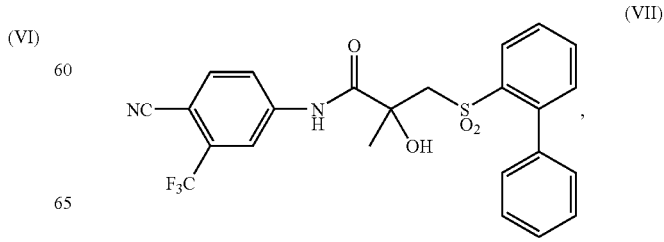
(VII)

-continued
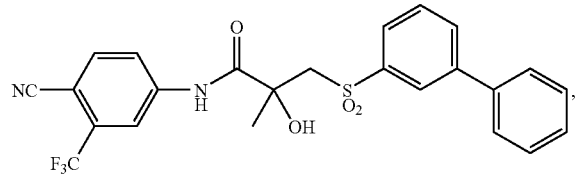
(VIII)
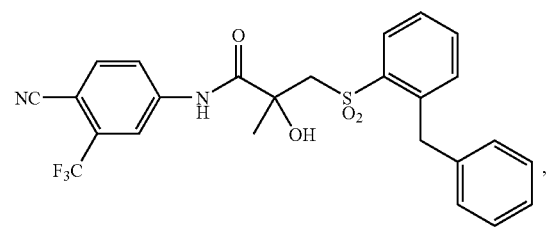
(IX)
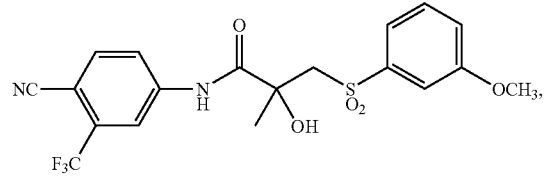
(X)
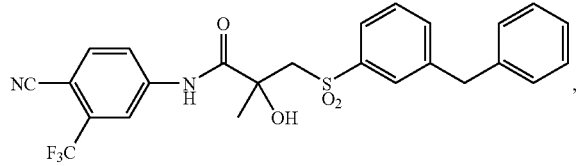
(XI)
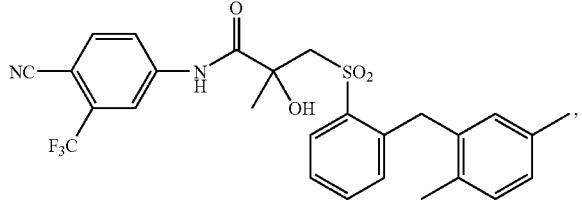
(XVI)
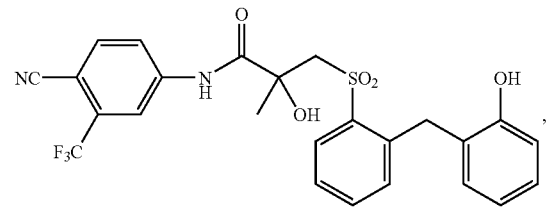
(XVII)
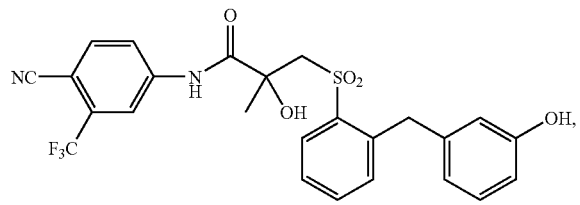
(XVIII)
-continued
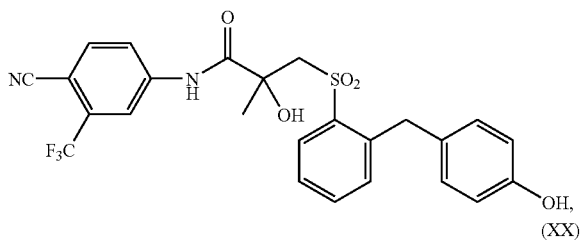
(XIX)
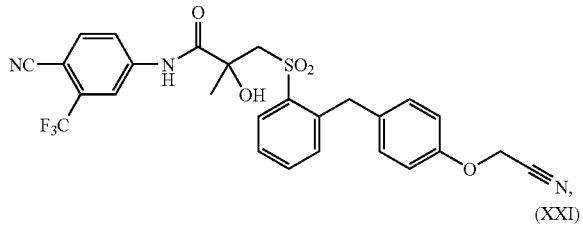
(XX)
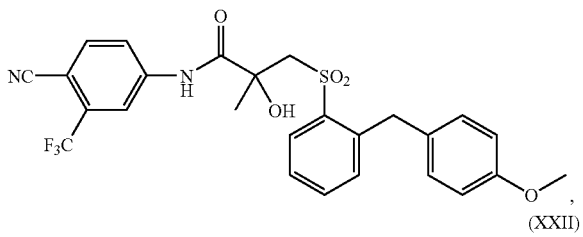
(XXI)
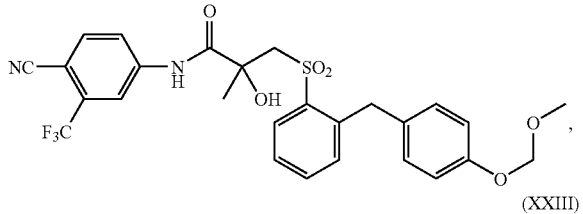
(XXII)
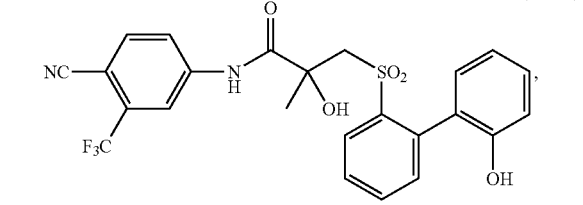
(XXIII)
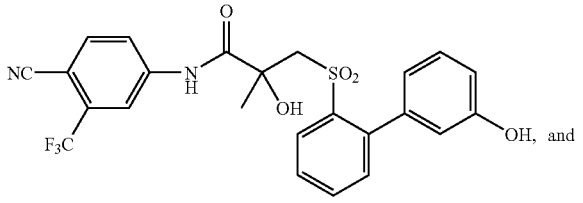
(XXIV)
and
(XXV)

III. General Formula I and II Compound Synthetic Scheme

Thiols were synthesized from their corresponding anilines or amines, when not commercially available. Briefly, concentrated hydrochloric acid was added to a cooled solution of amine or aniline dissolved in water. A cooled solution of sodium nitrite in water was added slowly and the reaction stirred for 30 minutes. This solution was then added to a solution of potassium ethyl xanthate in water warmed to 45° C. and stirred for a further 30 minutes. Diethyl ether was added and the organic layer was washed with 10% sodium hydroxide and water until neutral. The organic layer was dried over magnesium sulfate, filtered and evaporated. The crude product was then dissolved in ethanol and heated to reflux. Potassium hydroxide pellets were added and refluxing was continued overnight. The ethanol was evaporated. The residue was diluted with water and extracted with diethyl ether. The aqueous layer was acidified with 2 N HCl and extracted with diethyl ether. The organic layer was separated, dried over magnesium sulfate, filtered and evaporated to yield the crude thiol, which could be further purified by column chromatography if necessary. Alternatively, thiols can be generated by transition metal mediated cross coupling with aryl halides or aryl triflates (see, for example: Buchwald et al., Tetrahedron, 2004, 60, 7397, and Zheng et al., J. Organic Chemistry, 1998, 63, 9606).

Aryl and alkyl amines can be derived directly from their corresponding nitro compounds. Briefly, the nitro compound and 10% palladium on carbon were dissolved in methanol and purged with nitrogen then placed under an atmosphere of hydrogen overnight or until the reaction was complete. The reaction mixture was filtered and solvent evaporated to yield the desired amine.

The thiols were added to the epoxide, N-(4-Cyano-3-trifluorophenyl)methacrylamide epoxide, to form the sulfide intermediate. This epoxide was synthesized following published procedures. (For example: Chen et al., J. Organic Chemistry, 2003, 68, 10181 and Tucker, H., Crook, J. W. and Chesterson, J. W., J. Med. Chem. 1988, 31, 954.)

The epoxide ring opening was achieved using a base and the appropriate thiol in a suitable solvent. For example, sodium hydride (60% dispersed in mineral oil) was suspended in THF (tetrahydrofuran) and cooled to 0° C. A solution of the thiol in THF was added via syringe and stirred for 5 minutes. N-(4-Cyano-3-trifluorophenyl)methacrylamide epoxide dissolved in THF was added slowly. The reaction was allowed to warm to room temperature and stirred overnight. The solvent was evaporated. The residue was diluted with water and extracted with ethyl acetate. The organic layer was washed with water and brine, dried over magnesium sulfate, filtered and evaporated. The compound was purified by column chromatography.

The sulfide intermediate was oxidized to give the final desired sulfone compounds. Briefly, the sulfide was dissolved in dichloromethane and cooled to −78° C. 30% hydrogen peroxide was added followed by the slow addition of trifluoroacetic anhydride. The reaction was stirred at room temperature for 16 h. The reaction was diluted with dichloromethane and cold water and brine were added. The reaction was stirred for 20 minutes. The organic layer was separated, dried over magnesium sulfate, filtered and evaporated. The compound was purified by column chromatography.

Some of the compounds of Formulas I and II will exist as optical isomers. Any reference in this application to one of the compounds represented by Formula I or II is meant to encompass either a specific optical isomer or a mixture of optical isomers (unless it is expressly excluded). The specific optical isomers can be separated and recovered by techniques known in the art such as chromatography on chiral stationary phases or resolution via chiral salt formation and subsequent separation by selective crystallization. Alternatively, utilization of a specific optical isomer as the starting material will produce the corresponding isomer as the final product.

IV. Administration Of Anti-Androgens

Formula I or II compounds can be administered to subjects in a biologically compatible form suitable for pharmaceutical administration in vivo. By "biologically compatible form suitable for administration in vivo" is meant a form of the Formula I or II compound to be administered in which any toxic effects are outweighed by the therapeutic effects of the compound. The term subject is intended to include living organisms in which an immune response can be elicited, for example, mammals. Administration of a Formula I or II compound as described herein can be in any pharmacological form including a therapeutically active amount of a Formula I or II compound alone or in combination with a pharmaceutically acceptable carrier.

A therapeutically effective amount of a Formula I or II compound may vary according to factors such as the disease state, age, sex, and weight of the individual, and the ability of the compound to elicit a desired response in the individual. Dosage regime may be adjusted to provide the optimum therapeutic response. For example, several divided doses may be administered daily, or the dose may be proportionally reduced as indicated by the exigencies of the therapeutic situation.

The therapeutic or pharmaceutical compositions can be administered by any suitable route known in the art including, for example, intravenous, subcutaneous, intramuscular, transdermal, intrathecal, or intracerebral or administration to cells in ex vivo treatment protocols. Administration can be either rapid as by injection or over a period of time as by slow infusion or administration of slow release formulation. For treating prostate cancer, administration of the therapeutic or pharmaceutical compositions of the present invention can be performed, for example, orally or subcutaneously. For skin disorders, administration of the therapeutic or pharmaceutical compositions of the present invention can be performed, for example, topical or oral administration.

Formula I or II compounds can also be linked or conjugated with agents that provide desirable pharmaceutical or pharmacodynamic properties. For example, Formula I or II compounds can be coupled to any substance known in the art to promote penetration or transport across the blood-brain barrier such as an antibody to the transferrin receptor, and administered by intravenous injection (see, e.g., Friden P M et al., Science 259:373-77 (1993)). Furthermore, Formula I or II compounds can be stably linked to a polymer such as polyethylene glycol to obtain desirable properties of solubility, stability, half-life, and other pharmaceutically advantageous properties (see, e.g., Davis et al., Enzyme Eng. 4:169-73 (1978); Burnham N L, Am. J. Hosp. Pharm. 51:210-18 (1994)).

Furthermore, Formula I or II compounds can be in a composition which aids in delivery into the cytosol of a cell. For example, a Formula I or II compound may be conjugated with a carrier moiety such as a liposome that is capable of delivering the compound into the cytosol of a cell. Such methods are well known in the art (see, e.g., Amselem S et al., Chem. Phys. Lipids 64:219-37 (1993)). Alternatively, the compound can be delivered directly into a cell by microinjection.

The Formula I or II compounds are usefully employed in the form of pharmaceutical preparations. Such preparations are made in a manner well known in the pharmaceutical art.

One preferred preparation utilizes a vehicle of physiological saline solution, but it is contemplated that other pharmaceutically acceptable carriers such as physiological concentrations of other non-toxic salts, five percent aqueous glucose solution, sterile water or the like may also be used. As used herein "pharmaceutically acceptable carrier" includes any and all solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with the active compound, use thereof in the therapeutic compositions is contemplated. Supplementary active compounds can also be incorporated into the compositions. It may also be desirable that a suitable buffer be present in the composition. Such solutions can, if desired, be lyophilized and stored in a sterile ampoule ready for reconstitution by the addition of sterile water for ready injection. The primary solvent can be aqueous or alternatively non-aqueous. Formula I or II compounds can also be incorporated into a solid or semi-solid biologically compatible matrix which can be implanted into tissues requiring treatment.

The carrier can also contain other pharmaceutically-acceptable excipients for modifying or maintaining the pH, osmolarity, viscosity, clarity, color, sterility, stability, rate of dissolution, or odor of the formulation. Similarly, the carrier may contain still other pharmaceutically-acceptable excipients for modifying or maintaining release or absorption or penetration across the blood-brain barrier. Such excipients are those substances usually and customarily employed to formulate dosages for parenteral administration in either unit dosage or multi-dose form or for direct infusion by continuous or periodic infusion.

Formula I or II compounds may be used individually or in combination and with other anti-androgens or other treatments, such as flutamide, bicalutamide, and nilutamide; irradiation; heat; luteinizing hormone-releasing hormone or luteinizing hormone-releasing hormone analog, such as goserelin; or the like, as may be conventionally employed and as may be moderated for use in conjunction with the Formula I or II compounds.

Dose administration can be repeated depending upon the pharmacokinetic parameters of the dosage formulation and the route of administration used.

It is also provided that certain formulations containing the Formula I or II compounds are to be administered orally. Such formulations are preferably encapsulated and formulated with suitable carriers in solid dosage forms. Some examples of suitable carriers, excipients, and diluents include lactose, dextrose, sucrose, sorbitol, mannitol, starches, gum acacia, calcium phosphate, alginates, calcium silicate, microcrystalline cellulose, polyvinylpyrrolidone, cellulose, gelatin, syrup, methyl cellulose, methyl- and propylhydroxybenzoates, talc, magnesium, stearate, water, mineral oil, and the like. The formulations can additionally include lubricating agents, wetting agents, emulsifying and suspending agents, preserving agents, sweetening agents, or flavoring agents. The compositions may be formulated so as to provide rapid, sustained, or delayed release of the active ingredients after administration to the patient by employing procedures well known in the art. The formulations can also contain substances that diminish proteolytic degradation and/or substances which promote absorption such as, for example, surface active agents.

In some embodiments, Formula I or II compounds are utilized for the treatment of androgen-related diseases of the skin such as, for example, acne, seborrhea, hirsutism, alopecia, or hidradenitis suppurativa. When used for any of these purposes, the Formula I or II compounds are preferably administered topically together with a conventional topical carrier or diluent. When used topically, it is preferred that the diluent or carrier does not promote transdermal penetration of the active ingredients into the blood stream or other tissues where they might cause unwanted systemic effects.

It is especially advantageous to formulate compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved and (b) the limitations inherent in the art of compounding such an active compound for the treatment of sensitivity in individuals. The specific dose can be readily calculated by one of ordinary skill in the art, e.g., according to the approximate body weight or body surface area of the patient or the volume of body space to be occupied. The dose will also be calculated dependent upon the particular route of administration selected. Further refinement of the calculations necessary to determine the appropriate dosage for treatment is routinely made by those of ordinary skill in the art. Such calculations can be made without undue experimentation by one skilled in the art in light of the anti-androgen activity disclosed herein in assay preparations of target cells. Exact dosages are determined in conjunction with standard dose-response studies. It will be understood that the amount of the composition actually administered will be determined by a practitioner, in the light of the relevant circumstances including the condition or conditions to be treated, the choice of composition to be administered, the age, weight, and response of the individual patient, the severity of the patient's symptoms, and the chosen route of administration.

Toxicity and therapeutic efficacy of such compounds can be determined by standard pharmaceutical procedures in cell cultures or experimental animals, for example, for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

In one embodiment, the present invention provides a method for monitoring the effectiveness of treatment of a subject with a Formula I or II compound comprising the steps of (i) obtaining a pre-administration sample from a subject prior to administration of the compound; (ii) detecting the level of androgen receptor activity in the pre-administration sample; (iii) obtaining one or more post-administration samples from the subject; (iv) detecting the level of androgen receptor activity in the post-administration samples; (v) comparing the level of androgen receptor activity in the pre-administration sample with the post administration sample or samples; and (vi) altering the administration of the compound to the subject accordingly. For example, increased administration of the Formula I or II compound may be desirable to decrease the activity of androgen receptor to lower levels than detected, that is, to increase the effectiveness of the compound. Alternatively, decreased administration of the compound may be desirable to increase androgen receptor activity to higher levels than detected, that is, to decrease the effectiveness of the compound.

In another embodiment, the ability of a Formula I or II compound to modulate androgen receptor activity in a subject that would benefit from modulation of the activity of the androgen receptor can be measured by detecting an improvement in the condition of the patient after the administration of the compound. Such improvement can be readily measured by one of ordinary skill in the art using indicators appropriate for the specific condition of the patient. Monitoring the response of the patient by measuring changes in the condition of the patient is preferred in situations were the collection of biopsy materials would pose an increased risk and/or detriment to the patient.

Furthermore, in the treatment of disease conditions, compositions containing Formula I or II compounds can be administered exogenously and it would likely be desirable to achieve certain target levels of Formula I or II compounds in sera, in any desired tissue compartment, or in the affected tissue. It would, therefore, be advantageous to be able to monitor the levels of Formula I or II compounds in a patient or in a biological sample including a tissue biopsy sample obtained from a patient. Accordingly, the present invention also provides methods for detecting the presence of Formula I or II compounds in a sample from a patient.

All of the compositions and methods disclosed and claimed herein can be made and executed without undue experimentation in light of the present disclosure. It will be apparent to those of skill in the art that variations may be applied to the compositions and methods and in the steps or in the sequence of steps of the method described herein without departing from the concept, spirit, and scope of the invention. More specifically, it will be apparent that certain agents which are chemically or biologically related may be substituted for the agents described herein while the same or similar results would be achieved. All such similar substitutes and modifications apparent to those skilled in the art are deemed to be within the spirit, scope, and concept of the invention as defined by the appended claims.

EXAMPLES

The present invention is further defined in the following Examples. It should be understood that these Examples are given by way of illustration only. From the above discussion and these Examples, one skilled in the art can ascertain the preferred features of this invention, and without departing from the spirit and scope thereof, can make various changes and modifications of the invention to adapt it to various uses and conditions.

The following abbreviations are here defined: PLM1: N-(4-Cyano-3-(trifluoromethyl)phenyl)-2-hydroxy-2-methyl-3-(naphthalen-1-ylsulfonyl)propanamide; PLM2: 3-(2-benzylphenylsulfonyl)-N-(4-Cyano-3-(trifluoromethyl)phenyl)-2-hydroxy-2-methylpropanamide; PLM3: 3-(3-benzylphenylsulfonyl)-N-(4-Cyano-3-(trifluoromethyl) phenyl)-2-hydroxy-2-methylpropanamide; PLM4: 3-(2-phenylphenylsulfonyl)-N-(4-Cyano-3-(trifluoromethyl) phenyl)-2-hydroxy-2-methylpropanamide; PLM5: 3-(3-methoxyphenylsulfonyl)-N-(4-Cyano-3-(trifluoromethyl) phenyl)-2-hydroxy-2-methylpropanamide; PLM21: 3-(1-hydroxynaphthalen-5-ylsulfonyl)-N-(4-cyano-3-(trifluoromethyl)phenyl)-2-hydroxy-2-methylpropanamide; PLM9: 3-(1-bromonaphthalen-4-ylsulfonyl)-N-(4-Cyano-3-(trifluoromethyl)phenyl)-2-hydroxy-2-methylpropanamide; PLM13: 3-(1-Chloronaphthalen-4-ylsulfonyl)-N-(4-Cyano-3-(trifluoromethyl)phenyl)-2-hydroxy-2-methylpropanamide; PLM11: 3-(2-methylnaphthalen-1-ylsulfonyl)-N-(4-Cyano-3-(trifluoromethyl)phenyl)-2-hydroxy-2-methylpropanamide; PLM12: 3-(1-cyanonaphthalen-4-ylsulfonyl)-N-(4-Cyano-3-(trifluoromethyl)phenyl)-2-hydroxy-2-methylpropanamide; PLM54: 3-(1-phenylphenylsulfonyl)-N-(4-cyano-3-(trifluoromethyl) phenyl)-2-hydroxy-2-methylpropanamide; PLM55: N-(4-Cyano-3-(trifluoromethyl)phenyl)-2-hydroxy-2-methyl-3-(naphthalen-2-ylsulfonyl)propanamide; PLM14: N-(4-Cyano-3-(trifluoromethyl)phenyl)-2-hydroxy-3-(4-(3-hydroxypropyl)naphthalen-1-ylsulfonyl)-2-methylpropanamide; PLM15: N-(4-Cyano-3-(trifluoromethyl)phenyl)-2-hydroxy-3-(5-(3-hydroxypropyl)naphthalen-1-ylsulfonyl)-2-methylpropanamide; PLM16: (E)-methyl 3-(4-(3-(4-Cyano-3-(trifluoromethyl)phenylamino)-2-hydroxy-2-methyl-3-oxopropylsulfonyl)naphthalen-1-yl)acrylate; PLM18: (E)-methyl 3-(5-(3-(4-Cyano-3-(trifluoromethyl)phenylamino)-2-hydroxy-2-methyl-3-oxopropylsulfonyl)naphthalen-1-yl) acrylate; PAN71: N-(4-Cyano-3-(trifluoromethyl)phenyl)-3-(2-(2,5-dimethylbenzyl)phenylsulfonyl)-2-hydroxy-2-methylpropanamide; PAN11: N-(4-Cyano-3-(trifluoromethyl)phenyl)-2-hydroxy-3-(2-(2-hydroxybenzyl)phenylsulfonyl)-2-methylpropanamide; PAN21: N-(4-cyano-3-(trifluoromethyl)phenyl)-2-hydroxy-3-(2-(3-hydroxybenzyl)phenylsulfonyl)-2-methylpropanamide; PAN31: N-(4-Cyano-3-(trifluoromethyl)phenyl)-2-hydroxy-3-(2-(4-hydroxybenzyl)phenylsulfonyl)-2-methylpropanamide; PAN32: N-(4-Cyano-3-(trifluoromethyl)phenyl)-3-(2-(4-(cyanomethoxy)benzyl) phenylsulfonyl)-2-hydroxy-2-methylpropanamide; PAN33: N-(4-Cyano-3-(trifluoromethyl)phenyl)-2-hydroxy-3-(2-(4-methoxybenzyl)phenylsulfonyl)-2-methylpropanamide; PAN37: N-(4-Cyano-3-(trifluoromethyl)phenyl)-2-hydroxy-3-(2-(4-(methoxymethoxy)benzyl)phenylsulfonyl)-2-methylpropanamide; PAN41: N-(4-Cyano-3-(trifluoromethyl) phenyl)-2-hydroxy-3-(2'-hydroxybiphenyl-2-ylsulfonyl)-2-methylpropanamide; PAN51: N-(4-Cyano-3-(trifluoromethyl)phenyl)-2-hydroxy-3-(3'-hydroxybiphenyl-2-ylsulfonyl)-2-methylpropanamide; PAN61: N-(4-Cyano- 3-(trifluoromethyl)phenyl)-2-hydroxy-3-(4'-hydroxybiphenyl-2-ylsulfonyl)-2-methylpropanamide.

Example 1

N-(4-Cyano-3-(trifluoromethyl)phenyl)-2-hydroxy-2-methyl-3-(naphthalen-1-ylthio)propanamide To a stirred suspension of sodium hydride (60% dispersed in mineral oil, 9.7 mg, 0.242 mmol) in THF (0.1 mL) was added a solution of 1-naphthalenethiol (36.9 mg, 0.23 mmol) in THF (0.07 mL) at 0° C. The mixture was stirred for 5 minutes. A solution of N-(4-Cyano-3-trifluorophenyl)methacrylamide epoxide (50 mg, 0.185 mmol) in THF (0.25 mL) was added slowly. The reaction was allowed to warm to room temperature and stirred overnight. The reaction mixture was concentrated and then diluted with water and extracted with ethyl acetate (50 mL). The organic extract was washed with water (25 mL) and brine (25 mL), dried over magnesium sulfate, filtered and evaporated. Purification by column chromatography (hexane:EtOAc 50:50) yielded 31 mg of desired product. Production of N-(4-Cyano-3-(trifluoromethyl)phenyl)-2-hydroxy-2-methyl-3-(naphthalen-1-ylthio)propanamide was confirmed by 1-H NMR, 13-C NMR, and mass spectral analysis.

Example 2

N-(4-Cyano-3-(trifluoromethyl)phenyl)-2-hydroxy-2-methyl-3-(naphthalen-1-ylsulfonyl)propanamide (PLM1)

N-(4-Cyano-3-(trifluoromethyl)phenyl)-2-hydroxy-2-methyl-3-(naphthalen-1-ylthio)propanamide (31 mg, 0.072 mmol) was dissolved in dichloromethane (0.2 mL) and cooled to −78° C. 30% hydrogen peroxide (16.7 µL, 0.58 mmol) was added followed by the slow addition of trifluoroacetic anhydride (62 µL, 0.43 mmol). The reaction was stirred at room temperature for 16 h. The reaction was diluted with dichloromethane. Cold water and brine were added and the reaction was stirred for 20 minutes. The organic layer was separated, dried over magnesium sulfate, filtered and evaporated. Purification by column chromatography (hexane:EtOAc 50:50) yielded 25 mg of desired product. Production of PLM1 was confirmed by 1-H NMR, 13-C NMR, and mass spectral analysis.

Example 3

S-2-benzylphenyl-O-ethyl carbonodithioate

Concentrated hydrochloric acid (0.4 mL) was added slowly to a solution of 2-benzylaniline (500 mg, 2.73 mmol) in water (7.3 mL) at 0° C. A cooled solution of sodium nitrite (188 mg, 2.73 mmol) in water (1.5 mL) was added, and the mixture was stirred for 30 minutes. This solution was then added to a solution of potassium ethyl xanthate (525 mg, 3.28 mmol) in water (0.65 mL) warmed to 45° C. The reaction mixture was stirred for an additional 30 minutes. Diethyl ether (25 mL) was added, and the organic layer was washed with 10% sodium hydroxide solution until neutral. The organic layer was dried over magnesium sulfate, filtered and evaporated. The product was used directly in Example 4.

Example 4

2-benzylthiophenol

S-2-benzylphenyl-O-ethyl carbonodithioate (787 mg, 2.72 mmol) was dissolved in ethanol (8.2 mL) and heated to reflux. Potassium hydroxide pellets (654 mg, 11.65 mmol) were added slowly, and the solution was refluxed overnight. The solution was concentrated, and the residue was diluted with water (10 mL) and washed with diethyl ether (10 mL). The aqueous layer was acidified with 2 N HCl and extracted with diethyl ether. The organic extract was separated, dried over magnesium sulfate, filtered and evaporated to yield 289 mg of the crude thiol, which was used directly in Example 5.

Example 5

3-(2-benzylphenylthio)-N-(4-Cyano-3-(trifluoromethyl)phenyl)-2-hydroxy-2-methylpropanamide To a stirred suspension of sodium hydride (60% dispersed in mineral oil, 11 mg, 0.26 mmol) in THF (0.11 mL) was added slowly a solution of 2-benzylbenzenethiol (51 mg, 0.25 mmol) in THF (0.08 mL) at 0° C. After stirring the mixture for 5 minutes, a solution of N-(4- Cyano-3-trifluorophenyl)methacrylamide epoxide (55 mg, 0.202 mmol) in THF (0.28 mL) was added slowly. The reaction was allowed to warm to room temperature and stirred overnight. The THF was evaporated. The mixture was diluted with water and extracted with ethyl acetate (50 mL). The organic layer was washed with water (25 mL) and brine (25 mL), dried over magnesium sulfate, filtered and evaporated. Purification by column chromatography (hexane:EtOAc 50:50) yielded 32 mg of desired product. Production of 3-(2-benzylphenylthio)-N-(4-Cyano-3-(trifluoromethyl)phenyl)-2-hydroxy-2-methylpropanamide was confirmed by 1-H NMR, 13-C NMR, and mass spectral analysis.

Example 6

3-(2-benzylphenylsulfonyl)-N-(4-Cyano-3-(trifluoromethyl)phenyl)-2-hydroxy-2-methylpropanamide (PLM2)

3-(2-benzylphenylthio)-N-(4-cyano-3-(trifluoromethyl)phenyl)-2-hydroxy-2-methylpropanamide (32 mg, 0.068 mmol) was dissolved in dichloromethane (0.1 mL) and cooled to −78° C. 30% hydrogen peroxide (12 µL, 0.4 mmol) was added followed by the slow addition of trifluoroacetic anhydride (48 µL, 0.34 mmol). The reaction was stirred at room temperature for 16 h. The reaction was diluted with dichloromethane. Cold water and brine were added, and the reaction was stirred for 20 minutes. The organic layer was separated, dried over magnesium sulfate, filtered and evaporated. Purification by column chromatography (hexane:EtOAc 50:50) yielded 14 mg of desired product. Production of PLM2 was confirmed by 13-C NMR and mass spectral analysis.

Example 7

S-3-benzylphenyl-O-ethyl carbonodithioate

Concentrated hydrochloric acid (0.2 mL) was added slowly to a solution of 3-benzylaniline (250 mg, 1.36 mmol)

in water (3.7 mL) at 0° C. A cooled solution of sodium nitrite (94 mg, 1.36 mmol) in water (0.73 mL) was added, and the mixture was stirred for 30 minutes. This solution was then added to a solution of potassium ethyl xanthate (261 mg, 1.63 mmol) in water (0.33 mL) at 45° C. The reaction mixture was stirred for an additional 30 minutes. Diethyl ether (25 mL) was added, and the organic layer was washed with 10% sodium hydroxide solution until neutral. The organic layer was dried over magnesium sulfate, filtered and evaporated to afford the crude product, which was used directly in Example 8.

Example 8

3-benzylbenzenethiol

S-3-benzylphenyl-O-ethyl carbonodithioate (392 mg, 1.36 mmol) was dissolved in ethanol (4.1 mL) and heated to reflux. Once refluxing, potassium hydroxide pellets (326 mg, 5.81 mmol) were added slowly and refluxing was continued overnight. The ethanol was evaporated. The residue was diluted with water (10 mL) and washed with diethyl ether (10 mL). The aqueous layer was acidified with 2 N HCl and extracted with diethyl ether. The organic layer was separated, dried over magnesium sulfate, filtered and evaporated. Purification by column chromatography (hexane:EtOAc 95:5) yielded 44 mg of desired product, which was used directly in Example 9.

Example 9

3-(3-benzylphenylthio)-N-(4-Cyano-3-(trifluoromethyl)phenyl)-2-hydroxy-2-methylpropanamide To a stirred suspension of sodium hydride (60% dispersed in mineral oil, 11 mg, 0.26 mmol) in THF (0.11 mL) was added a solution of 3-benzylbenzenethiol (52 mg, 0.26 mmol) in THF (0.08 mL) at 0° C. The mixture was stirred for 5 minutes. A solution of N-(4-Cyano-3-trifluorophenyl)methacrylamide epoxide (56 mg, 0.207 mmol) in THF (0.28 mL) was added slowly. The reaction was allowed to warm to room temperature and stirred overnight. The THF was evaporated. The mixture was diluted with water and extracted with ethyl acetate (50 mL). The organic layer was washed with water (25 mL) and brine (25 mL), dried over magnesium sulfate, filtered and evaporated. Purification by column chromatography (hexane:EtOAc 50:50) yielded 15.5 mg of desired product. Production of 3-(3-benzylphenylthio)-N-(4-Cyano-3-(trifluoromethyl)phenyl)-2-hydroxy-2-methylpropanamide was confirmed by 1-H NMR, 13-C NMR, and mass spectral analysis.

Example 10

3-(3-benzylphenylsulfonyl)-N-(4-Cyano-3-(trifluoromethyl)phenyl)-2-hydroxy-2-methylpropanamide (PLM3)

3-(3-benzylphenylthio)-N-(4-cyano-3-(trifluoromethyl)phenyl)-2-hydroxy-2-methylpropanamide (15 mg, 0.033 mmol) was dissolved in dichloromethane (0.05 mL) and cooled to −78° C. 30% hydrogen peroxide (5.7 µL, 0.2 mmol) was added followed by the slow addition of trifluoroacetic anhydride (23 µL, 0.17 mmol). The reaction was stirred at room temperature for 16 h. The reaction was diluted with dichloromethane. Cold water and brine were added, and the reaction was stirred for 20 minutes. The organic layer was separated, dried over magnesium sulfate, filtered and evaporated. Purification by column chromatography (hexane:EtOAc 50:50) yielded 11 mg of desired product. Production of PLM3 was confirmed by 1-H NMR, 13-C NMR, and mass spectral analysis.

Example 11

3-aminobiphenyl 3-nitrobiphenyl (500 mg, 2.5 mmol) and 10% palladium on carbon (267 mg, 2.5 mmol) were dissolved in methanol (1 mL) and purged with nitrogen and placed under an atmosphere of hydrogen overnight. The reaction mixture was filtered and evaporated to yield 326 mg of the desired amine, which was used directly in Example 12.

Example 12

S-3-phenylphenyl-O-ethyl carbonodithioate

Concentrated hydrochloric acid (0.26 mL) was added to a solution of 3-aminobiphenyl (326 mg, 1.82 mmol) in water (4.9 mL) at 0° C. A cooled solution of sodium nitrite (125 mg, 1.82 mmol) in water (0.98 mL) was added, and the mixture was stirred for 30 minutes. This solution was then added to a solution of potassium ethyl xanthate (350 mg, 2.18 mmol) in water (0.44 mL) warmed to 45° C. The reaction mixture was stirred for an additional 30 minutes. Diethyl ether (25 mL) was added, and the organic layer was washed with 10% sodium hydroxide solution followed by water until neutral. The organic layer was dried over magnesium sulfate, filtered and evaporated. The crude product was used directly in Example 13.

Example 13

3-phenylbenzenethiol

To a refluxing solution of S-3-phenylphenyl-O-ethyl carbonodithioate (543 mg, 1.82 mmol) in ethanol (5.5 mL) was added slowly potassium hydroxide pellets (436 mg, 7.77 mmol). After refluxing overnight, the solvent was evaporated. The residue was diluted with water (10 mL) and washed with diethyl ether (10 mL). The aqueous layer was acidified with 2 N HCl and extracted with diethyl ether. The organic layer was separated, dried over magnesium sulfate, filtered and evaporated to yield 171 mg of the crude thiol that was used directly in Example 14.

Example 14

3-(2-phenylphenylthio)-N-(4-Cyano-3-(trifluoromethyl)phenyl)-2-hydroxy-2-methylpropanamide To a stirred suspension of sodium hydride (60% dispersed in mineral oil, 9.7 mg, 0.24 mmol) in THF (0.1 mL) was added a solution of 3-phenylbenzenethiol (46 mg, 0.23 mmol) in THF (0.08 mL) at 0° C. The mixture was stirred for 5 minutes. N-(4-Cyano-3-trifluorophenyl)methacrylamide epoxide (50 mg, 0.185 mmol) was dissolved in THF (0.25 mL) and added slowly. The reaction was allowed to warm to room temperature and stirred overnight. The THF was evaporated. The mixture was diluted with water and extracted with ethyl acetate (50 mL). The organic layer was washed with water (25 mL) and brine (25 mL), dried over magnesium sulfate, filtered and evaporated. Purification by column chromatography (hexane:EtOAc 50:50) yielded 41 mg of desired product. Production of 3-(2-phenylphenylthio)-N-(4-Cyano-3-(trifluoromethyl)phenyl)-2-hydroxy-2-methylpropanamide was confirmed by 1-H NMR, 13-C NMR, and mass spectral analysis.

Example 15

3-(2-phenylphenylsulfonyl)-N-(4-Cyano-3-(trifluoromethyl)phenyl)-2-hydroxy-2-methylpropanamide, (PLM4)

To a solution of 3-(2-phenylphenylthio)-N-(4-Cyano-3-(trifluoromethyl)phenyl)-2-hydroxy-2-methylpropanamide (41 mg, 0.093 mmol) in dichloromethane (0.13 mL) at −78° C. was added 30% hydrogen peroxide (15.5 µL, 0.54 mmol) followed by the slow addition of trifluoroacetic anhydride (63 µL, 0.45 mmol). The reaction was stirred at room temperature for 16 h. The reaction was diluted with dichloromethane. Cold water and brine were added, and the reaction was stirred for 20 minutes. The organic layer was separated, dried over magnesium sulfate, filtered and evaporated. Purification by column chromatography (hexane:EtOAc 50:50) yielded 23 mg of desired product. Production of PLM4 was confirmed by 1-H NMR and 13-C NMR.

Example 16

3-(3-methoxyphenylthio)-N-(4-Cyano-3-(trifluoromethyl)phenyl)-2-hydroxy-2-methylpropanamide To a stirred suspension of sodium hydride (60% dispersed in mineral oil, 17 mg, 0.43 mmol) in THF (0.18 mL) was added a solution of 3-methoxythiophenol (51 µL, 0.41 mmol) in THF (0.13 mL) at 0° C. After 5 minutes, a solution of N-(4-Cyano-3-trifluorophenyl)methacrylamide epoxide (88 mg, 0.33 mmol) in THF (0.45 mL) was added slowly. The reaction was allowed to warm to room temperature and stirred overnight. The solvent was evaporated. The residue was diluted with water and extracted with ethyl acetate (50 mL). The organic layer was washed with water (25 mL) and brine (25 mL), dried over magnesium sulfate, filtered and evaporated. Purification by column chromatography (hexane:EtOAc 50:50) yielded 55 mg of desired product. Production of 3-(3-methoxyphenylthio)-N-(4-Cyano-3-(trifluoromethyl)phenyl)-2-hydroxy-2-methylpropanamide was confirmed by 1-H NMR and mass spectral analysis.

Example 17

3-(3-methoxyphenylsulfonyl)-N-(4-Cyano-3-(trifluoromethyl)phenyl)-2-hydroxy-2-methylpropanamide, (PLM5)

To a solution of 3-(3-methoxyphenylthio)-N-(4-Cyano-3-(trifluoromethyl)phenyl)-2-hydroxy-2-methylpropanamide (29 mg, 0.07 mmol) in dichloromethane (0.18 mL) at −78° C. was added 30% hydrogen peroxide (16 µL, 0.57 mmol) followed by the slow addition of trifluoroacetic anhydride (60 µL, 0.45 mmol). The reaction was stirred at room temperature for 16 h. The reaction was diluted with dichloromethane. Cold water and brine were added, and the reaction was stirred for 20 minutes. The organic layer was separated, dried over magnesium sulfate, filtered and evaporated. Purification by column chromatography (hexane:EtOAc 50:50) yielded 19 mg of desired product. Production of PLM5 was confirmed by 1-H NMR, 13-C NMR, and mass spectral analysis.

Example 18

S-2-phenylphenyl-O-ethyl carbonodithioate

To a solution of 2-aminobiphenyl (250 mg, 1.47 mmol) in water (3.9 mL) at 0° C. was added concentrated hydrochloric acid (0.2 mL). A solution of sodium nitrite (102 mg, 1.47 mmol) in water (0.8 mL) at 0° C. was added, and the mixture was stirred for 30 minutes. This solution was then added to a solution of potassium ethyl xanthate (284 mg, 1.8 mmol) in water (0.36 mL) at 45° C. The reaction mixture was stirred for an additional 30 minutes. Diethyl ether (25 mL) was added, and the organic layer was washed with 10% sodium hydroxide solution followed by water until neutral. The organic layer was dried over magnesium sulfate, filtered and evaporated. The crude product was used directly in Example 19.

Example 19

2-phenylbenzenethiol

To a refluxing solution of S-2-benzylphenyl-O-ethyl carbonodithioate (405 mg, 1.47 mmol) in ethanol (4.5 mL) was added slowly potassium hydroxide pellets (354 mg, 6.3 mmol). After refluxing overnight, the solvent was evaporated. The residue was diluted with water (10 mL) and extracted with diethyl ether (10 mL). The aqueous layer was acidified with 2 N HCl and washed with diethyl ether. The organic layer was separated, dried over magnesium sulfate, filtered and evaporated to yield 105 mg of the crude thiol that was used directly in Example 20.

Example 20

3-(1-phenylphenylthio)-N-(4-Cyano-3-(trifluoromethyl)phenyl)-2-hydroxy-2-methylpropanamide To a stirred suspension of sodium hydride (60% dispersed in mineral oil, 12 mg, 0.31 mmol) in THF (0.1 mL) was added a solution of 2-phenylbenzenethiol (38 mg, 0.3 mmol) in THF (0.1 mL) at 0° C. After 5 minutes, a solution of N-(4-Cyano-3-trifluorophenyl)methacrylamide epoxide (64 mg, 0.24 mmol) in THF (0.33 mL) was added slowly. The reaction was allowed to warm to room temperature and stirred overnight. The solvent was evaporated. The residue was diluted with water and extracted with ethyl acetate (50 mL). The organic layer was washed with water (25 mL) and brine (25 mL), dried over magnesium sulfate, filtered and evaporated. Purification by column chromatography (hexane:EtOAc 50:50) yielded 85 mg of desired product.

Example 21

3-(1-phenylphenylsulfonyl)-N-(4-Cyano-3-(trifluoromethyl)phenyl)-2-hydroxy-2-methylpropanamide, (PLM54)

To a solution of 3-(1-phenylphenylthio)-N-(4-Cyano-3-(trifluoromethyl)phenyl)-2-hydroxy-2-methylpropanamide (85 mg, 0.21 mmol) in dichloromethane (0.3 mL) at −78° C. was added 30% hydrogen peroxide (0.036 mL, 1.26 mmol) followed by the slow addition of trifluoroacetic anhydride (0.151 mL, 1.07 mmol). The reaction was stirred at room temperature for 16 h. The reaction was diluted with dichloromethane. Cold water and brine were added, and the reaction was stirred for 20 minutes. The organic layer was separated, dried over magnesium sulfate, filtered and evaporated. Purification by column chromatography (hexane:EtOAc 50:50) yielded 41 mg of desired product.

Example 22

N-(4-Cyano-3-(trifluoromethyl)phenyl)-2-hydroxy-2-methyl-3-(naphthalen-2-ylthio)propanamide To a stirred suspension of sodium hydride (60% dispersed in mineral oil, 26 mg, 0.65 mmol) in THF (0.27 mL) was added a solution of 2-naphthalenethiol (100 mg, 0.62 mmol) in THF (0.2 mL) at 0° C. After 5 minutes, a solution of N-(4-Cyano-3-trifluorophenyl)methacrylamide epoxide (134 mg, 0.50 mmol) in THF (0.7 mL) was added slowly. The reaction was allowed to warm to room temperature and stirred overnight. The solvent was evaporated. The residue was diluted with water and extracted with ethyl acetate (50 mL). The organic layer was washed with water (25 mL) and brine (25 mL), dried over magnesium sulfate, filtered and evaporated. Purification by column chromatography (hexane:EtOAc 50:50) yielded 63 mg of desired product. Production of N-(4-Cyano-3-(trifluoromethyl)phenyl)-2-hydroxy-2-methyl-3-(naphthalen-2-ylthio)propanamide was confirmed by 1-H NMR and 13-C NMR.

Example 23

N-(4-Cyano-3-(trifluoromethyl)phenyl)-2-hydroxy-2-methyl-3-(naphthalen-2-ylsulfonyl)propanamide, (PLM55)

To a solution of N-(4-Cyano-3-(trifluoromethyl)phenyl)-2-hydroxy-2-methyl-3-(naphthalen-3-ylsulfonyl)propanamide (63 mg, 0.15 mmol) in dichloromethane (0.4 mL) and at −78° C. was added 30% hydrogen peroxide (25 µL, 0.88 mmol) followed by the slow addition of trifluoroacetic anhydride (0.1 mL, 0.74 mmol). The reaction was stirred at room temperature for 16 h and then diluted with dichloromethane. Cold water and brine were added, and the reaction was stirred for 20 minutes. The organic layer was separated, dried over magnesium sulfate, filtered and evaporated. Purification by column chromatography (hexane:EtOAc 50:50) yielded 22 mg of desired product.

Example 24

S-1-bromonaphthalen-4-yl-O-ethyl carbonodithioate

To a solution of 1-amino-4-bromonaphthalene (150 mg, 0.68 mmol) in water (1.8 mL) at 0° C. was added concentrated hydrochloric acid (0.1 mL). A solution of sodium nitrite (47 mg, 0.68 mmol) in water (0.36 mL) at 0° C. was added, and the mixture was stirred for 30 minutes. This solution was then added to a solution of potassium ethyl xanthate (130 mg, 0.81 mmol) in water (0.16 mL) at 45° C. The reaction mixture was stirred for an additional 30 minutes. Diethyl ether (25 mL) was added, and the organic layer was washed with 10% sodium hydroxide solution followed by water until neutral. The organic layer was dried over magnesium sulfate, filtered and evaporated. The crude product was used directly in Example 25.

Example 25

4-bromonaphthalene-1-thiol

To a refluxing solution of S-1-bromonaphthalen-4-yl-O-ethyl carbonodithioate (188 mg, 0.57 mmol) in ethanol (1.7 mL) was added slowly potassium hydroxide pellets (138 mg, 2.4 mmol). After refluxing overnight, the solvent was evaporated. The residue was diluted with water (10 mL) and extracted with diethyl ether (10 mL). The aqueous layer was acidified with 2 N HCl and washed with diethyl ether. The organic layer was separated, dried over magnesium sulfate, filtered and evaporated to yield 75 mg of the crude thiol that was used directly in Example 26.

Example 26

3-(1-bromonaphthalen-4-ylthio)-N-(4-Cyano-3-(trifluoromethyl)phenyl)-2-hydroxy-2-methylpropanamide To a stirred suspension of sodium hydride (60% dispersed in mineral oil, 2.8 mg, 0.07 mmol) in THF (0.03 mL) was added a solution of 4-bromonaphthalene-1-thiol (16 mg, 0.07 mmol) in THF (0.2 mL) at 0° C. The mixture was stirred for 5 minutes before a solution of N-(4-Cyano-3-trifluorophenyl) methacrylamide epoxide (14 mg, 0.05 mmol) dissolved in THF (0.07 mL) was added slowly. The reaction was allowed to warm to room temperature and stirred overnight. The solvent was evaporated. The mixture was diluted with water and extracted with ethyl acetate (50 mL). The organic layer was washed with water (25 mL) and brine (25 mL), dried over magnesium sulfate, filtered and evaporated. Purification by column chromatography (hexane:EtOAc 50:50) yielded 13 mg of desired product.

Example 27

3-(1-bromonaphthalen-4-ylsulfonyl)-N-(4-Cyano-3-(trifluoromethyl)phenyl)-2-hydroxy-2-methylpropanamide, (PLM9)

To a solution of 3-(1-bromonaphthalen-4-ylthio)-N-(4-Cyano-3-(trifluoromethyl)phenyl)-2-hydroxy-2-methylpropanamide (13 mg, 0.025 mmol) in dichloromethane (0.06 mL) at −78° C. was added 30% hydrogen peroxide (4.4 µL, 0.155 mmol) followed by the slow addition of trifluoroacetic anhydride (18 µL, 0.13 mmol). The reaction was stirred at room temperature for 16 h before the reaction was diluted with dichloromethane. Cold water and brine were added, and the reaction was stirred for 20 minutes. The organic layer was separated, dried over magnesium sulfate, filtered and evaporated. Purification by column chromatography (hexane:EtOAc 50:50) yielded 9 mg of desired product.

Example 28

N-(4-Cyano-3-(trifluoromethyl)phenyl)-2-hydroxy-3-((1-(3-hydroxypropyl)naphthalene-4-yl)sulfonyl)-2-methylpropanamide (PLM14)

The precursor 3-(1-aminonaphthalen-4-yl)propan-1-ol was first prepared as follows: To a 0° C. solution of 4-allyl-naphthalen-1-amine (1830 mg, 9.73 mmol), (derived from palladium catalyzed allylation of 1-amino bromonapthalene with allyl tributyl tin) in 19 mL of THF was added 1 M BH$_3$ (14.6 mL, 14.6 mMol). The reaction mixture was stirred at 0° C. for 30 min, warmed to room temperature and stirred for an additional 2 h. The reaction mixture was cooled to 0° C. and 3M NaOH (3.6 mL) and 30% H$_2$O$_2$ (1.14 mL) were added. The reaction mixture was stirred for 30 min at 0° C. and then heated to 60° C. and stirred for an additional 1 h. The solvent was evaporated under reduced pressure and the resulting residue was diluted with water and extracted with EtOAc (2×40 mL). The combined organic extracts were washed with water (50 mL) and brine (50 mL), dried over MgSO$_4$, filtered and evaporated under reduced pressure. The product was purified by flash column chromatography on silica gel (5% EtOAC→70% EtOAc/Hexanes) to yield 5 (1040 mg, 52%) as a colorless oil. HRMS (CI) calculated for [C$_{13}$H$_{15}$NO+H] 202.1232, found 202.1228. $^1$H NMR (CDCl$_3$, 400 MHz): δ 8.03 (d, J=8.0 Hz, 1H), 7.87 (d, J=7.2 Hz, 1H), 7.54-7.45 (m, 2H), 7.14 (d, J=7.6 Hz, 1H), 6.71 (d, J=7.6 Hz, 1H), 4.07 (bs, 2H), 3.70, (t, J=6.4 Hz, 2H), 3.05 (t, J=7.6 Hz, 2H), 2.14 (bs, OH), 1.96 (p, J=6.4 Hz, 2H). $^{13}$C NMR (CDCl$_3$, 400 MHz): δ 140.4, 132.3, 128.5, 126.2, 125.6, 124.4, 124.4, 124.2, 121.4, 109.6, 62.3, 33.5, 28.7.

3-(1-aminonaphthalen-4-yl)propan-1-ol was then converted to 3-(1-mercaptonaphthalen-4-yl)propan-1-ol by diazotization followed by substitution with ethylxanthate and subsequent hydrolysis as following the general procedure described in Examples 12 and 13.

To a stirred suspension of 1.31 equiv. of sodium hydride (60% dispersed in mineral oil) in THF at 0° C. was added a solution of 1.26 equiv. of 3-(1-mercaptonaphthalen-4-yl)propan-1-ol dissolved in THF and stirred for 5 minutes. A solution of 1 equiv. of N-(4-Cyano-3-trifluorophenyl)methacrylamide epoxide in THF was added to the reaction mixture. The reaction was allowed to warm to room temperature and stir overnight. The solvent was evaporated. The residue was diluted with water and extracted with EtOAc (3×50 mL). The organic extracts were washed with water, brine, dried over MgSO$_4$, filtered and evaporated under reduced pressure. The resulting crude product was purified by flash column chromatography on silica gel (50% EtOAc/Hexane) to yield (42%) of N-(4-cyano-3-(trifluoromethyl)phenyl)-2-hydroxy-3-((1-(3-hydroxypropyl) naphthalene-4-yl)sulfanyl)-2-methylpropanamide as a colorless oil.

PLM14 was made from the oxidation of N-(4-Cyano-3-(trifluoromethyl)phenyl)-2-hydroxy-3-((1-(3-hydroxypropyl)naphthalene-4-yl)sulfanyl)-2-methylpropanamide following the general procedure for PLM1 to give 11 mg (44%) of desired product as a white solid. HRMS (ESI) calculated for [C$_{25}$H$_{23}$F$_3$N$_2$O$_5$S+Na] 543.1178, found 543.1179. $^1$H NMR (CDCl$_3$, 400 MHz): δ 9.24 (bs, NH), 8.71 (d, J=8.4 Hz, 1H), 8.17-8.12 (m, 2H), 7.97 (s, 1H), 7.81-7.70 (m, 4H), 7.32 (d, J=7.6 Hz, 1H), 5.23 (s, OH), 4.42 (t, J=6.4 Hz, 2H), 4.24 (d, J=14.4 Hz, 1H), 3.64 (d, J=14.4 Hz, 1H), 3.22 (dp, J=42.4, 7.6 Hz, 2H), 2.18 (p, J=6.4 Hz, 2H), 1.59 (s, 3H). $^{13}$C NMR (CDCl$_3$, 400 MHz): δ 171.6, 145.6, 141.3, 135.6, 132.8, 132.3, 130.1, 129.0, 128.9, 127.6, 124.6, 124.4, 124.3, 123.4, 121.9, 120.7, 117.2, 115.4, 104.5, 74.6, 67.0, 61.1, 29.3, 28.6, 27.7.

Example 29

N-(4-Cyano-3-(trifluoromethyl)phenyl)-2-hydroxy-3-((1-(3-hydroxypropyl)naphthalene-5-yl)sulfonyl)-2-methylpropanamide (PLM15)

The precursor N-(4-Cyano-3-(trifluoromethyl)phenyl)-2-hydroxy-3-((1-(3-hydroxypropyl)naphthalene-5-yl)sulfanyl)-2-methylpropanamide was prepared as follows: To a solution of 1.31 equiv. of sodium hydride (60% dispersed in mineral oil) in THF at 0° C. was added a solution of 1.26 equiv. of 3-(1-mercaptonaphthalen-5-yl)propan-1-ol (prepared analogously to 3-(1-aminonaphthalen-4-yl)propan-1-ol in example 28) dissolved in THF (0.2 mL) and stirred for 5 minutes. A solution of 1 equiv. of N-(4-Cyano-3-trifluorophenyl)methacrylamide epoxide (50 mg, 0.185 mmol) in THF (0.7 ml) was added to the reaction mixture. The reaction was allowed to warm to room temperature and stir overnight. Standard workup afforded the desired product in 37% yield. HRMS (ESI) calculated for [C$_{25}$H$_{23}$F$_3$N$_2$O$_3$S+Na] 511.1279, found 511.1278. $^1$H NMR (CDCl$_3$, 400 MHz): δ 8.99 (bs, NH), 8.30 (d, J=8.8 Hz, 1H), 7.85 (d, J=8.4 Hz, 1H), 7.72 (s, 1H), 7.68 (d, J=7.2 Hz, 1H), 7.57 (d, J=8.4 Hz, 1H), 7.50 (d, J=8.4 Hz, 1H), 7.39 (t, J=7.6 Hz, 1H), 7.30-7.26 (m, 2H), 4.14 (s, OH), 3.85 (d, J=13.6 Hz, 1H), 3.70 (t, J=6.4 Hz, 2H), 3.18 (d, J=14.4 Hz, 1H), 3.01 (sent, J=8.0 Hz, 2H), 2.14 (bs, OH), 1.90 (p, J=2.8 Hz, 2H), 1.52 (s, 3H). $^{13}$C NMR (CDCl$_3$, 400 MHz): δ 173.1, 141.0, 138.8, 135.3, 133.6, 132.2, 131.5, 130.6, 126.4, 126.3, 125.2, 124.2, 123.3, 123.3, 121.3, 120.6, 116.8, 115.6, 103.7, 75.3, 62.1, 45.4, 33.2, 29.1, 26.1.

PLM15 was made from the oxidation of N-(4-Cyano-3-(trifluoromethyl)phenyl)-2-hydroxy-3-((1-(3-hydroxypropyl)naphthalene-5-yl)sulfanyl)-2-methylpropanamide following the general procedure for PLM1 to give 42 mg (40%) of desired product as a white solid. HRMS (ESI) calculated for [C$_{25}$H$_{23}$F$_3$N$_2$O$_5$S+Na] 543.1178, found 543.1186. $^1$H NMR (CDCl$_3$, 400 MHz): δ 9.15 (bs, NH), 8.59 (d, J=8.4 Hz, 1H), 8.29 (d, J=8.4 Hz, 1H), 8.23 (d, J=7.2 Hz, 1H), 7.93 (s, 1H), 7.79-7.70 (m, 3H), 7.53 (d, J=7.2 Hz, 1H), 7.47 (t, J=8.0 Hz, 1H), 5.29 (s, OH), 4.44 (t, J=6.4 Hz, 2H), 4.24 (d, J=14.4 Hz, 1H), 3.64 (d, J=14.4 Hz, 1H), 3.25 (t, J=7.2 Hz, 2H), 2.21 (p, J=6.8 Hz, 2H), 1.59 (s, 3H). $^{13}$C NMR (CDCl$_3$, 400 MHz): δ 173.4, 141.1, 138.1, 135.7, 134.8, 132.5, 131.2, 130.0, 129.3, 129.0, 127.9, 124.2, 123.3, 122.4, 121.8, 120.7, 117.3, 115.4, 104.9, 74.6, 67.1, 60.8, 29.2, 29.1, 27.7.

Example 30

(E)-methyl 3-(1-(2-(4-Cyano-3-(trifluoromethyl) phenylcarbamoyl)-2-hydroxypropylsulfonyl)naphthalene-4-yl)acrylate (PLM16)

The precursor 1-amino-4-bromonaphthalene was converted to 1-thiol-4-bromonaphthalene by diazotization followed by substitution with ethylxanthate and subsequent hydrolysis following the general proceedure described in Examples 12 and 13.

The precursor (E)-methyl 3-(1-(2-(4-Cyano-3-(trifluoromethyl)phenylcarbamoyl)-2-hydroxypropylthio)naphthalene-4-yl)acrylate was prepared as follows: To a solution of 1-thiol-4-bromonaphthalene (40 mg, 0.079 mmol), triphenylphosphine (3.4 mg, 0.013 mmol), palladium (II) acetate (1 mg, 0.0044 mmol) and triethylamine (36 μL, 0.26 mmol) in 0.5 mL DMF was added methyl acrylate (9.2 μL, 0.1 mmol). The reaction was heated to 90° C. overnight. The reaction mixture was cooled to room temperature, diluted with water (10 mL) and extracted with EtOAc (2×10 mL). The combined organic extracts were washed with water (10 mL) and brine (10 mL), dried over MgSO$_4$, filtered and evaporated. The resulting crude product was purified by flash column chromatography on silica gel (10%→50% EtOAc/Hexanes) to yield 21 mg (53%) of desired product as a brown oil. HRMS (ESI) calculated for [C$_{26}$H$_{21}$F$_3$N$_2$O$_4$S+Na] 537.1072, found 537.1072. $^1$H NMR (CDCl$_3$, 400 MHz): δ 8.83 (bs, NH), 8.44 (d, J=8.0 Hz, 1H), 8.30 (d, J=15.6 Hz, 1H), 8.06 (d, J=7.6 Hz, 1H), 7.70-7.50 (m, 7H), 6.33 (d, J=15.6 Hz, 1H), 3.94 (d, J=14.0 Hz, 1H), 3.87 (s, 3H), 3.22 (d, J=14.0 Hz, 1H), 2.45 (s, OH), 1.55 (s, 3H). ¹³C NMR (CDCl₃, 400 MHz): δ 172.8, 166.9, 140.9, 140.6, 135.5, 133.5, 133.2, 132.1, 131.6, 130.0, 127.2, 127.1, 125.3, 124.2, 124.2, 123.3, 121.2, 121.0, 120.6, 116.7, 115.3, 104.3, 75.3, 51.9, 44.9, 26.3.

PLM16 was made from the oxidation of (E)-methyl 3-(1-(2-(4-Cyano-3-(trifluoromethyl)phenylcarbamoyl)-2-hydroxypropylthio)naphthalene-4-yl)acrylate following the general procedure for PLM1 to give 14 mg (64%) of desired product as a brown oil. HRMS (ESI) calculated for [C₂₆H₂₁F₃N₂O₆S+Na] 569.0970, found 569.0990. ¹H NMR (CDCl₃, 400 MHz): δ 9.02 (bs, NH), 8.73 (d, J=8.4 Hz, 1H), 8.40 (d, 15.6 Hz, 1H), 8.29 (d, J=8.4 Hz, 1H), 8.24 (d, J=8.0 Hz, 1H), 7.89-7.77 (m, 4H), 7.67 (d, J=8.4 Hz, 1H), 7.59 (d, J=8.0 Hz, 1H), 6.37 (d, J=15.6 Hz, 1H), 5.25 (s, OH), 4.29 (d, J=14.4 Hz, 1H), 3.92 (s, 3H), 3.63 (d, J=15.6 Hz, 1H), 1.60 (s, 3H). ¹³C NMR (CDCl₃, 400 MHz): δ 171.1, 161.1, 140.9, 140.0, 139.9, 135.7, 134.6, 132.0, 129.8, 129.6, 129.0, 128.2, 125.1, 124.5, 124.1, 123.3, 122.7, 121.6, 120.6, 117.0, 115.2, 105.1, 74.4, 60.6, 52.2, 27.9.

Example 31

(E)-methyl 3-(1-(2-(4-Cyano-3-(trifluoromethyl) phenylcarbamoyl)-2-hydroxypropylsulfonyl)naphthalene-5-yl)acrylate (PLM18)

The precursor 3-(1-bromonaphthalen-5-ylthio)-N-(4-Cyano-3-(trifluoromethyl)phenyl)-2-hydroxy-2-methylpropanamide) was prepared as follows: To a suspension of 1.31 equiv. of sodium hydride (60% dispersed in mineral oil) in THF at 0° C. was added a solution of 1.26 equiv. of 5-bromonaphthalen-1-thiol dissolved in THF and stirred for 5 minutes. A solution of 1 equiv. of N-(4-Cyano-3-trifluorophenyl) methacrylamide epoxide in THF was added to the reaction mixture. The reaction was allowed to warm to room temperature and was stirred overnight. Standard workup followed by chromatography afforded (29 mg, (71%) 3-(1-bromonaphthalen-5-ylthio)-N-(4-cyano-3-(trifluoromethyl)phenyl)-2-hydroxy-2-methylpropanamide), as a brown oil. HRMS (ESI) calculated for [C₂₂H₁₆BrF₃N₂O₂S+Na] 530.9966, found 530.9981. ¹H NMR (CDCl₃, 400 MHz): δ 8.78 (bs, NH), 8.30 (d, J=8.4 Hz, 1H), 8.03 (d, J=7.6 Hz, 1H), 7.77 (d, J=7.2 Hz, 1H), 7.69 (d, J=7.2 Hz, 1H), 7.60-7.52 (m, 2H), 7.42-7.32 (m, 3H), 3.92 (d, J=14.0 Hz, 1H), 3.71 (s, OH), 3.15 (d, J=14.4 Hz, 1H), 1.52 (s, 3H). ¹³C NMR (d6-Acetone, 400 MHz): δ 174.7, 134.5, 136.7, 135.2, 135.0, 132.9, 131.4, 131.2, 127.9, 127.5, 126.8, 126.1, 124.9, 123.5, 122.9, 122.1, 117.9, 116.3, 104.0, 76.5, 46.1, 26.5.

The precursor (E)-methyl 3-(1-(2-(4-Cyano-3-(trifluoromethyl)phenylcarbamoyl)-2-hydroxypropylthio)naphthalene-5-yl)acrylate was prepared as follows: To a solution of 3-(1-bromonaphthalen-5-ylthio)-N-(4-Cyano-3-(trifluoromethyl)phenyl)-2-hydroxy-2-methylpropanamide), triphenylphosphine, palladium (II) acetate and triethylamine in DMF was added methyl acrylate. The reaction was heated to 90° C. overnight. The reaction mixture was cooled to room temperature, diluted with water and extracted with EtOAc. The combined organic extracts were washed with water and brine, dried over MgSO₄, filtered and evaporated. The resulting crude product was purified by flash column chromatography on silica gel (10%→50% EtOAc/Hexanes) to yield 21 mg (51%) of desired product as a brown oil. HRMS (ESI) calculated for [C₂₆H₂₁F₃N₂O₄S+Na] 537.1072, found 537.1098. ¹H NMR (CDCl₃, 400 MHz): δ 8.83 (bs, NH), 8.50 (d, J=8.0 Hz, 1H), 8.34 (d, J=15.6 Hz, 1H), 8.00 (d, J=8.4 Hz, 1H), 7.78 (d, J=6.8 Hz, 1H), 7.67-7.61 (m, 3H), 7.53 (t, J=8.0 Hz, 2H), 7.39 (t, J=8.0 Hz, 1H), 6.45 (d, J=15.6 Hz, 1H), 3.90 (d, J=14.0 Hz, 1H), 3.87 (s, 3H), 3.69 (s, OH), 3.19 (d, J=14.0 Hz, 1H), 1.53 (s, 3H). ¹³C NMR (CDCl₃, 400 MHz): δ 172.7, 166.9, 141.0, 140.8, 135.4, 133.6, 132.7, 131.9, 131.8, 131.5, 127.0, 126.4, 126.2, 125.3, 124.2, 123.3, 121.3, 121.2, 120.6, 116.7, 115.3, 104.3, 52.0, 45.6, 26.2.

PLM18 was made from the oxidation of (E)-methyl 3-(1-(2-(4-Cyano-3-(trifluoromethyl)phenylcarbamoyl)-2-hydroxypropylthio)naphthalene-5-yl)acrylate following the general procedure for PLM1 to give 25 mg (54%) of desired product as a brown oil. HRMS (ESI) calculated for [C₂₆H₂₁F₃N₂O₆S+Na] 569.0970, found 569.0989. ¹H NMR (CDCl₃, 400 MHz): δ 9.06 (bs, NH), 8.73 (d, J=8.8 Hz, 1H), 8.46 (s, 1H), 8.44 (d, J=15.6 Hz, 1H), 8.27 (d, J=7.2 Hz, 1H), 7.89-7.70 (m, 5H), 7.52 (t, J=8.0 Hz, 1H), 6.72 (d, J=15.6 Hz, 1H), 5.19 (bs, OH), 4.22 (d, J=14.4 Hz, 1H), 3.89 (s, 3H), 3.63 (d, J=14.4 Hz, 1H), 1.59 (s, 3H). ¹³C NMR (CDCl₃, 400 MHz): δ 171.3, 166.7, 140.9, 140.7, 135.8, 134.7, 133.7, 132.1, 131.5, 130.6, 129.4, 129.0, 126.4, 125.3, 124.9, 123.3, 122.8, 121.8, 120.7, 117.2, 115.3, 105.1, 74.6, 60.9, 52.0, 27.7.

Example 32

(2-bromophenyl)(2,4,6-trimethoxybenzyl)sulfane

To a solution of 30.8 g (2,4,6-trimethoxyphenyl)methanol (155.4 mmol) and 29.2 g 2-bromobenzenethiol (155.4 mmol) in 150 ml DCM at 0° C. was added dropwise 1.3 eq TFA. The reaction was stirred 15 minutes at room temperature before saturated NaHCO₃ was added until neutral. The organic volatiles were removed under reduced pressure and the aqueous residue was extracted with ethyl acetate (3×150 ml). The organic layer was collected, washed with brine and dried over magnesium sulfate, filtered, and concentrated under reduced pressure afforded a yellowish solid. The solid was washed with ethyl acetate to yield 51.3 g white solid (2-bromophenyl) (2,4,6-trimethoxybenzyl)sulfane (13.9 mmol, 89% yield).

Example 33

2-(2,4,6-trimethoxybenzylthio)phenylboronic Acid

To a solution of 4.22 g (2-bromophenyl)(2,4,6-trimethoxybenzyl)sulfane (11.56 mmol) in 150 ml dry THF at –78° C. was added slowly 5.6 ml 2.5M n-BuLi. The solution was stirred at –78° C. for 25 minutes. 1.6 ml B(OMe)₃ was added at –78° C. The reaction was stirred 2 hours at RT. 100 ml water was added, stirred overnight. The mixture was extracted with ethyl acetate (2×100 ml). The organic layer was washed with brine, dried over magnesium sulfate, filtered and concentrated. Purification by gradient chromatography (hexane: ethyl acetate 60:40) yielded 1.762 g product (5.3 mmol, 46% yield).

Example 34

2'-(2,4,6-trimethoxybenzylthio)biphenyl-3-ol

To a mixture of 1.05 g 2-(2,4,6-trimethoxybenzylthio)phenylboronic acid (3.14 mmol), 1.07 g 3-iodophenol (4.9 mmol) and 0.195 g Pd catalyst was added 40 ml toluene followed by 15 ml 2M Na₂CO₃. The mixture was refluxed under nitrogen overnight. The mixture was extracted with ethyl acetate. The organic was washed with water, brine, dried over magnesium sulfate, and concentrated. The residue was purified by silica flash chromatography (hexane:ethyl acetate 80:20) to afford 0.948 g product (2.48 mmol, 79% yield).

Example 35

2'-mercaptobiphenyl-3-ol

2'-(2,4,6-trimethoxybenzylthio)biphenyl-3-ol (0.948 g, 2.48 mmol) was treated with TFA:triethylsilane:DCM (8 ml:3 ml:80 ml). The solution was stirred 30 min. before 40 ml water was added and the mixture was extracted with DCM (2×80 ml). The organic was washed with water, brine, dried over magnesium sulfate and concentrated. The residue was purified by silica flash chromatography (hexane:ethyl acetate 80:20) to afford 0.335 g product (1.66 mmol, 67% yield).

Example 36

N-(4-Cyano-3-(trifluoromethyl)phenyl)-2-hydroxy-3-(2'-hydroxybiphenyl-2-ylsulfonyl)-2-methylpropanamide (PAN41)

Figure 11:
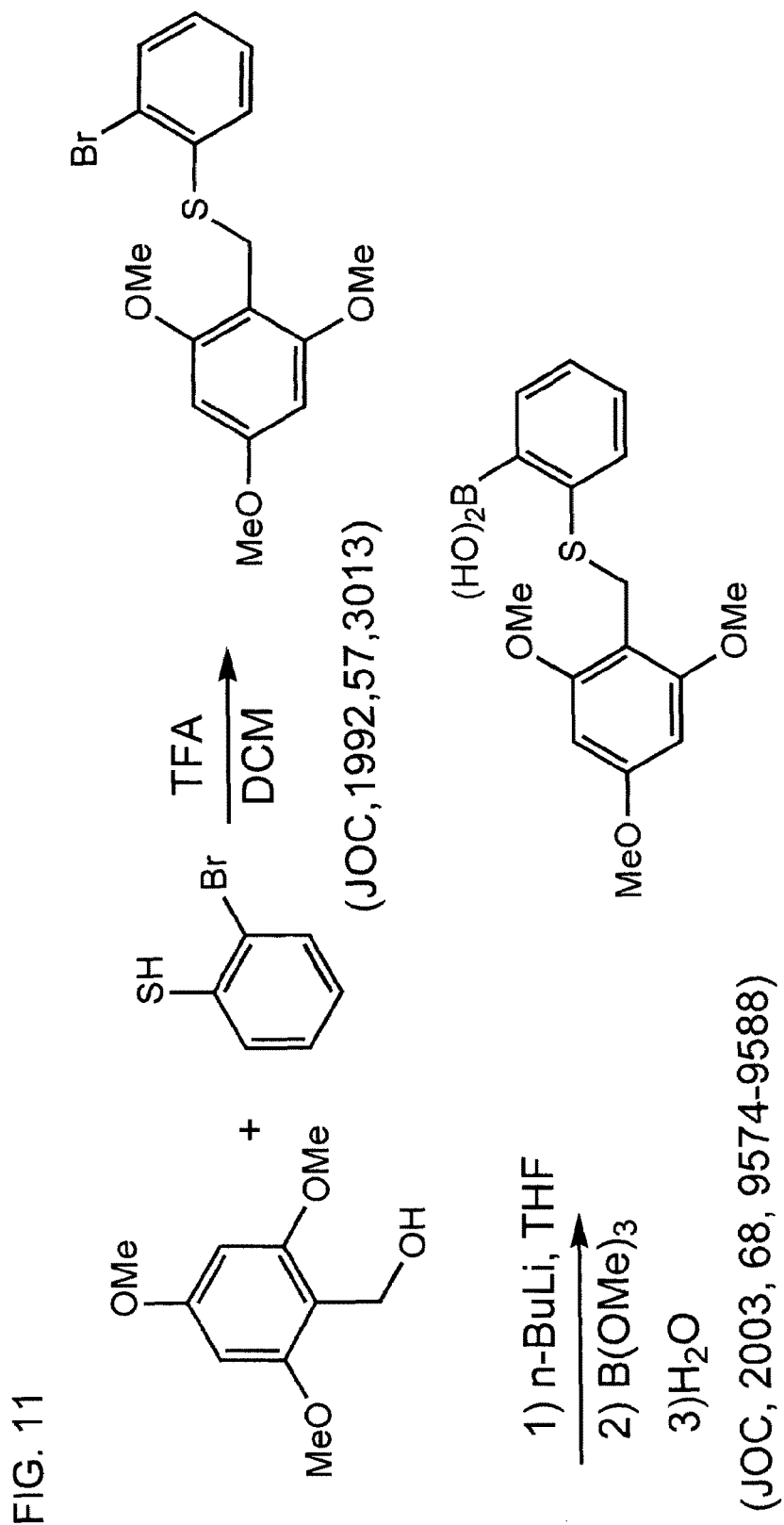
FIG. 11. Synthetic scheme for construction of precursors for PAN41, PAN51, PAN61.
Figure 12:
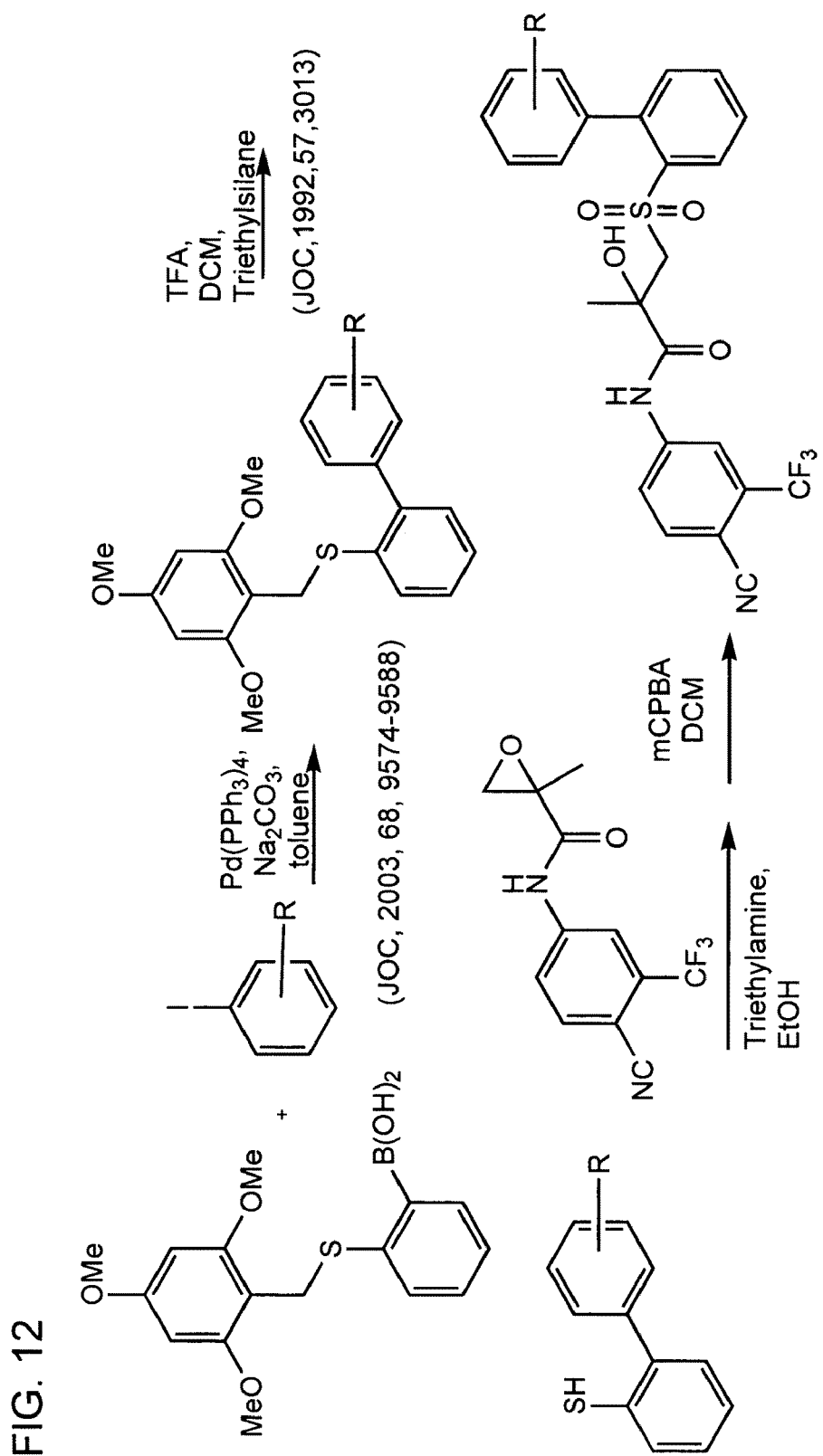
FIG. 12. General strategy for synthesis of PAN41, PAN51, PAN61.

To a solution of 0.335 g 2'-mercaptobiphenyl-3-ol (1.66 mmol), 0.432 g N-(4-cyano-3-(trifluoromethyl)phenyl)-2-methyloxirane-2-Carboxamide (1.59 mmol) in 4 ml ethanol was added 0.6 ml triethylamine. The mixture was stirred overnight at ambient temperature before concentrating under reduced pressure. The residue was dissolved in ethyl acetate, washed with water, brine, dried over magnesium sulfate and concentrated. A solution of the unrefined product in 10 mL of DCM was treated with 0.77 g mCPBA (3.1 mmol). The mixture was stirred overnight and concentrated. The residue was dissolved in ethyl acetate, washed with water, brine, dried over magnesium sulfate and concentrated. Purification by flash chromatography (hexane:ethyl acetate 50:50) to afford 0.389 g product (0.77 mmol, 46% yield for two steps). Production of PAN41 was confirmed by 1-H NMR and 13-C NMR. See FIG. 11 for general synthesis scheme for precursors of PAN41, PAN51, and PAN61. See FIG. 12 for the general PAN41, PAN51, and PAN61 synthesis strategy. Production of both PAN51 and PAN61 was confirmed by 1-H NMR and 13-C NMR.

Example 37

(2-methoxyphenyl)(2-(methylthio)phenyl)methanone (G)

To a solution of 5.4 g 2-bromoanisole in 200 ml THF at −78° C. was added dropwise 1.2 eq of n-BuLi. 1.2 eq of N-methoxy-N-methyl-2-(methylthio)benzamide in THF was added and the reaction was warmed to RT and stirred for an additional 1 h. Water (100 ml) was added, and the mixture was extracted with ethyl acetate. The combined organic extracts were washed with brine, dried over magnesium sulfate and concentrated. Silica flash chromatography (hexane:ethyl acetate 80:20) afforded 7.2 g of a pale yellow solid product (27.9 mmol, 96% yield).

Example 38

(2-hydroxyphenyl)(2-(methylthio)phenyl)methanone (H)

To a mixture of 1.45 g (2-methoxyphenyl)(2-(methylthio)phenyl)methanone (G) and 1.437 g AlCl$_3$ was added slowly 5 mL 1-dodecanethiol. The reaction was stirred overnight before 30 ml water was added. The mixture was extracted with ethyl acetate and the combined organic extracts were washed with brine, dried over magnesium sulfate, and the volatiles removed by distillation under nitrogen. Flash silica chromatography (hexane:ethyl acetate 80:20) afforded 0.807 g product (3.31 mmol, 60% yield).

Example 39

2-(2-(methylthio)benzyl)phenol (I)

To a mixture of 0.337 g (2-hydroxyphenyl)(2-(methylthio)phenyl)methanone (H) (1.38 mmol) and 0.5 ml triethylsilane was added 2 ml TFA. After 1 h, water was added and the mixture was extracted with ethyl acetate. The combined organic extracts were dried over magnesium sulfate, and concentrated. Flash silica chromatography (hexane:ethyl acetate 80:20) afforded 0.235 g product (1.02 mmol, 74% yield).

Example 40

2-(2-mercaptobenzyl)phenol (J)

To a solution of 0.68 g 2-(2-(methylthio)benzyl)phenol (I) (2.96 mmol) in 4 ml freshly distilled THF at −78° C. was added 8 mL condensed ammonia followed by 0.15 g sodium. The blue solution was stirred for 2 hours at −78° C. before the mixture was warmed to ambient temperature. The reaction was allowed to stir overnight before NH$_4$Cl was added until neutral. The mixture was extracted with ethyl acetate and the combined organic extracts washed with brine, dried over magnesium sulfate and concentrated. Flash silica chromatography (hexane:ethyl acetate 80:20) afforded 0.457 g product (2.12 mmol, 71% yield).

Example 41

N-(4-Cyano-3-(trifluoromethyl)phenyl)-2-hydroxy-3-(2-(2-hydroxybenzyl)phenylsulfonyl)-2-methylpropanamide, (PAN11)

Figure 13:
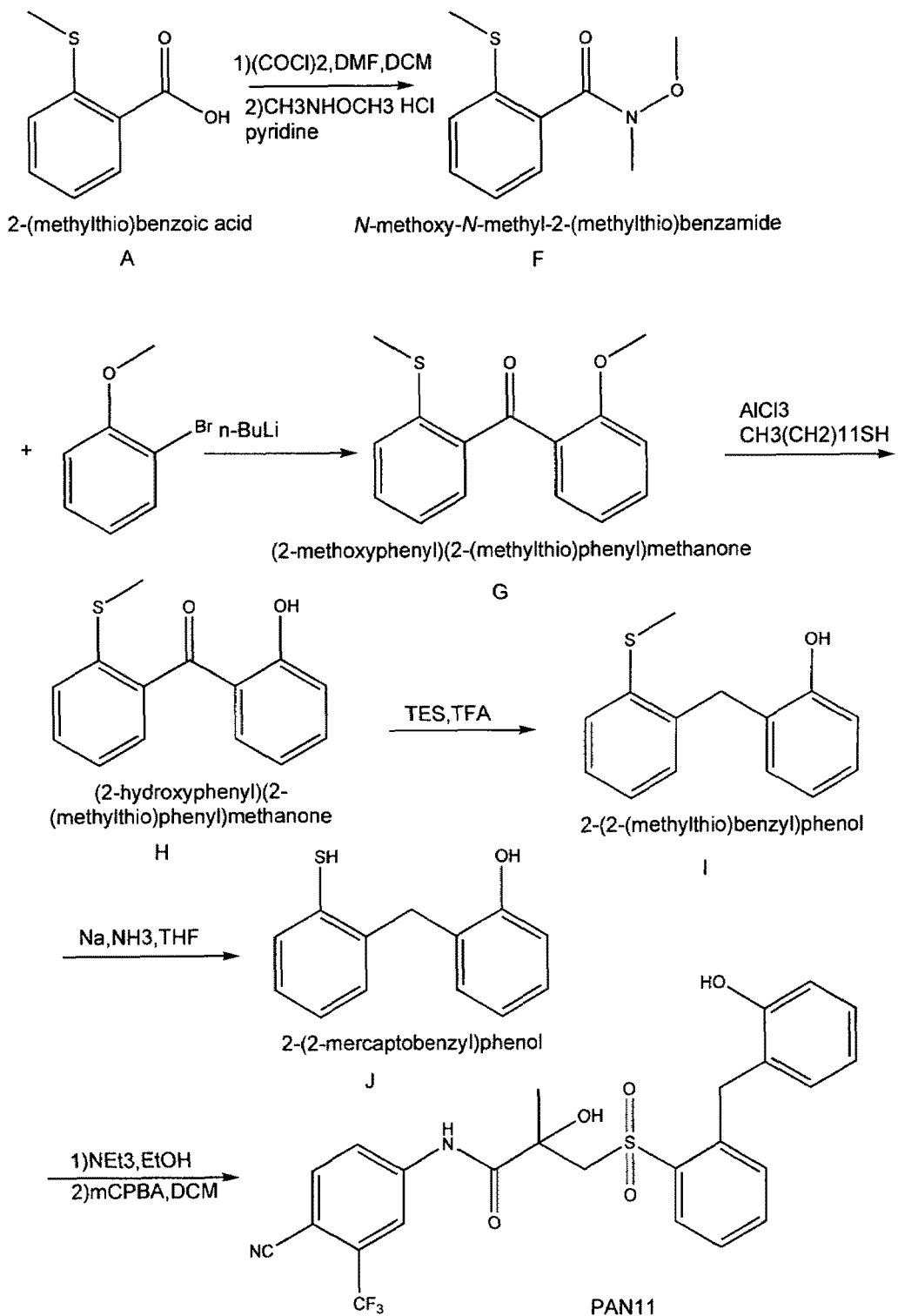
FIG. 13. General strategy for synthesis of PAN11.

To a solution of 0.237 g 2-(2-mercaptobenzyl)phenol (J) and (1.1 mmol) 0.284 g N-(4-Cyano-3-(trifluoromethyl)phenyl)-2-methyloxirane-2-Carboxamide (1.05 mmol) in 4 ml ethanol was added 0.2 ml triethylamine. The reaction was stirred overnight and then concentrated. The residue was dissolved in ethyl acetate, washed with water, brine, dried over magnesium sulfate and concentrated. Without further purification, the residue was treated with 0.6 g mCPBA (2.4 mmol) in 10 ml DCM. The mixture was stirred overnight and concentrated. The residue was dissolved in ethyl acetate, washed with water, brine, dried over magnesium sulfate and concentrated. Purification by silica flash chromatography (hexane:ethyl acetate 50:50) afforded 0.204 g product (0.39 mmol, 39% yield for two steps). Production of PAN11 was confirmed by 1-H NMR and 13-C NMR. See FIG. 13 for the general PAN11 synthesis strategy.

Example 42

(3-methoxyphenyl)(2-(2,4,6-trimethoxybenzylthio)phenyl)methanol (K)

To a solution of 0.35 g (2-bromophenyl)(2,4,6-trimethoxybenzyl)sulfane (0.96 mmol) in dry THF was added slowly 1.2 eq n-BuLi. The reaction was stirred 25 minutes at −78° C. before 1.2 eq 3-methoxybenzaldehyde was added slowly. The reaction was warmed to ambient temperature and stirred for one additional hour before the addition of water. The mixture was extracted with ethyl acetate. The combined organic extracts were washed with brine, dried over magnesium sulfate, filtered and concentrated. Flash silica chromatography (hexane:ethyl acetate 80:20) afforded 0.288 g product (0.68 mmol, 70% yield).

Example 43

2-(3-methoxybenzyl)benzenethiol (L)

0.288 g (3-methoxyphenyl)(2-(2,4,6-trimethoxybenzylthio)phenyl)methanol (K) (0.68 mmol) was treated with a solution of triethylsilane:TFA:DCM 0.3 ml:1 ml:10 ml. The mixture was stirred overnight at ambient temperature before the addition of water. The mixture was extracted with DCM, brine, dried over magnesium sulfate and concentrated. Flash silica chromatography (hexane:ethyl acetate 90:10) afforded 0.12 g product (0.52 mmol, 77% yield).

Example 44

3-(2-mercaptobenzyl)phenol (M)

To a mixture of 0.61 g 2-(3-methoxybenzyl)benzenethiol (L) (2.65 mmol) and 1.94 g $AlCl_3$ was added slowly 1.2 eq n-BuLi. The reaction was stirred overnight before 30 ml water was added. The mixture was extracted with ethyl acetate. The combined organic extracts were washed with brine and dried over magnesium sulfate. The volatiles were removed by distillation under nitrogen. Flash silica chromatography (hexane:ethyl acetate 80:20) afforded 0.23 g product (1.06 mmol, 40% yield).

Example 45

N-(4-Cyano-3-(trifluoromethyl)phenyl)-2-hydroxy-3-(2-(3-hydroxybenzyl)phenylsulfonyl)-2-methyl-propanamide, (PAN21)

Figure 14:
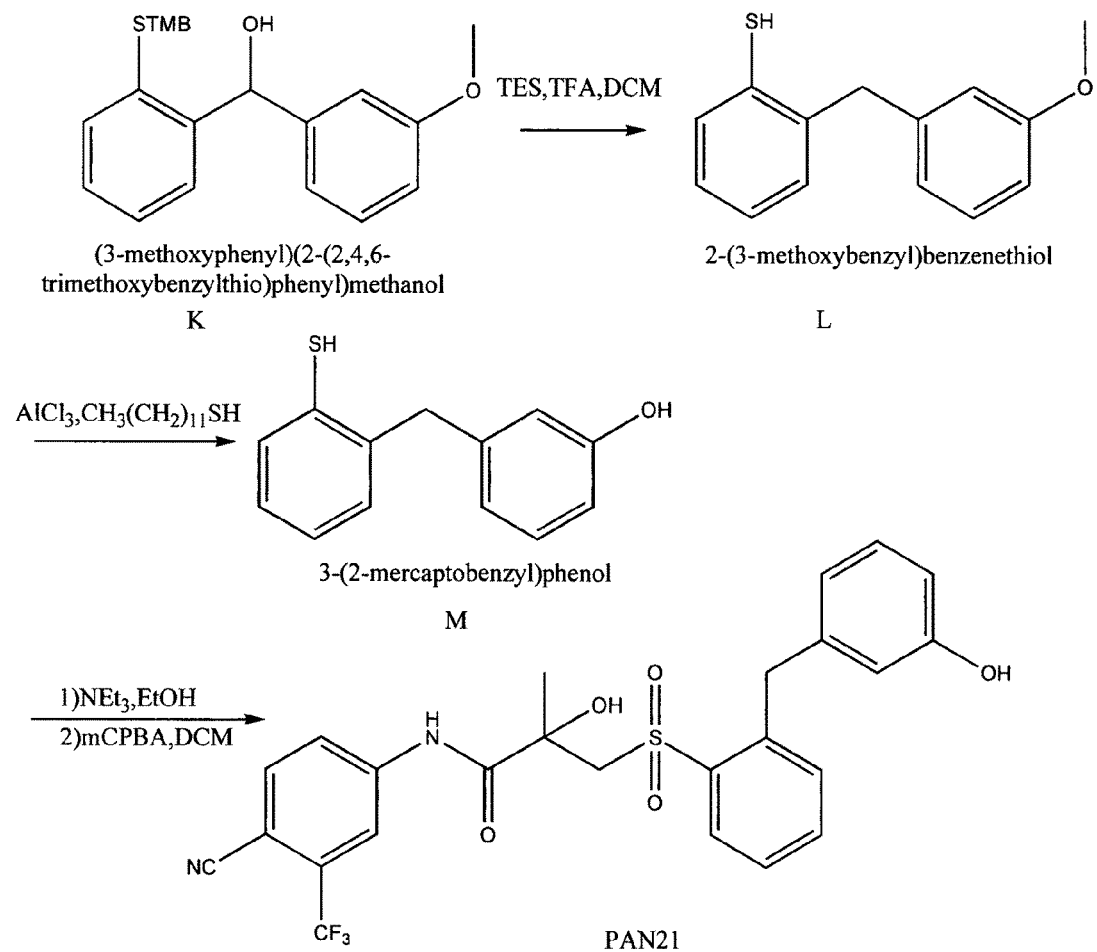
FIG. 14. General strategy for synthesis of PAN21.

To a solution of 0.23 g 3-(2-mercaptobenzyl)phenol (M) (1.0 mmol), 0.26 g N-(4-Cyano-3-(trifluoromethyl)phenyl)-2-methyloxirane-2-Carboxamide (0.95 mmol) in 4 ml ethanol was added, 0.2 ml triethylamine. The reaction was stirred overnight before concentrating. The residue was dissolved in ethyl acetate, washed with water, brine, dried over magnesium sulfate and concentrated. The crude product was dissolved in 10 ml DCM and treated with 0.3 g mCPBA (1.8 mmol). The mixture was stirred overnight and concentrated. The residue was dissolved in ethyl acetate, washed with water, brine, dried over magnesium sulfate and concentrated. Purification by chromatography (hexane:ethyl acetate 50:50) to afford 0.18 g product (0.35 mmol, 35% yield for two steps). Production of PAN21 was confirmed by 1-H NMR and 13-C NMR. See FIG. 14 for the general PAN21 synthesis strategy.

Example 46

(4-methoxyphenyl)(2-(methylthio)phenyl)methanone (C)

To a mixture of 1.788 g 2-(methylthio)benzoyl chloride (B) (9.58 mmol) and 1.6 g $AlCl_3$ at 0° C. was added slowly 20 ml DCM. The mixture was stirred 5 minutes at ambient temperature before 2 g anisole was added slowly. The reaction was stirred 30 minutes at ambient temperature and before water was added slowly. The mixture was extracted with DCM (2×50 ml). The combined organic extracts were washed with brine, dried over magnesium sulfate and concentrated. Flash silica chromatography (hexane:ethyl acetate 85:15) afforded 1.85 g pale yellow solid product (7.17 mmol, 75% yield).

Example 47

(4-hydroxyphenyl)(2-mercaptophenyl)methanone (D)

To a nitrogen flushed mixture of 1.415 g (4-methoxyphenyl)(2-(methylthio)phenyl)methanone (C) (5.48 mmol) and 3 g sodium thiolate (26.6 mmol) was added 40 ml anhydrous DMF. The mixture was refluxed under nitrogen. After the mixture turned to black, the reaction was refluxed for two more hours cooled to RT and quenched with water. The mixture was washed ethyl acetate (2×100 ml). The combined organic was brined, dried over magnesium sulfate, filtered and concentrated. Flash column (hexane:ethyl acetate 80:20) yield 0.954 g product (4.0 mmol, 73% yield).

Example 48

4-(2-mercaptobenzyl)phenol (E)

To a mixture of 0.954 g (4-hydroxyphenyl)(2-mercaptophenyl)methanone (D) (4.0 mmol), 1 ml triethylsilane was added 5 ml TFA. The mixture was stirred at ambient temperature for 1 hour before water was added. The reaction mixture was extracted with ethyl acetate (2×70 ml), brine, dried over magnesium sulfate, filtered and concentrated. Flash silica chromatography (hexane:ethyl acetate 80:20) afforded 0.786 g product (3.5 mmol, 88% yield).

Example 49

N-(4-Cyano-3-(trifluoromethyl)phenyl)-2-hydroxy-3-(2-(4-hydroxybenzyl)phenylsulfonyl)-2-methyl-propanamide, (PAN31)

Figure 15:
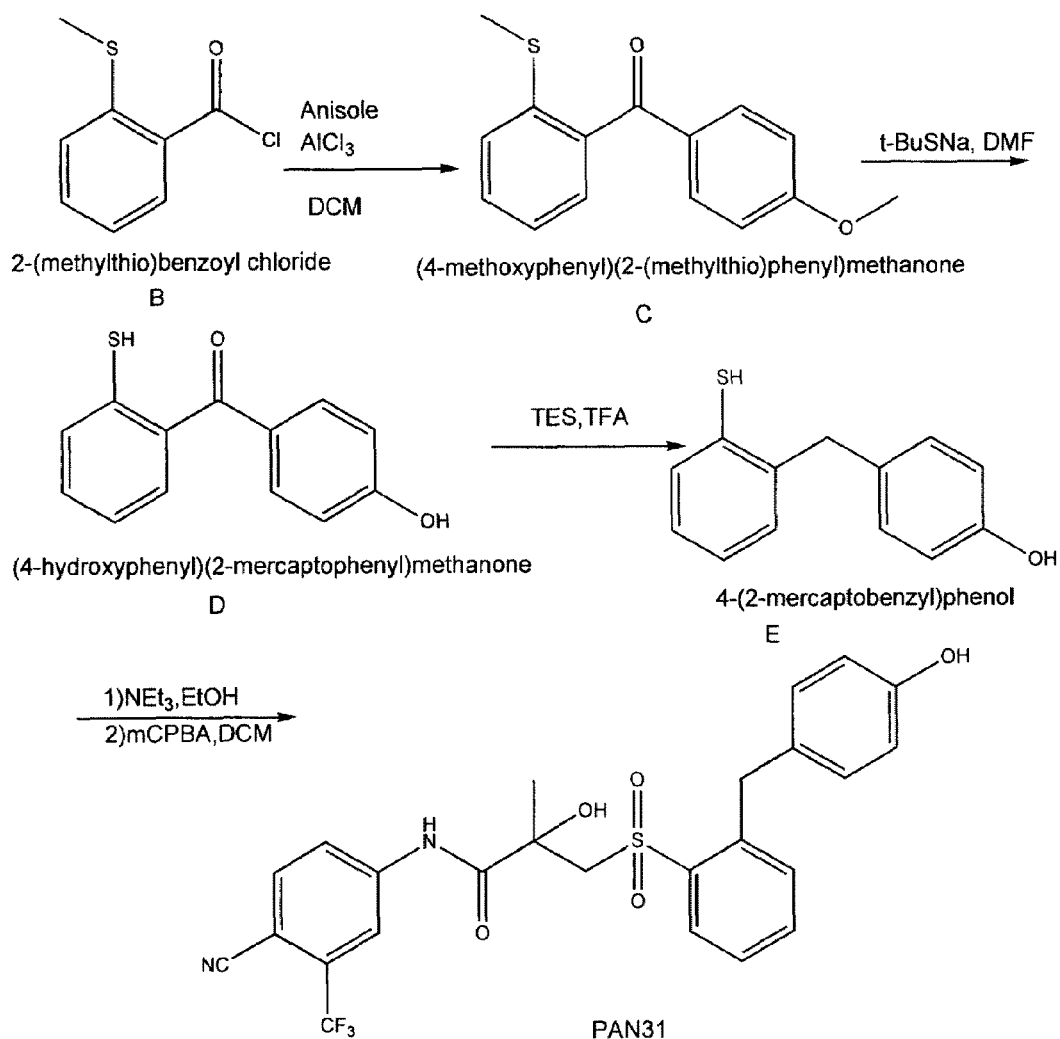
FIG. 15. General strategy for synthesis of PAN31.

A solution of 1.12 g 4-(2-mercaptobenzyl)phenol (E) (5.18 mmol), 1.34 g N-(4-cyano-3-(trifluoromethyl)phenyl)-2-methyloxirane-2-Carboxamide (4.9 mmol) in 8 ml ethanol was treated with 1 ml triethylamine. After reaction at ambient temperature overnight, the mixture was concentrated and the residue was dissolved in ethyl acetate, washed with water, brine, dried over magnesium sulfate and concentrated. Without further purification, the residue was dissolved in 30 ml DCM and treated with 3.85 g mCPBA (15.5 mmol). The mixture was stirred overnight and concentrated. The residue was dissolved in ethyl acetate, washed with water, brine, dried over magnesium sulfate and concentrated. Purification by silica flash chromatography (hexane:ethyl acetate 50:50) afforded 0.47 g product (0.91 mmol, 18% yield for two steps). Production of PAN31 was confirmed by 1-H NMR and 13-C NMR. See FIG. 15 for the general PAN31 synthesis strategy.

Example 50

N-(4-Cyano-3-(trifluoromethyl)phenyl)-3-(2-(4-(cyanomethoxy)benzyl)phenylsulfonyl)-2-hydroxy-2-methylpropanamide, (PAN32)

To a mixture of 0.115 g PAN31 and 50 mg potassium carbonate in 2 ml dry DMF was added 0.2 ml $ClCH_2CN$ was stirred overnight at RT. Water was added. The mixture was washed with ethyl acetate, brine, dried over magnesium sulfate, filtered and concentrated. Flash silica chromatography (hexane:ethyl acetate 40:60) afforded 77 mg product. Production of PAN32 was confirmed by 1-H NMR and 13-C NMR.

Example 51

N-(4-Cyano-3-(trifluoromethyl)phenyl)-2-hydroxy-3-(2-(4-methoxybenzyl)phenylsulfonyl)-2-methylpropanamide, (PAN33)

To a mixture of 0.1 g PAN31 and 50 mg potassium carbonate in 2 ml dry DMF was added 0.2 ml methyl iodide. The reaction mixture was stirred overnight at ambient temperature before water was added. The mixture was washed with ethyl acetate and brine, dried over magnesium sulfate, filtered and concentrated. Flash silica chromatography (hexane:ethyl acetate 40:60) afforded 65 mg product. Production of PAN33 was confirmed by 1-H NMR and 13-C NMR.

Example 52

N-(4-Cyano-3-(trifluoromethyl)phenyl)-2-hydroxy-3-(2-(4-(methoxymethoxy)benzyl)phenylsulfonyl)-2-methylpropanamide, (PAN37)

The mixture of 0.1 g PAN31, 50 mg potassium carbonate in 2 ml dry DMF was treated with 0.1 ml methoxymethylchloride. The reaction mixture was stirred overnight at ambient temperature before water was added. The mixture was washed with ethyl acetate and brine, dried over magnesium sulfate, filtered and concentrated. Flash silica chromatography (hexane:ethyl acetate 40:60) afforded 21 mg product. Production of PAN37 was confirmed by 1-H NMR and 13-C NMR.

Example 53

(2,5-dimethylphenyl)(2-(methylthio)phenyl)methanone

To a mixture of 1.2 g 2-(methylthio)benzoyl chloride (B) and 1.55 g AlCl$_3$ at 0° C. was added slowly 20 ml DCM. The mixture was stirred 5 minutes at ambient temperature before 7.8 g p-xylene was added slowly. The reaction was stirred 30 minutes at ambient temperature before water was added slowly. The mixture was extracted with DCM (2×50 ml). The combined organic layer was washed with brine, dried over magnesium sulfate, filtered and concentrated. Flash silica chromatography (hexane:ethyl acetate 85:15) afforded 0.758 g product.

Example 54

(2-(2,5-dimethylbenzyl)phenyl)(methyl)sulfane

To a solution of 0.758 g (2,5-dimethylphenyl)(2-(methylthio)phenyl)methanone and 1 ml triethylsilane was added 5 ml TFA. The reaction mixture was stirred at RT for 1 hour before water was added. The reaction mixture was extracted with ethyl acetate (2×70 ml) and the combined organic extracts were washed with brine, dried over magnesium sulfate, filtered and concentrated. Flash silica chromatography (hexane:ethyl acetate 80:20) yielded 0.666 g product.

Example 55

2-(2,5-dimethylbenzyl)benzenethiol

To a nitrogen flushed mixture of 0.666 g (2-(2,5-dimethylbenzyl)phenyl)(methyl)sulfane and 0.6 g sodium thiolate was added 15 ml anhydrous DMF. The mixture was refluxed under nitrogen until the mixture turned black. The mixture was refluxed for an additional two hours before being cooled to ambient temperature and the addition of water. The mixture was washed with ethyl acetate (2×50 ml). The combined organic extracts were washed with brine, dried over magnesium sulfate, filtered and concentrated. Flash silica chromatography (hexane:ethyl acetate 80:20) afforded 0.51 g product.

Example 56

N-(4-Cyano-3-(trifluoromethyl)phenyl)-3-(2-(2,5-dimethylbenzyl)phenylsulfonyl)-2-hydroxy-2-methylpropanamide, (PAN71)

Figure 16:
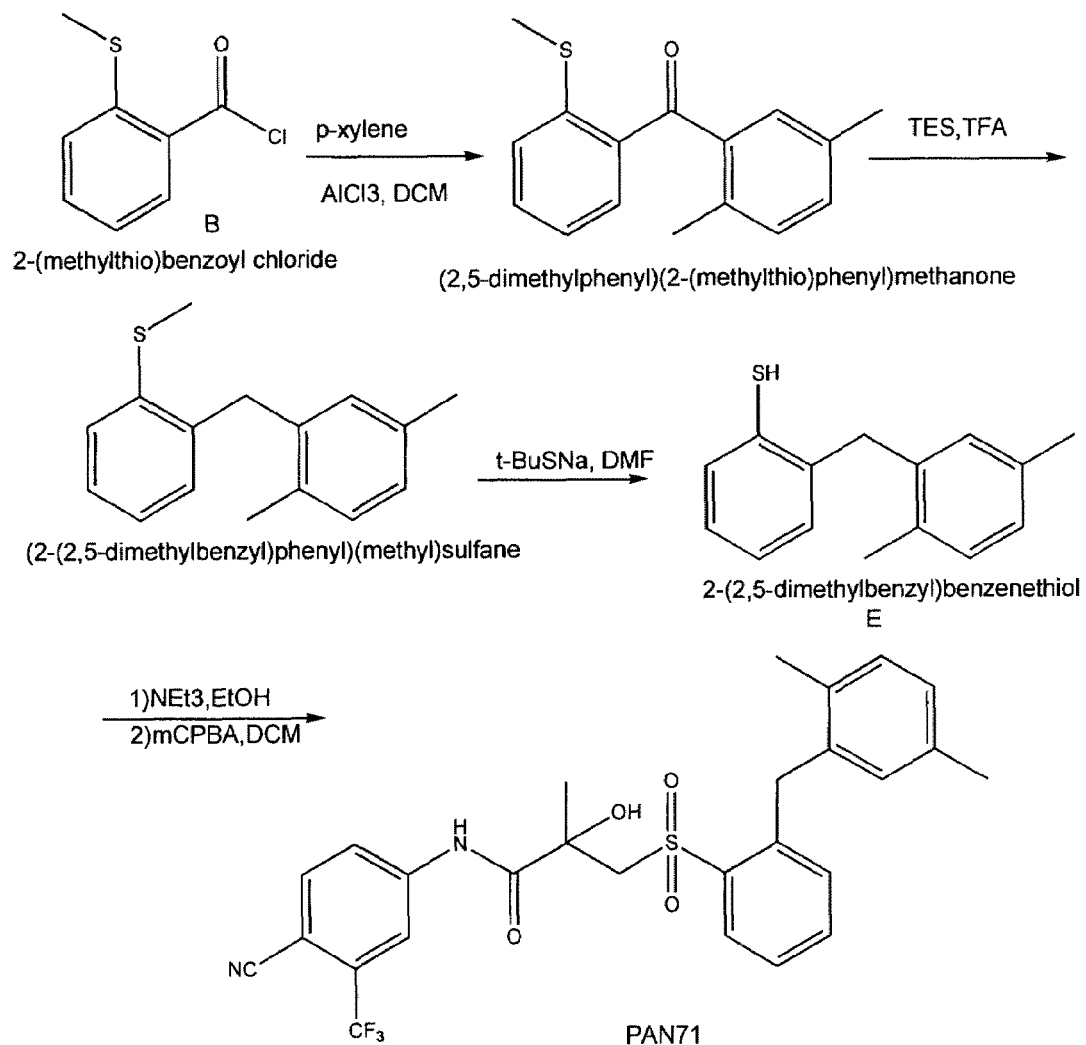
FIG. 16. General strategy for synthesis of PAN71.
Figure 17:
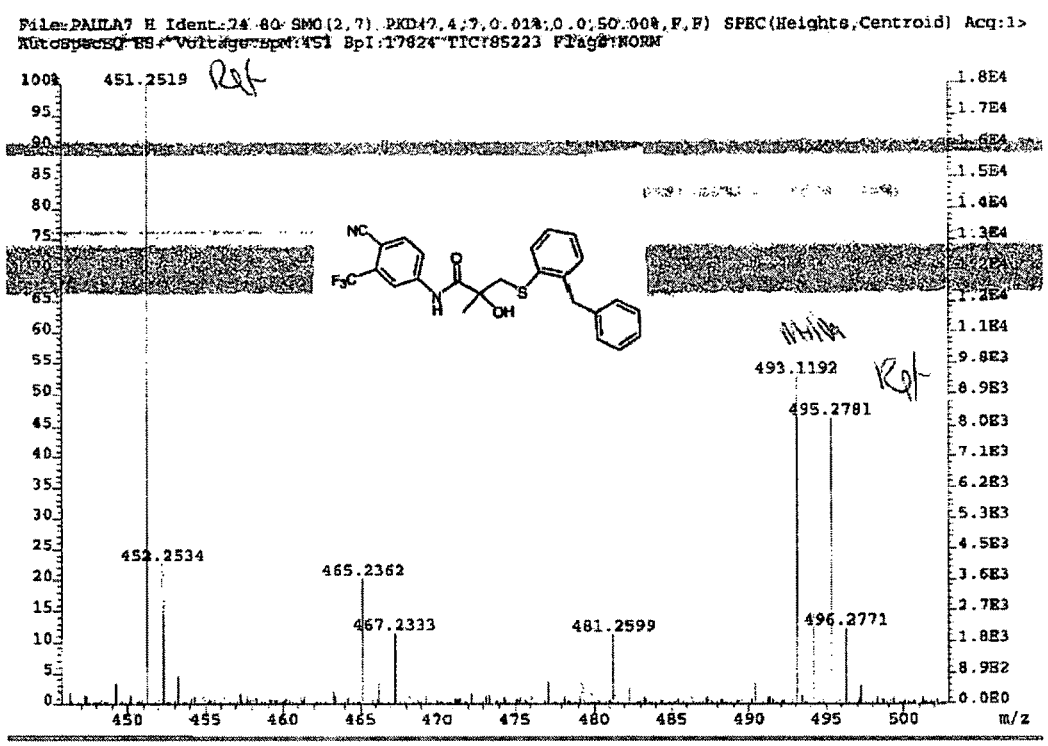
Figure 18:
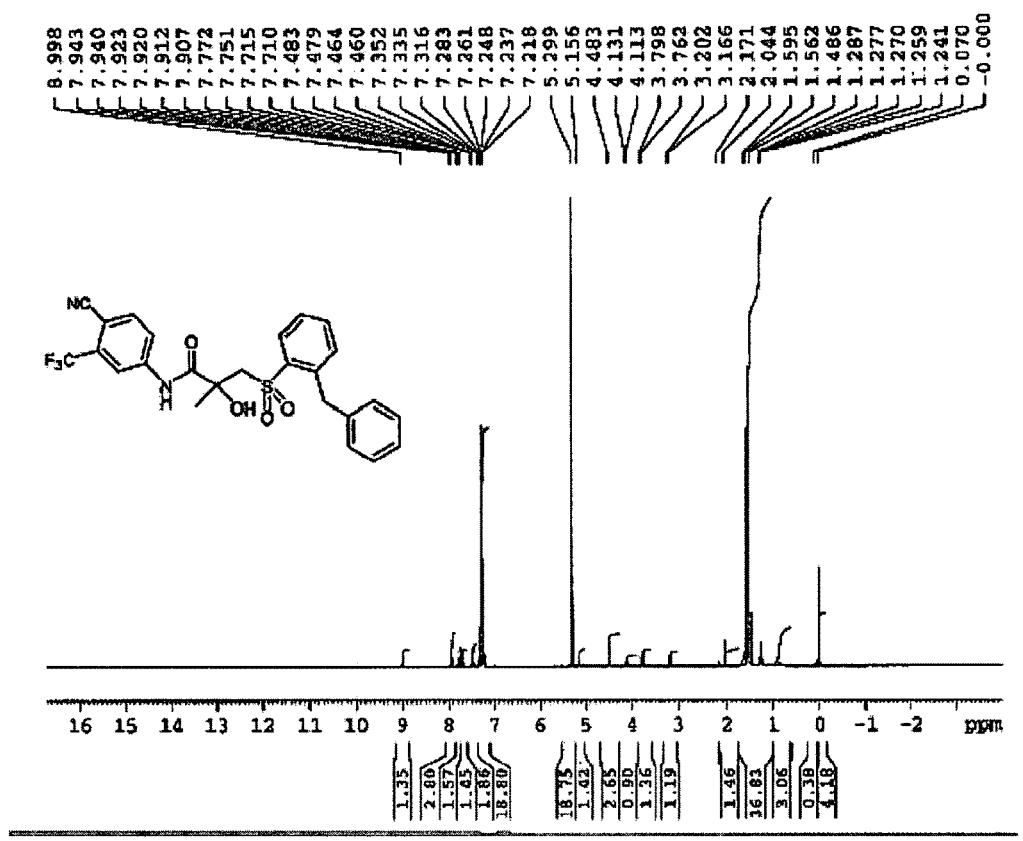
Figure 19:
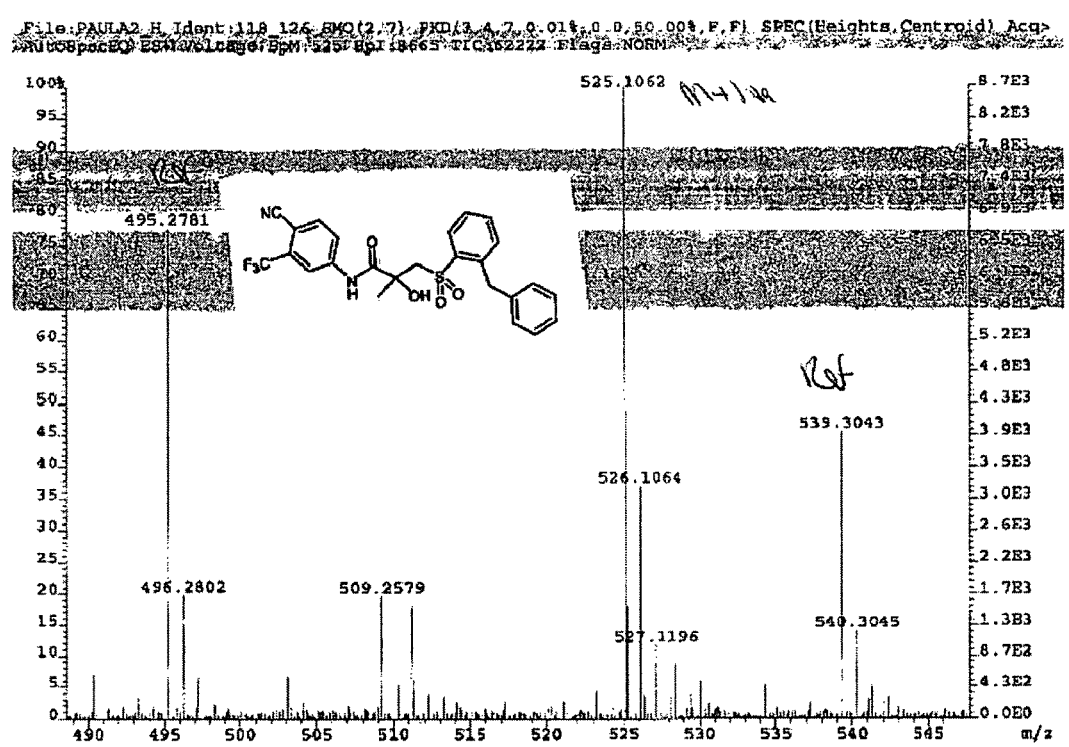
Figure 20:
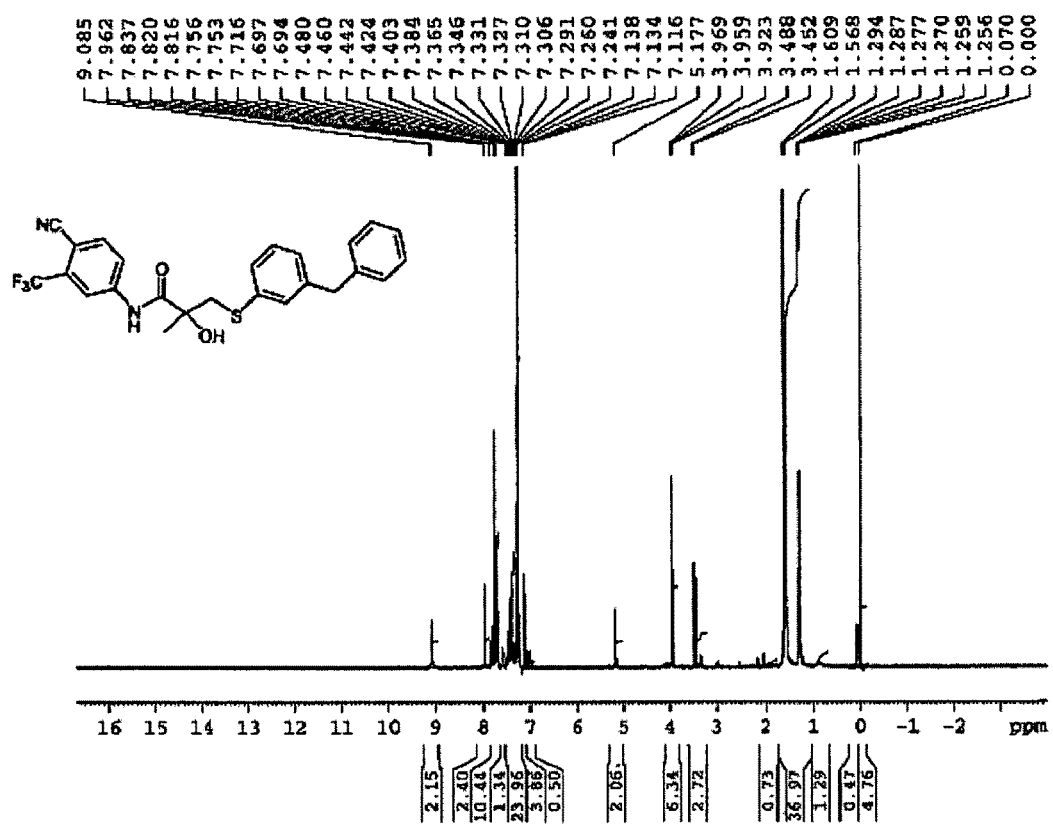
Figure 21:
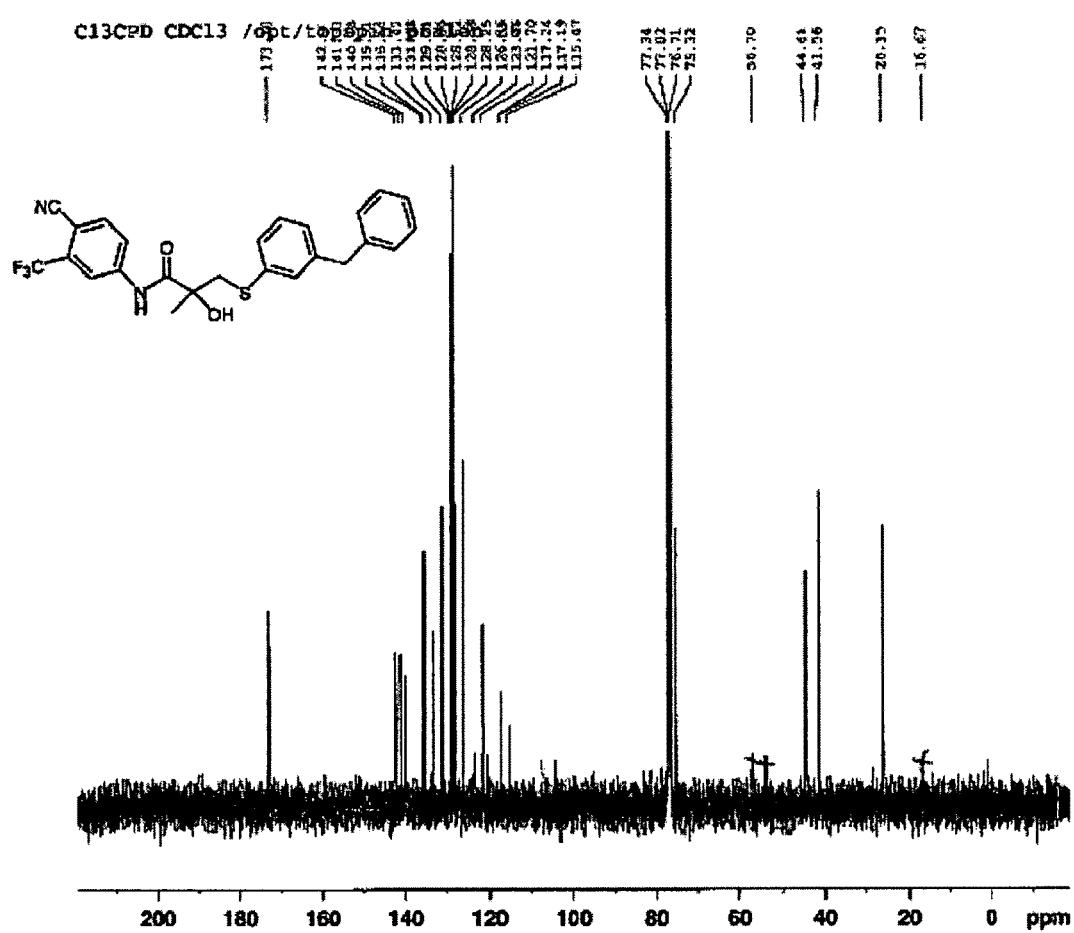
Figure 22:
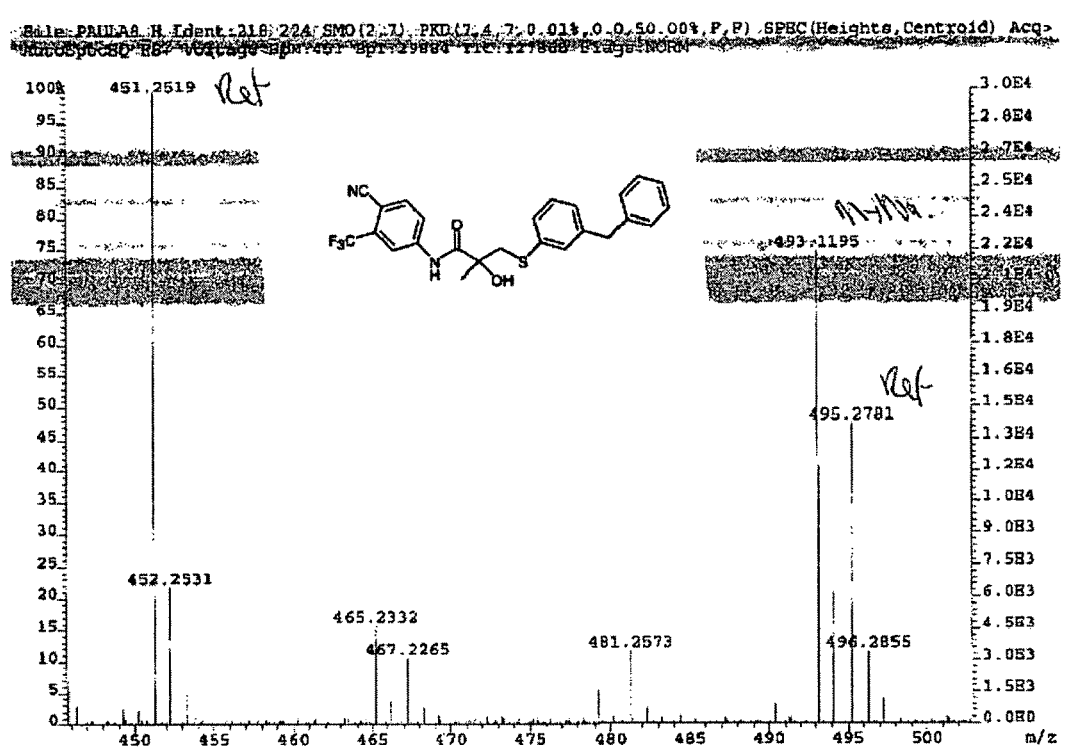
Figure 23:
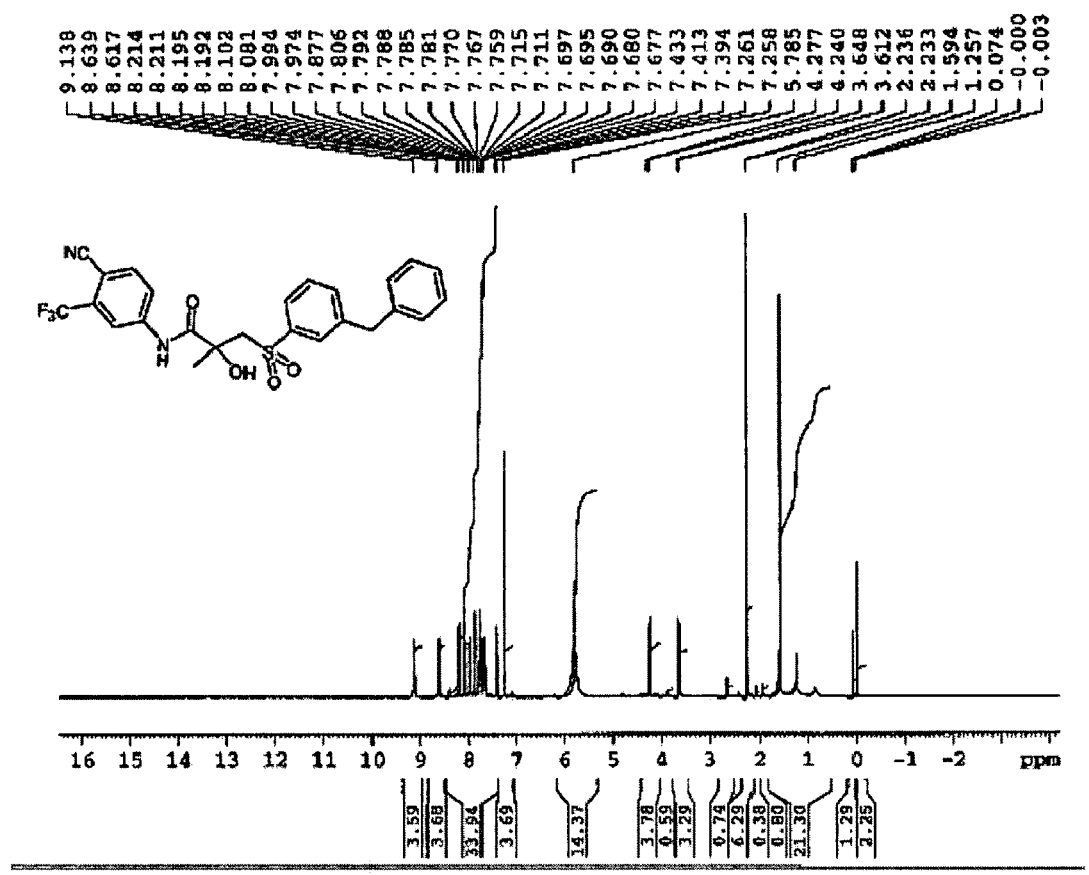
Figure 24:
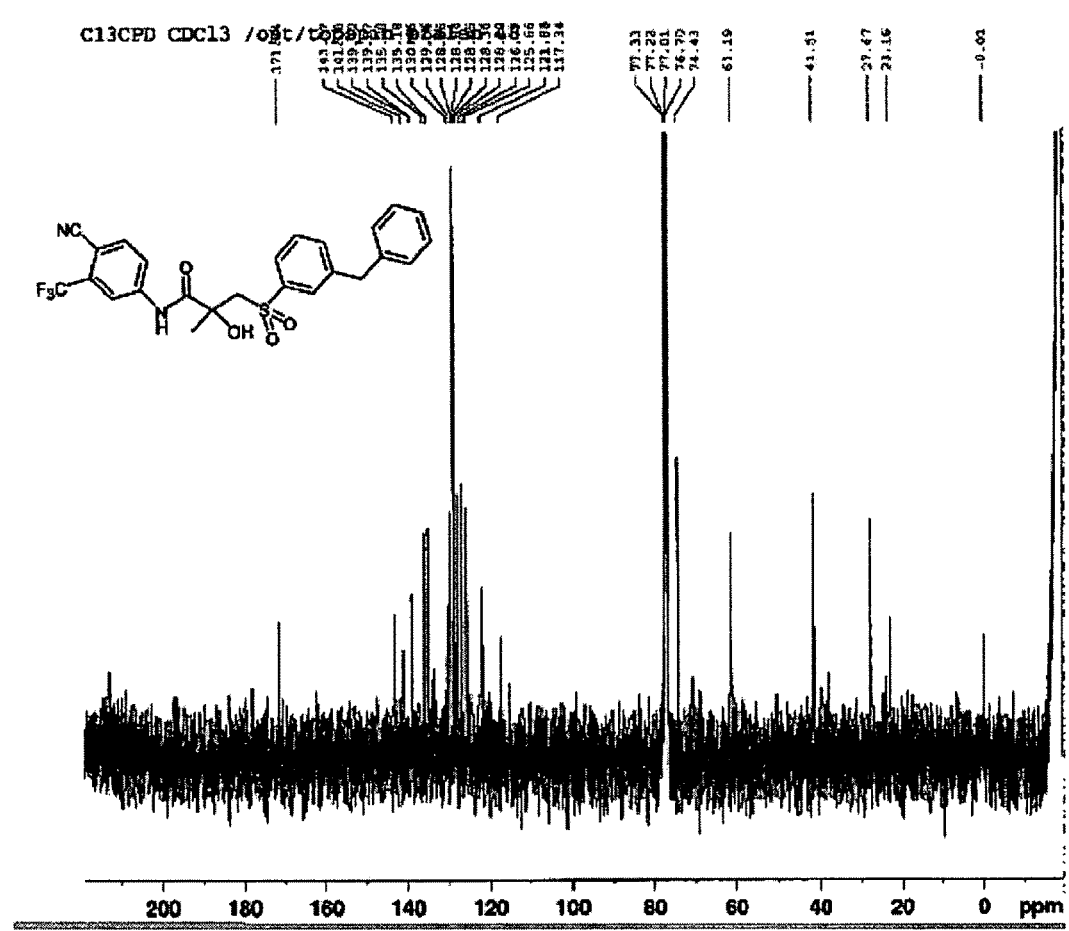
Figure 25:
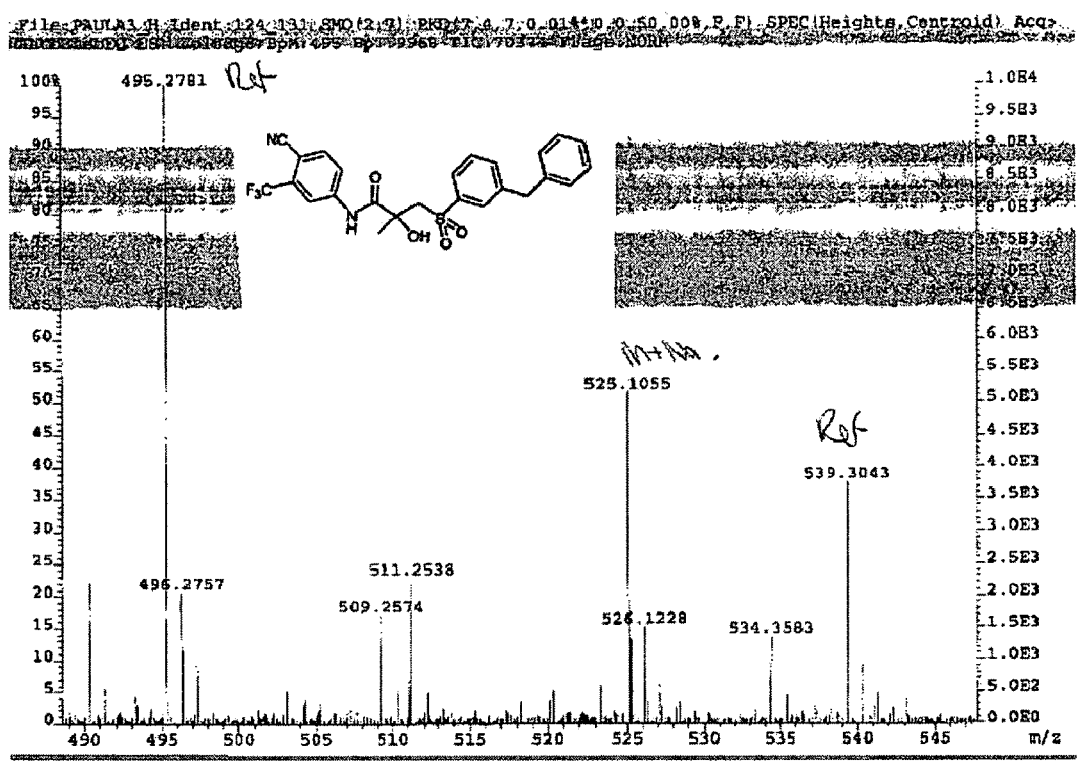
Figure 26:
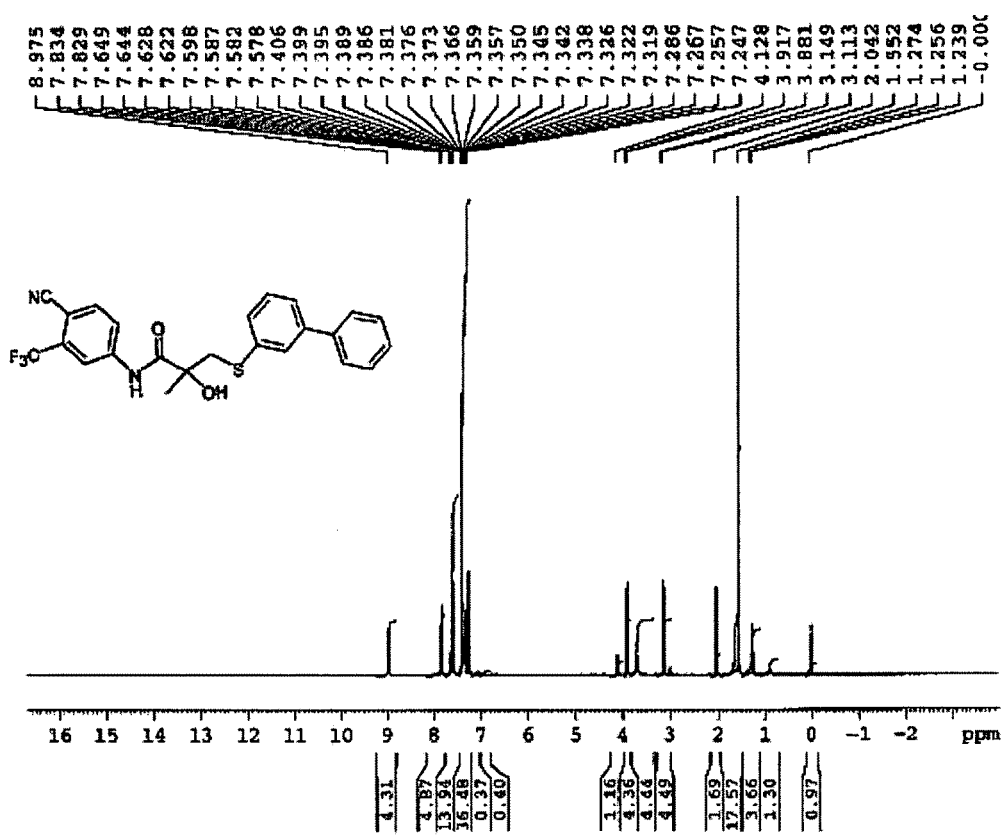
Figure 27:
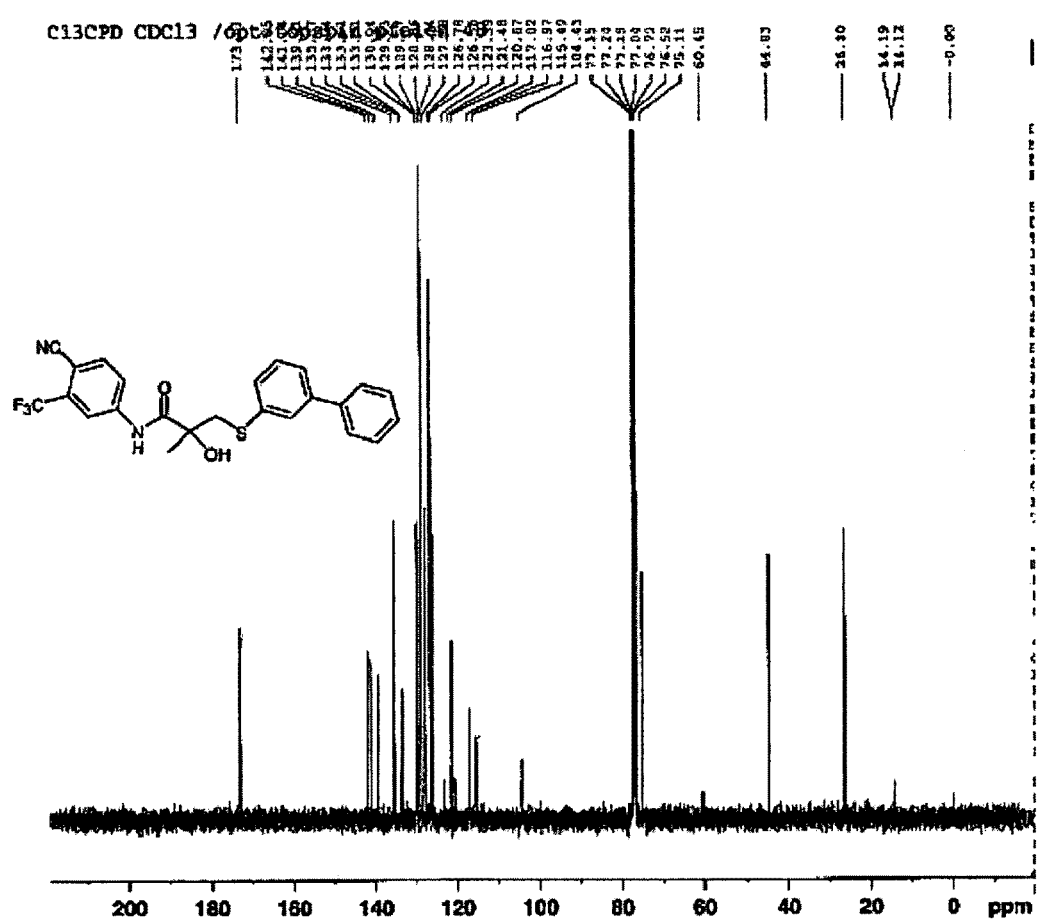
Figure 28:
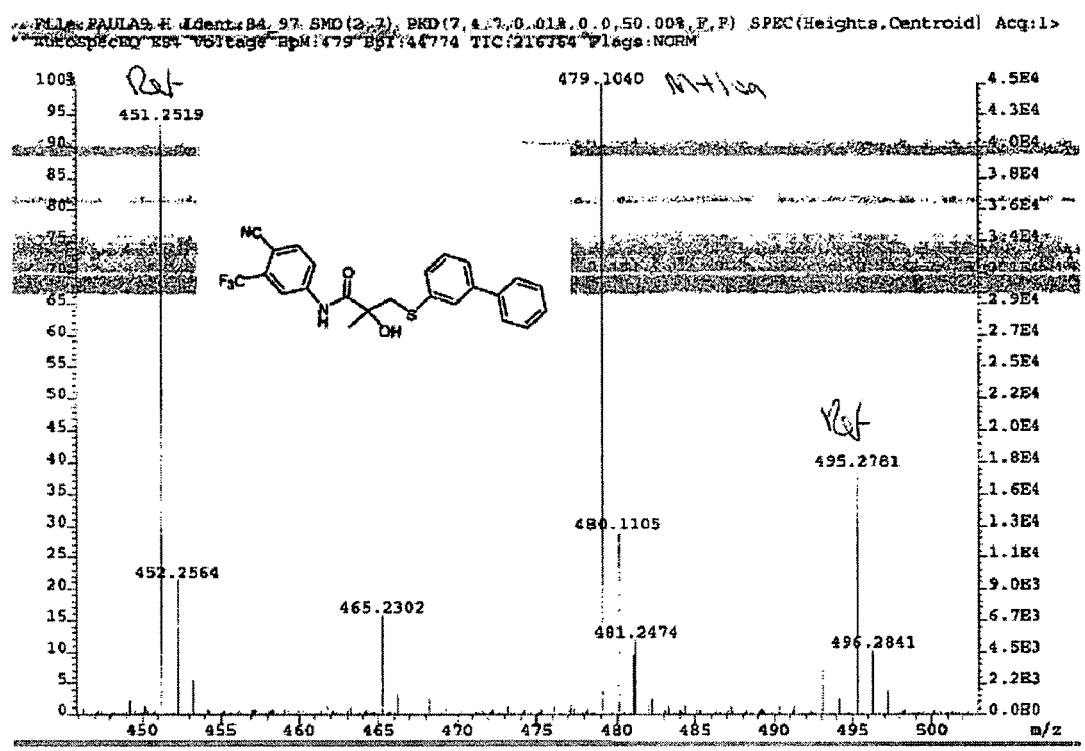
Figure 29:
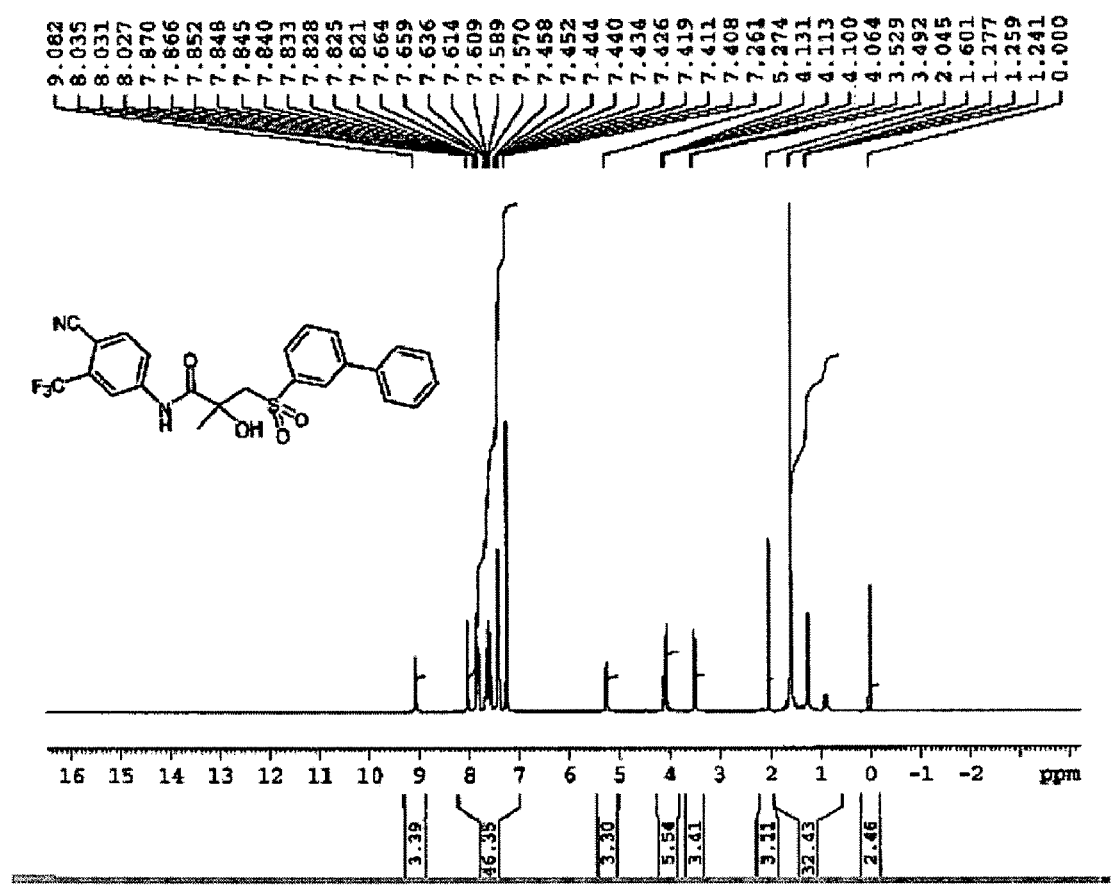
Figure 30:
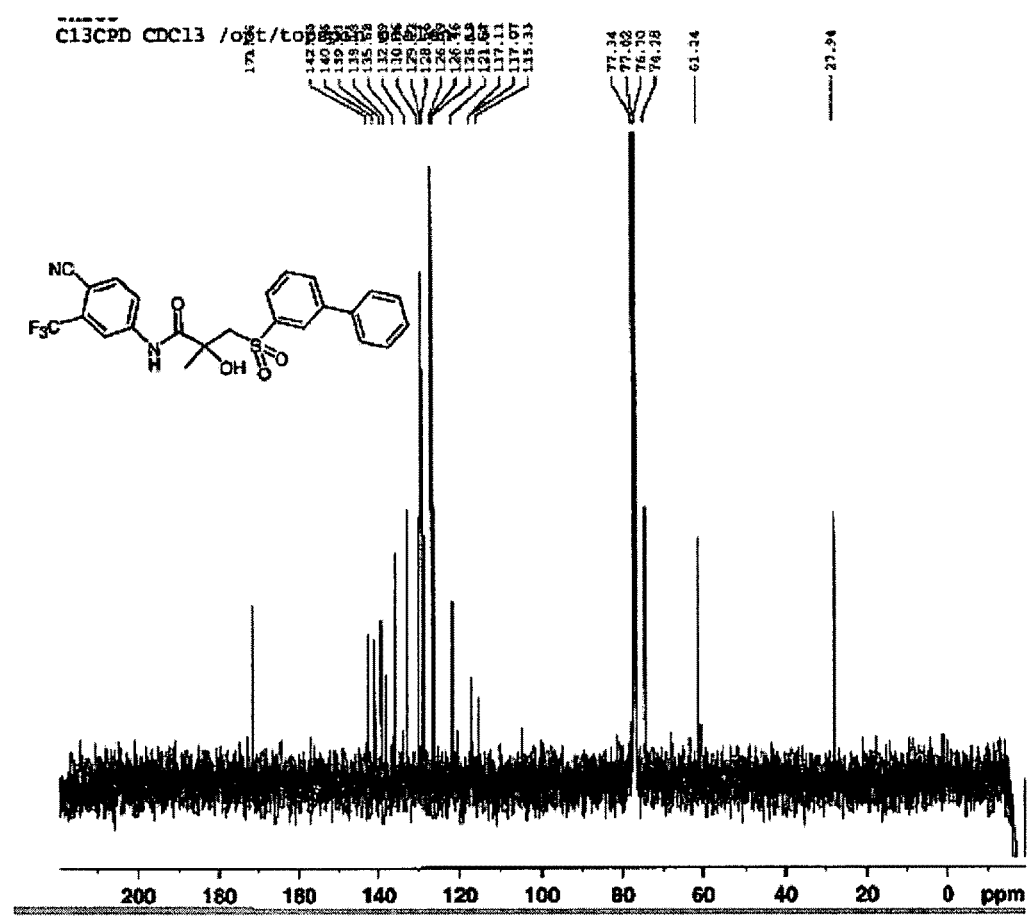
Figure 31:
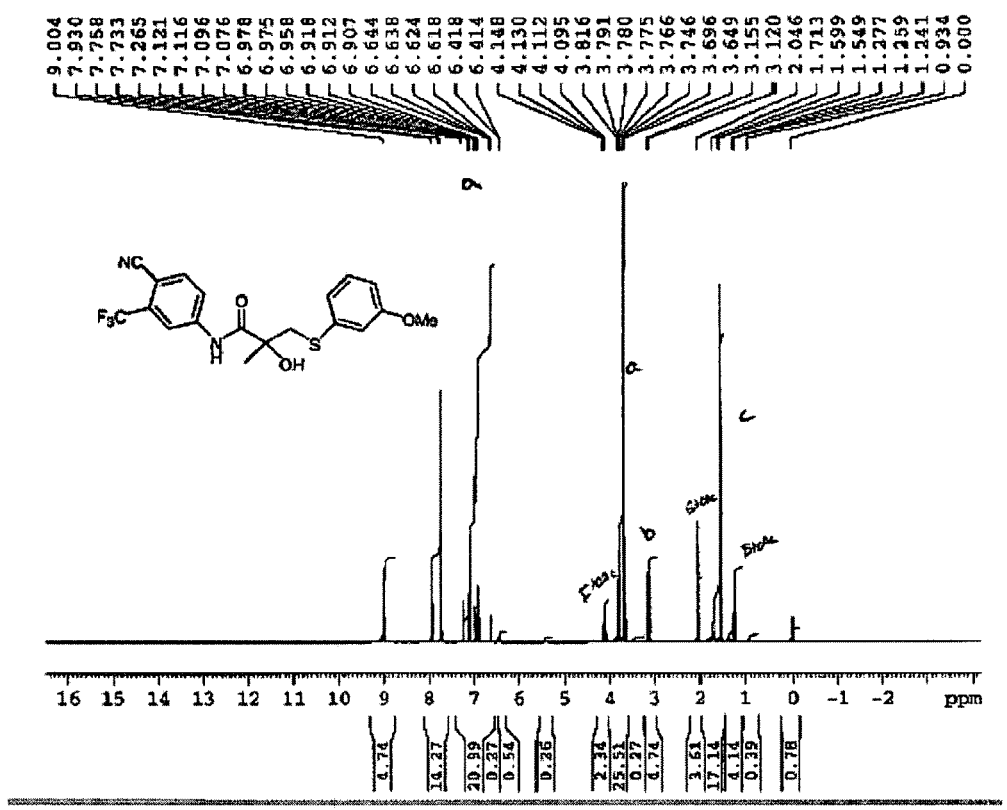
Figure 32:
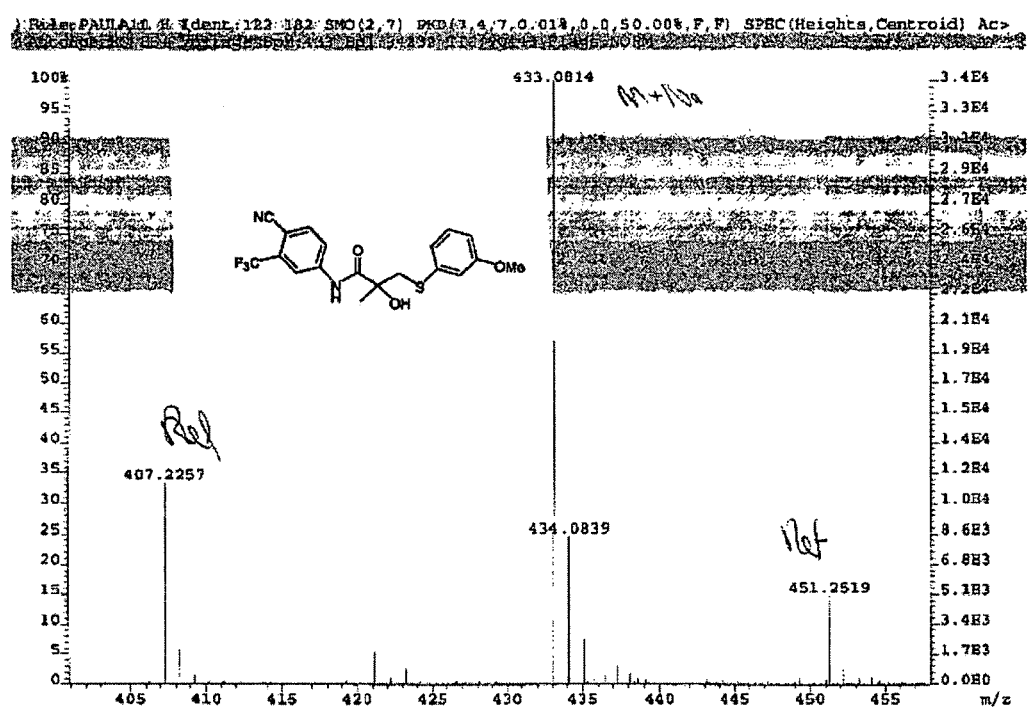
Figure 33:
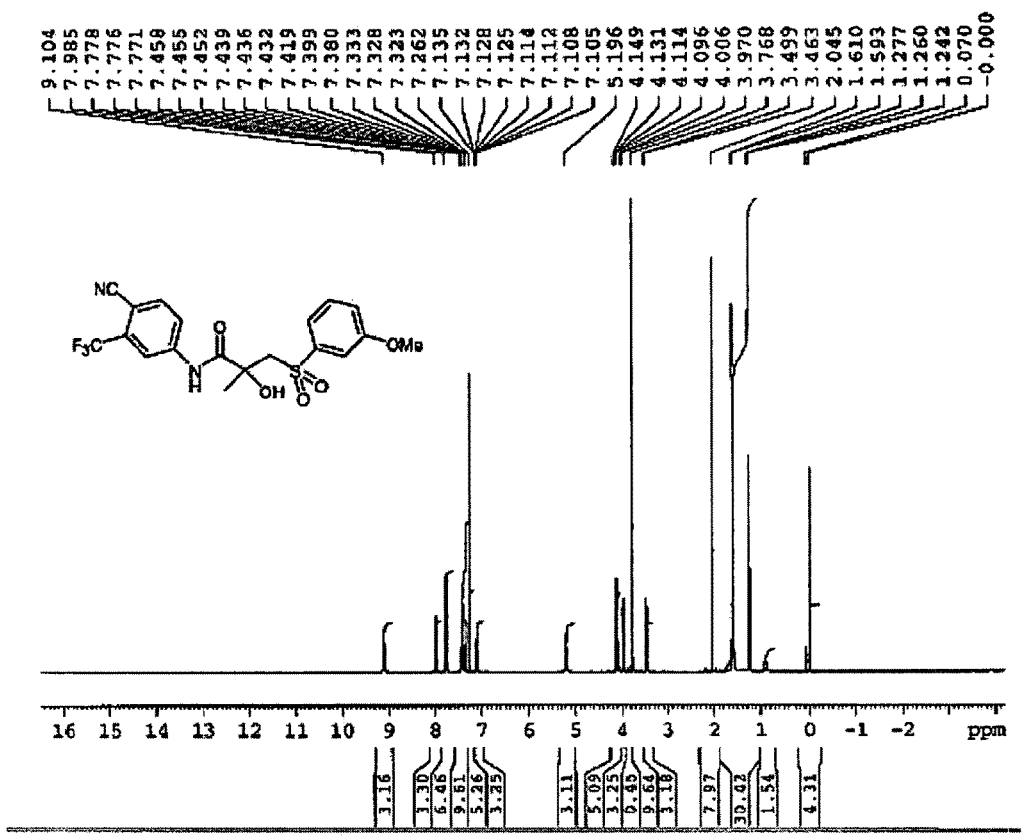
Figure 34:
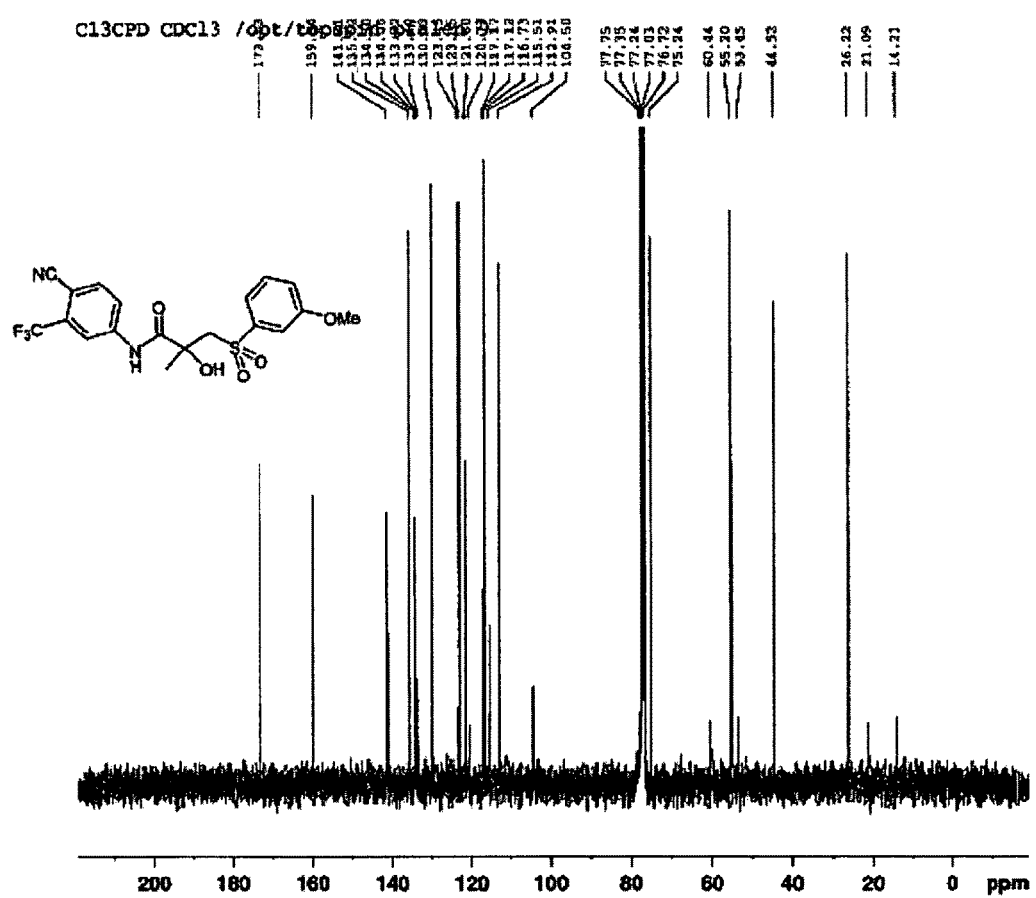
Figure 35:
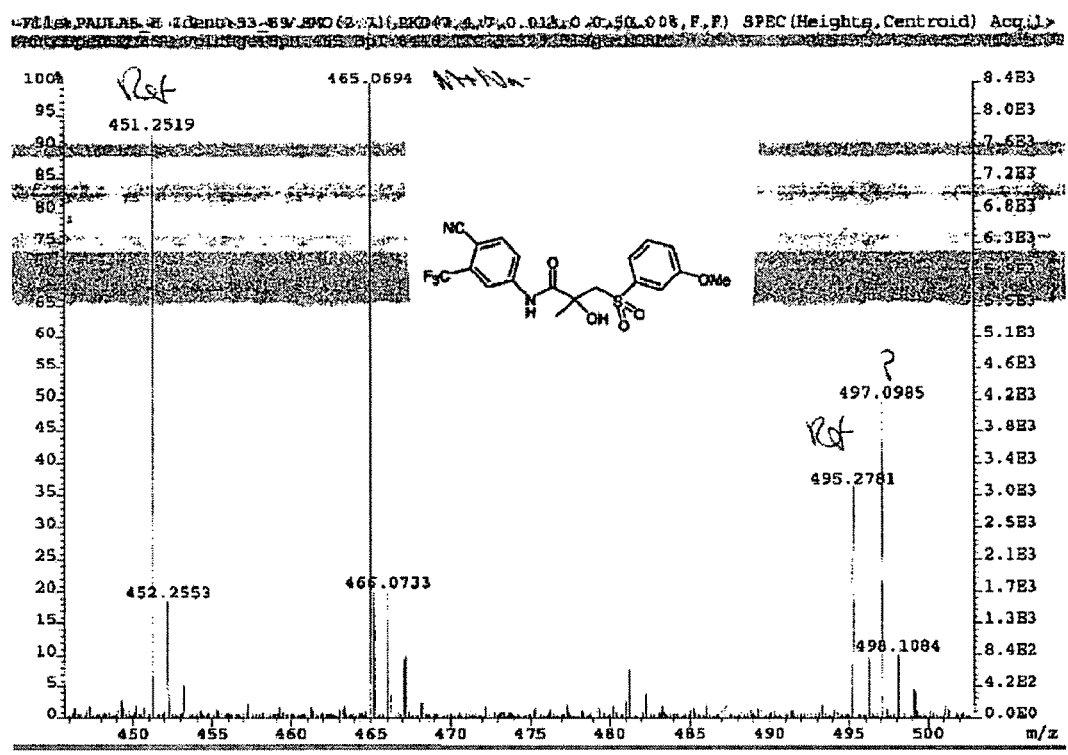
Figure 36:
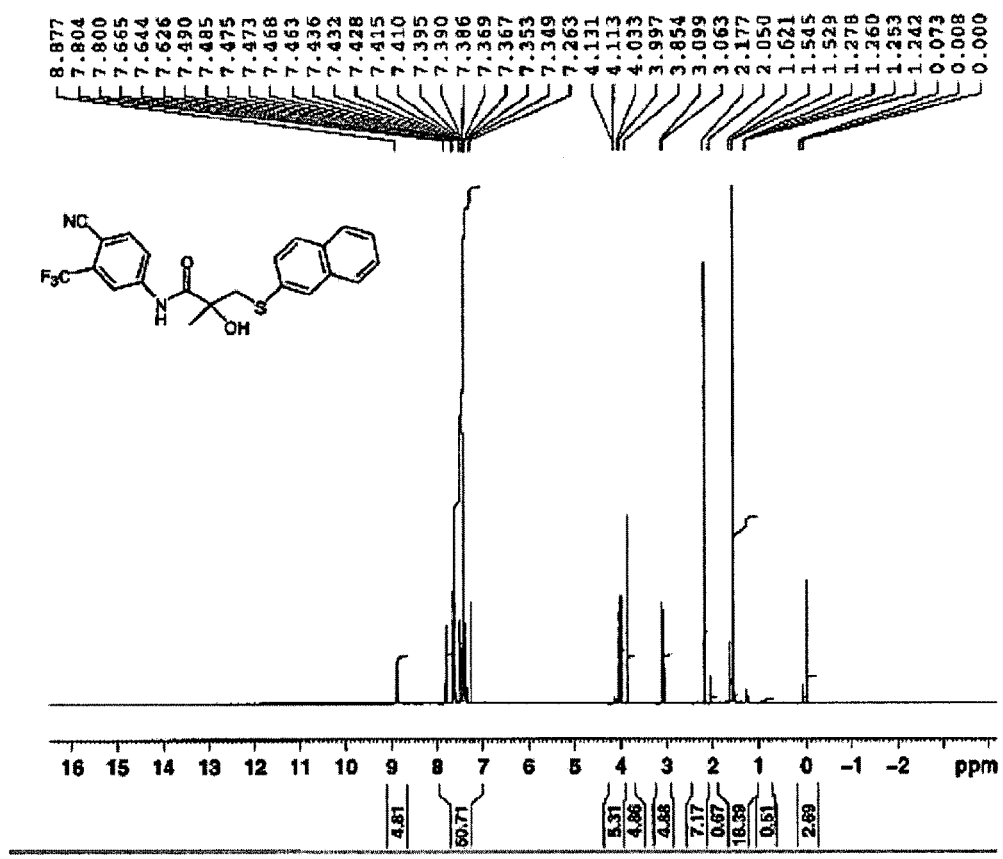
Figure 37:
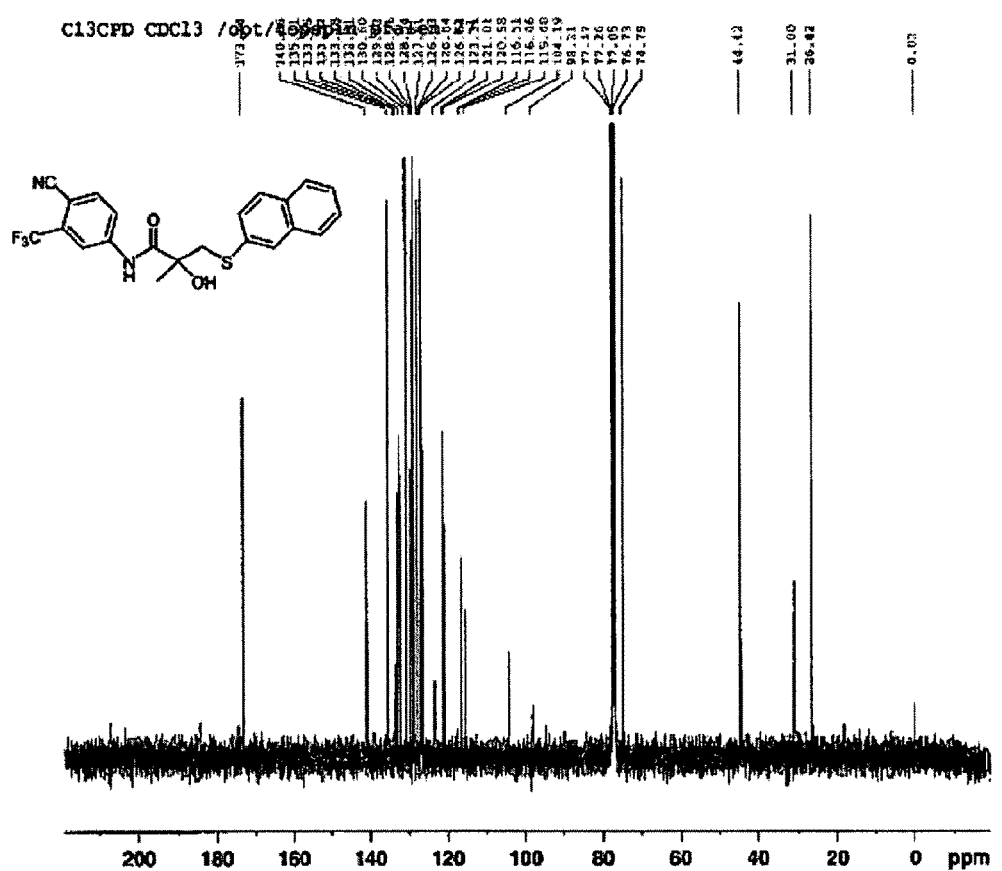
Figure 38:
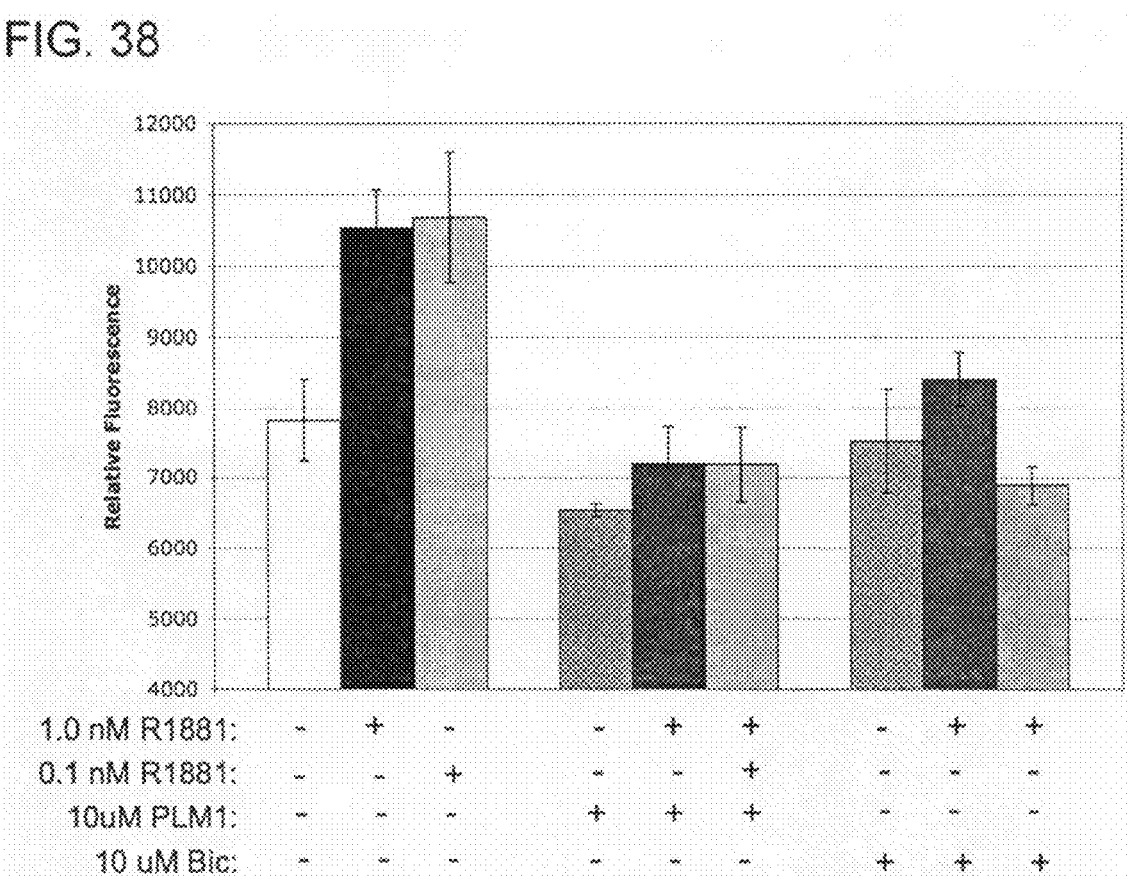
Figure 39:
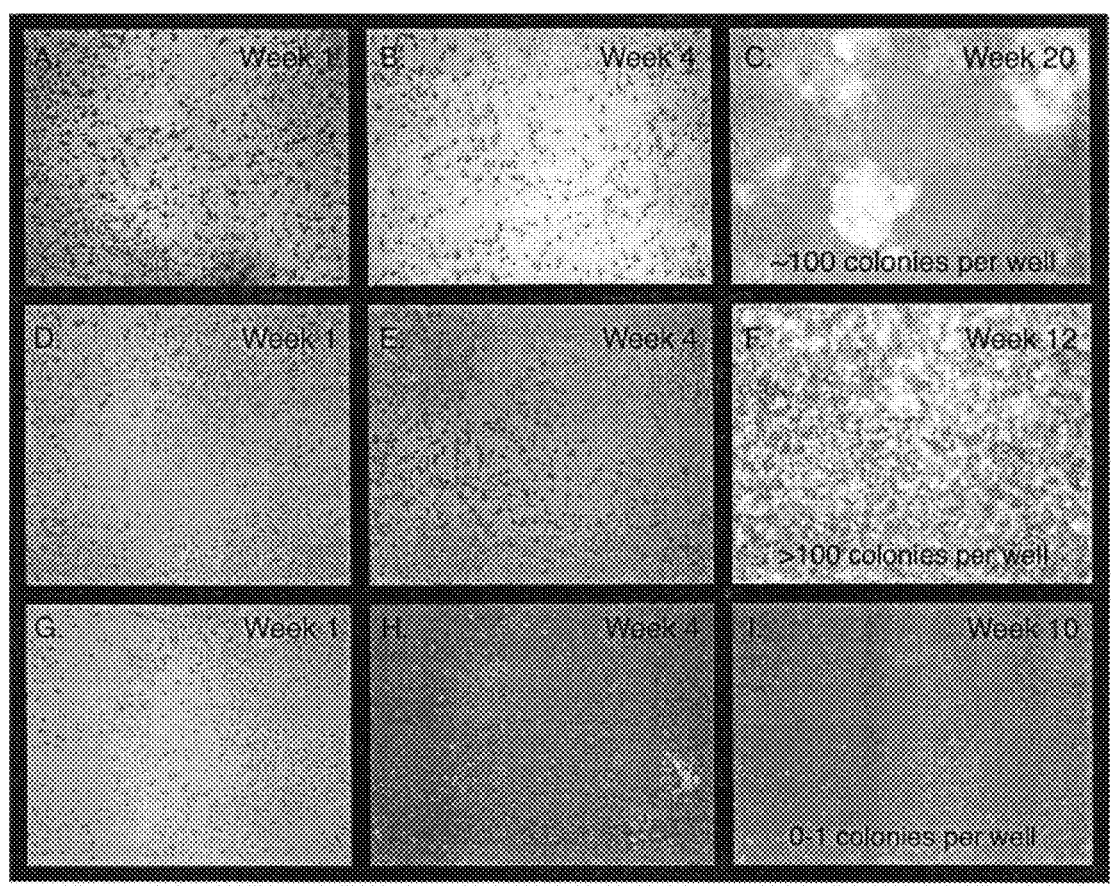
Figure 40:
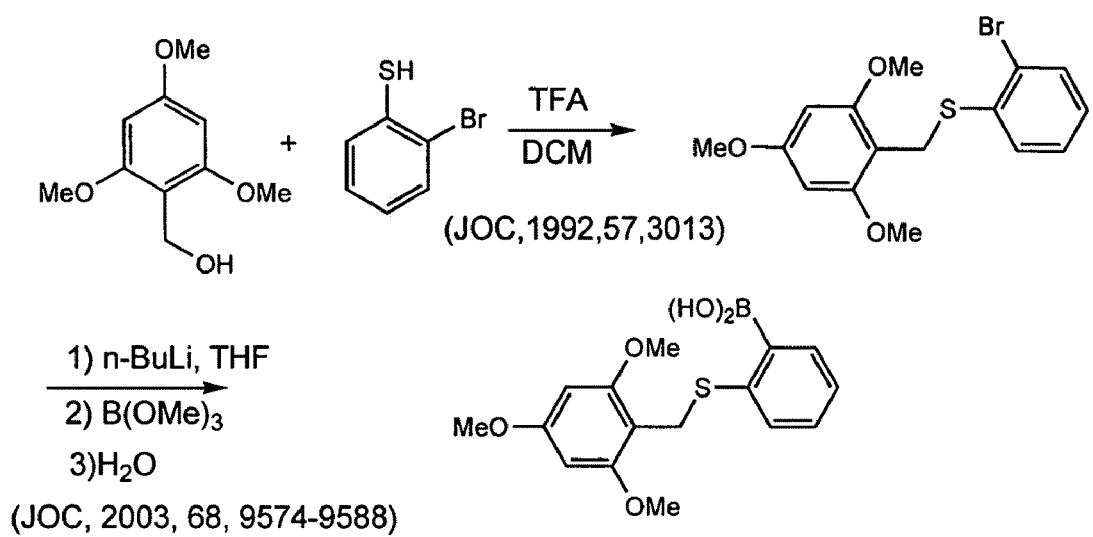
Figure 41:
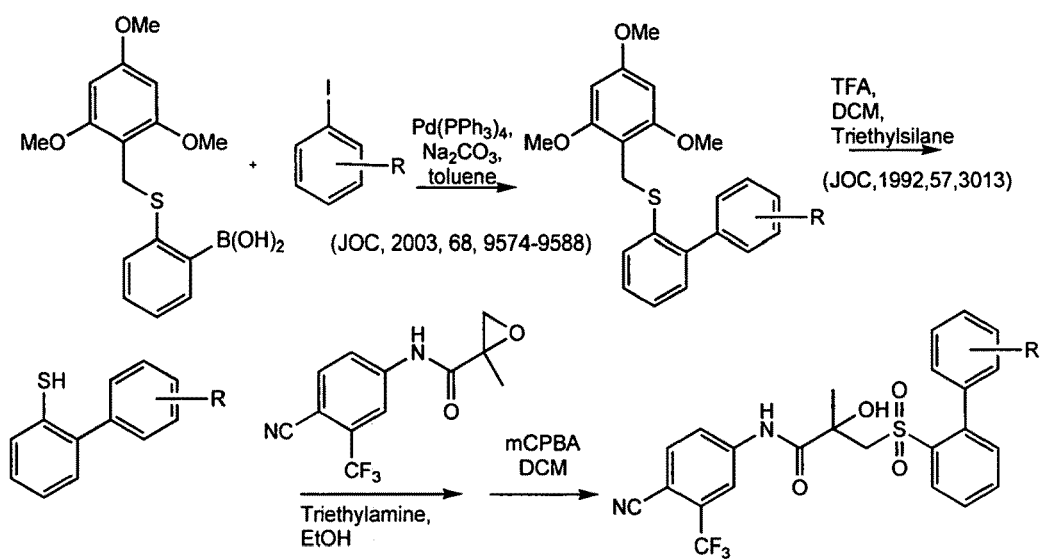
Figure 42:
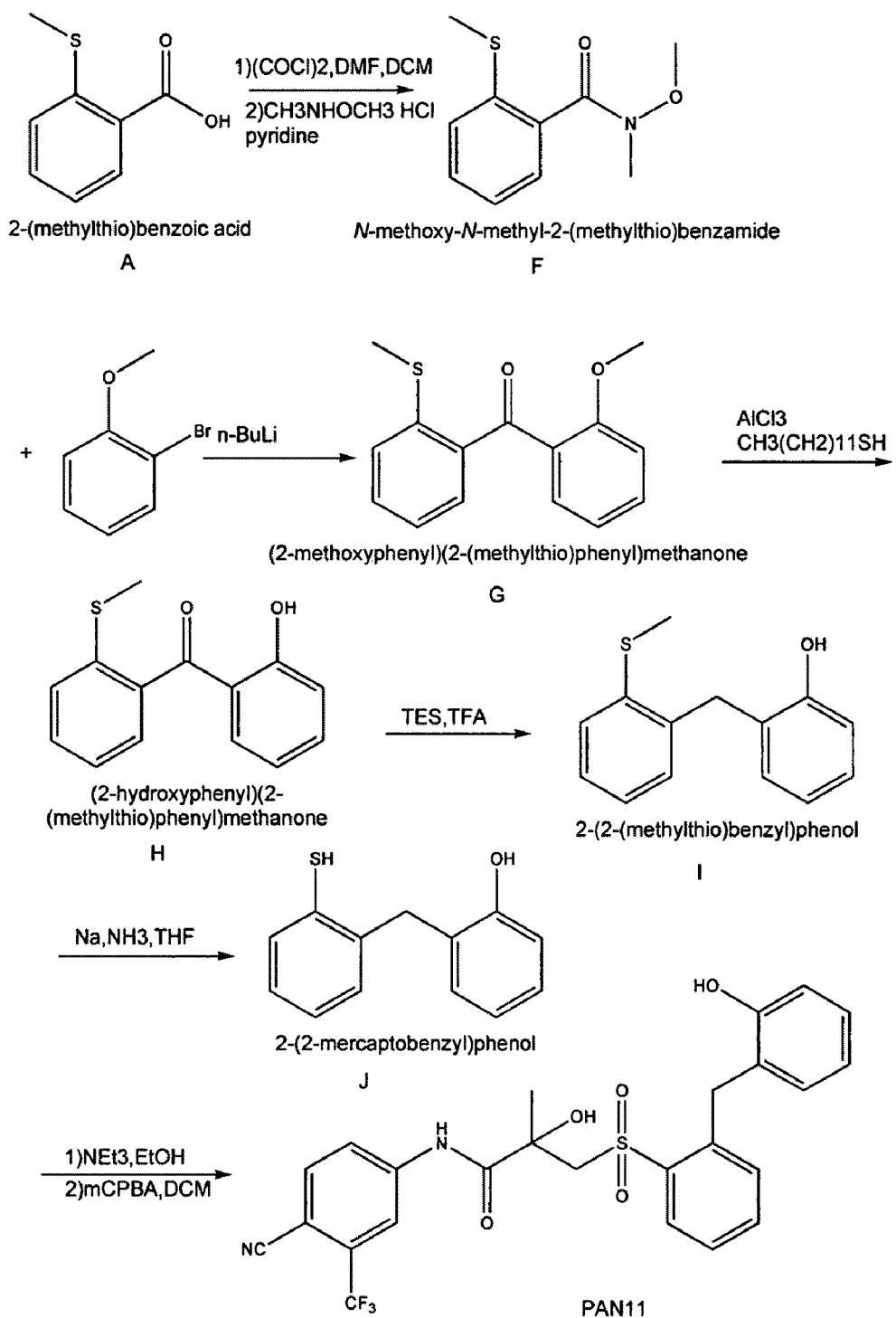
Figure 43:
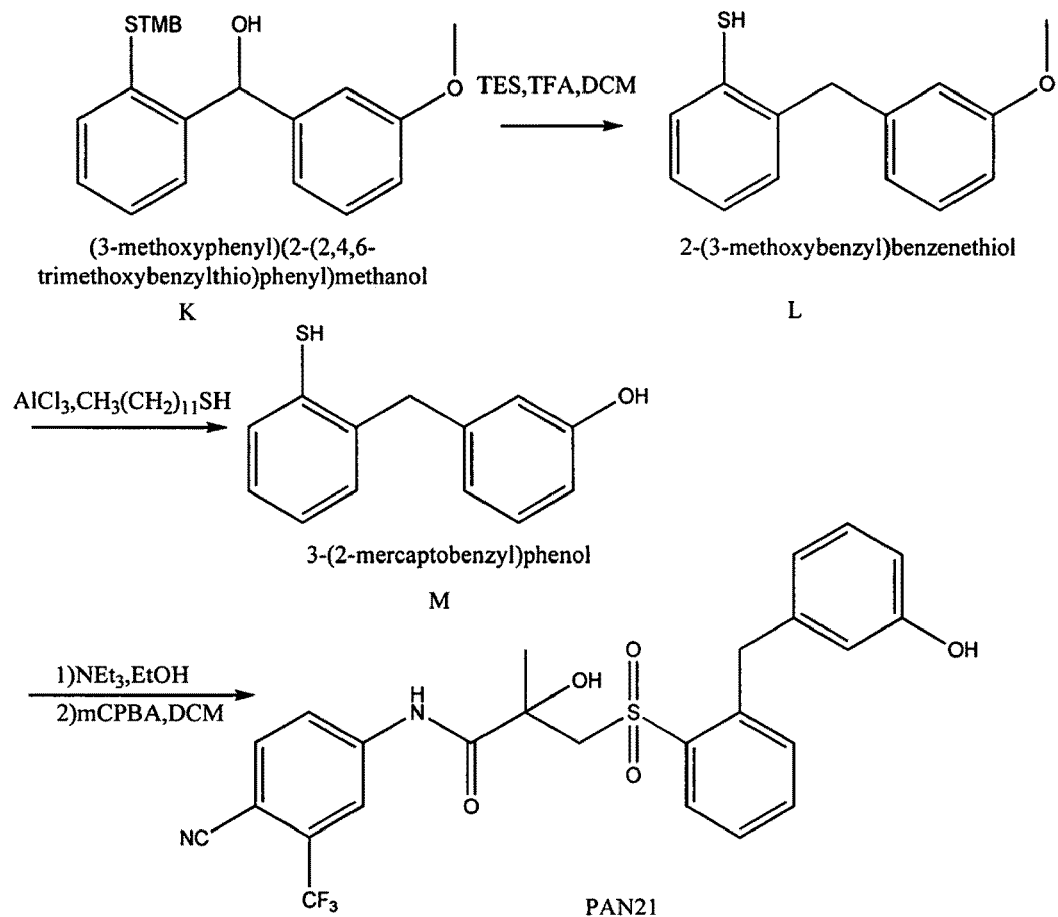
Figure 44:
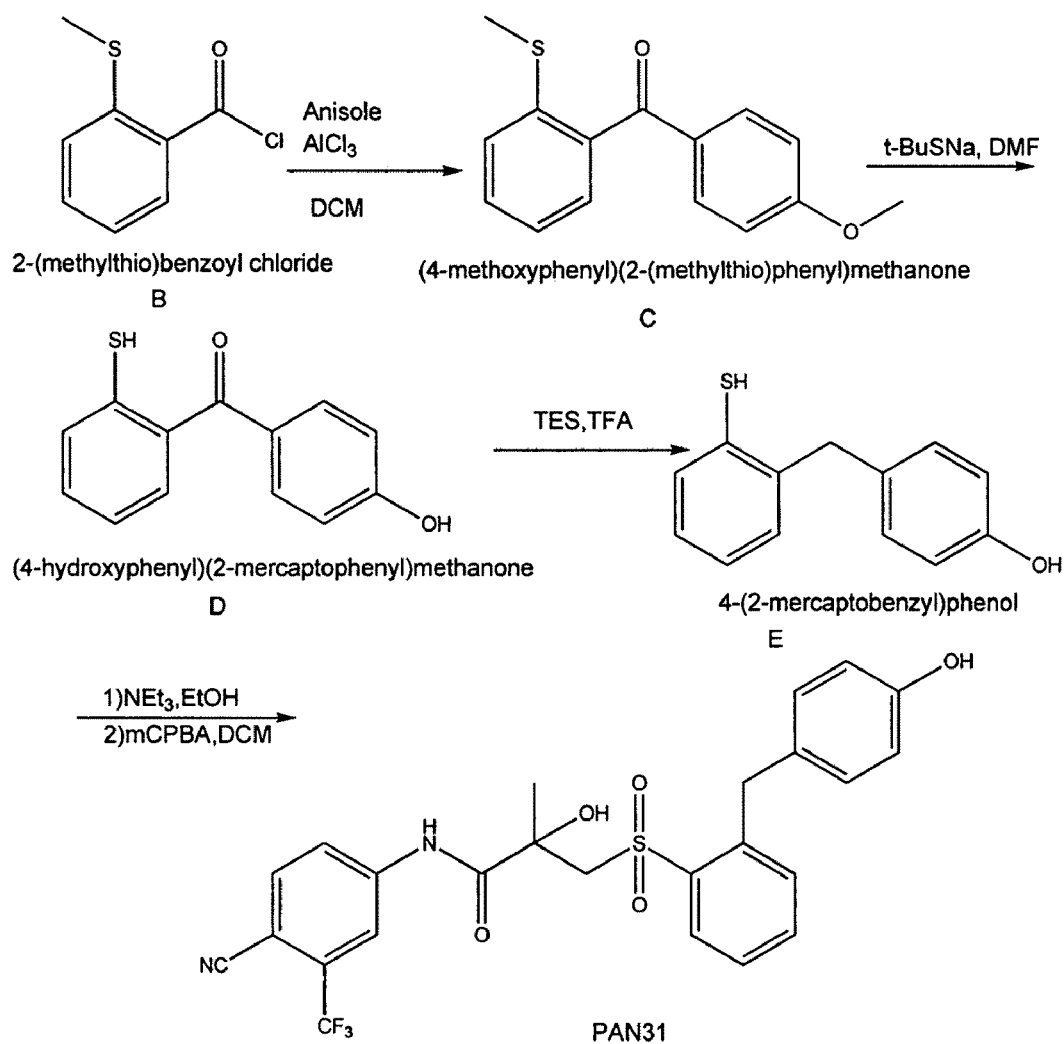
Figure 45:
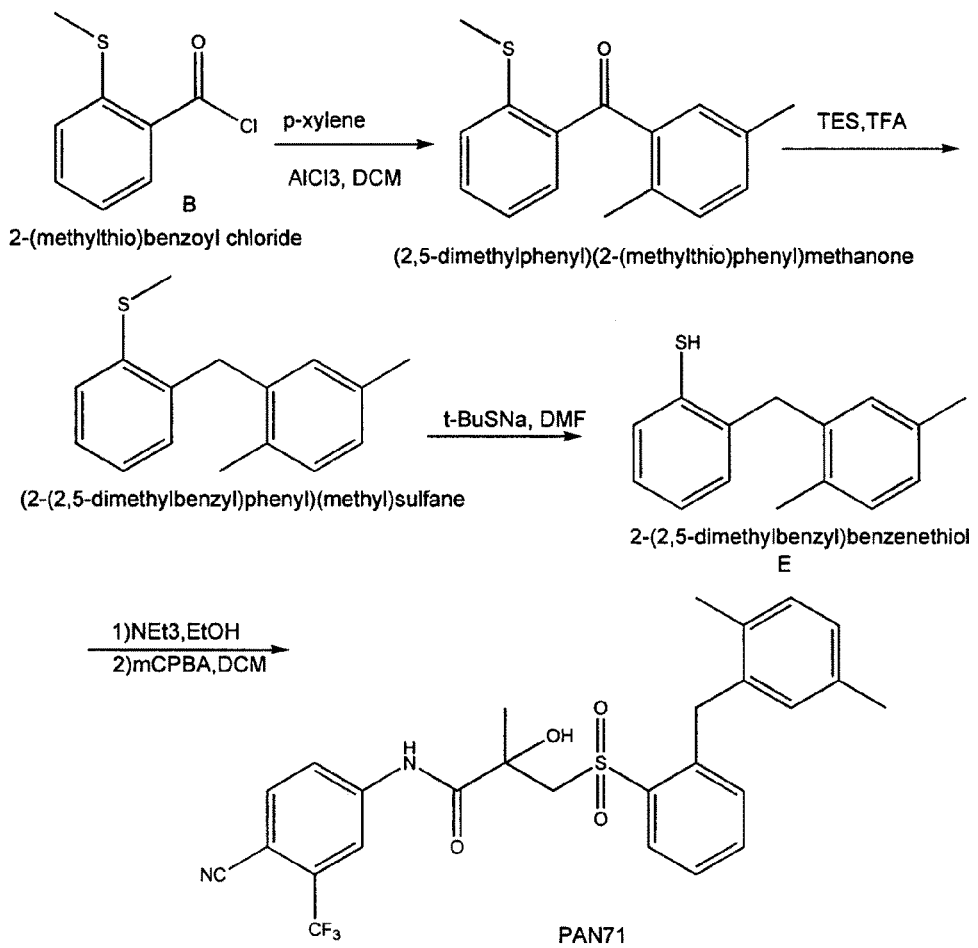
Figure 46:
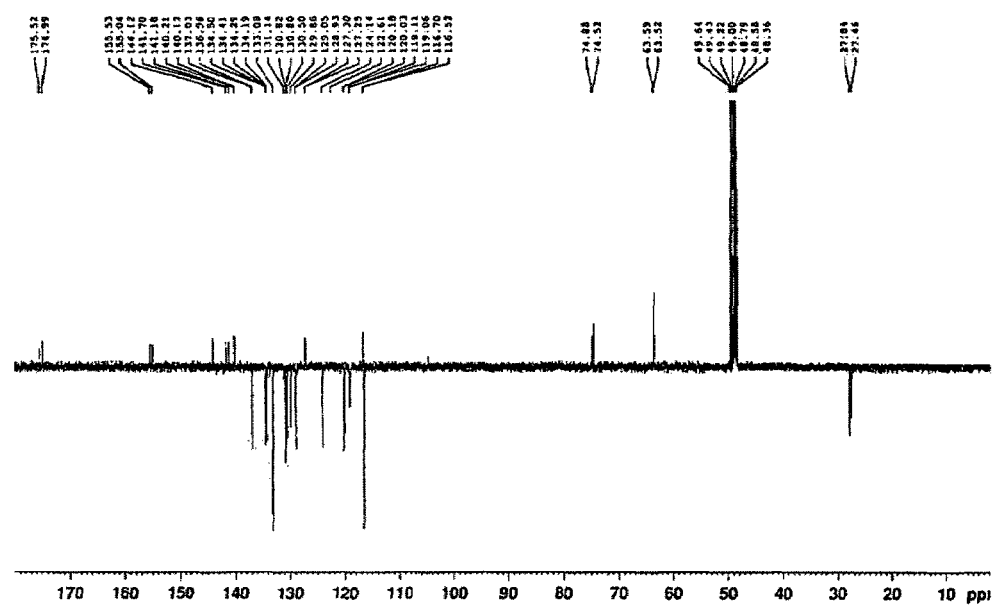
Figure 47:
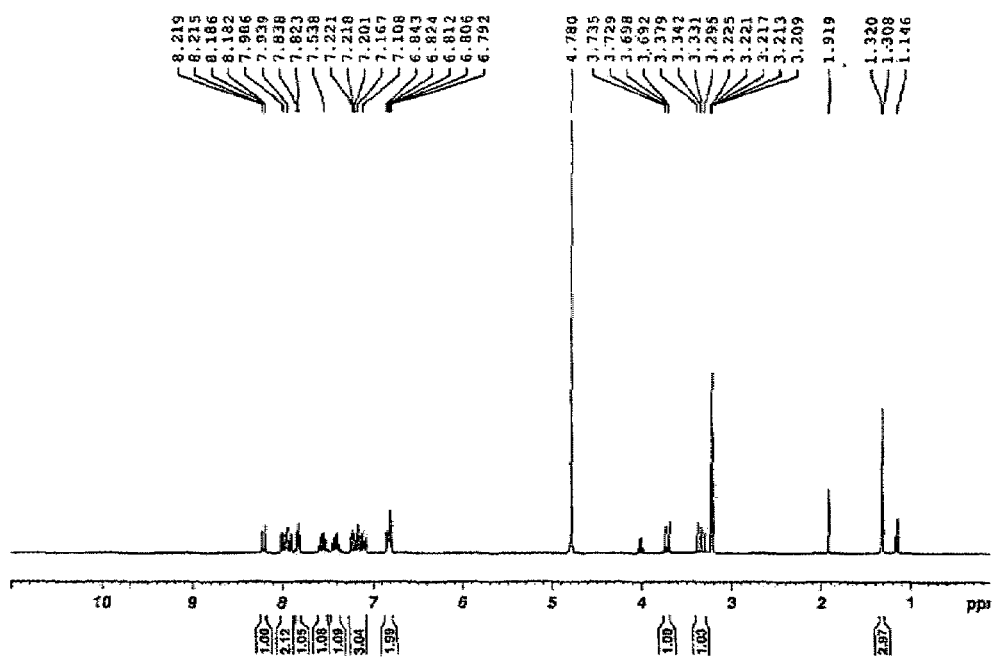
Figure 48:
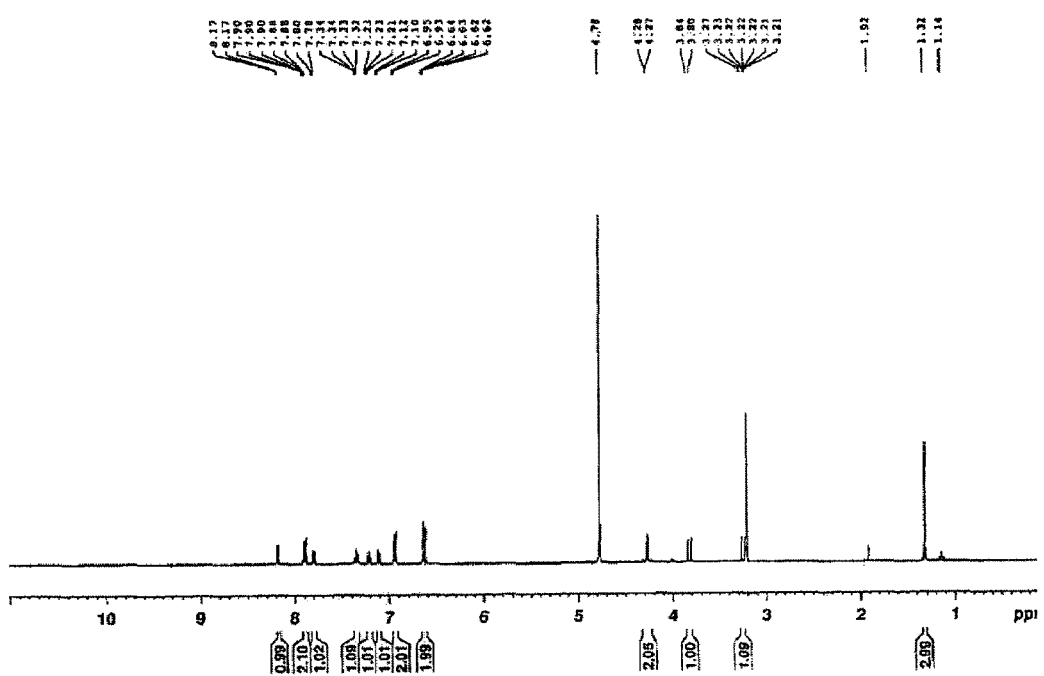
Figure 49:
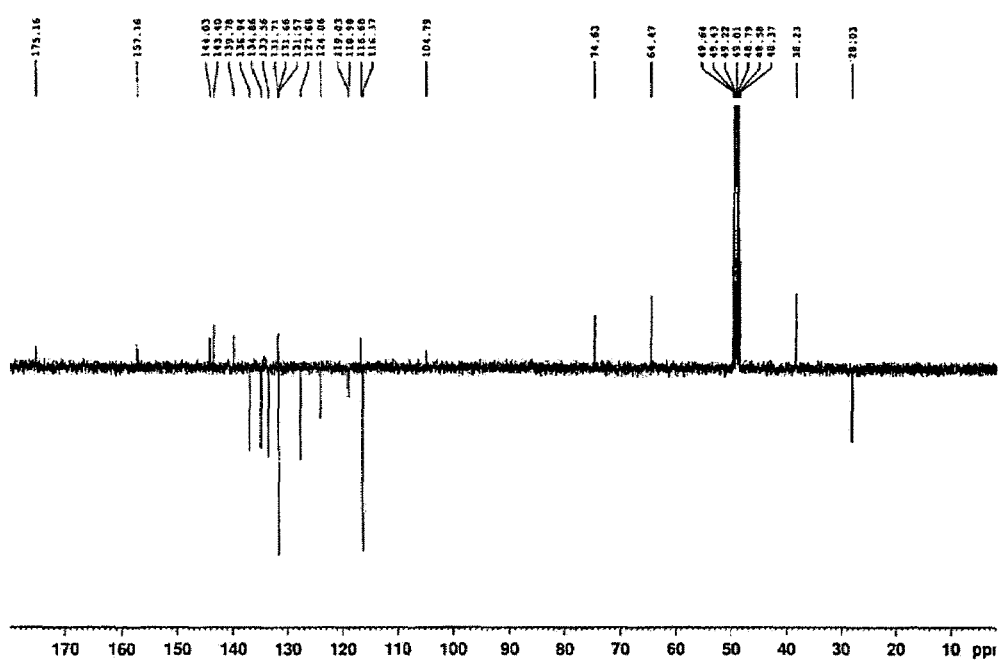
Figure 50:
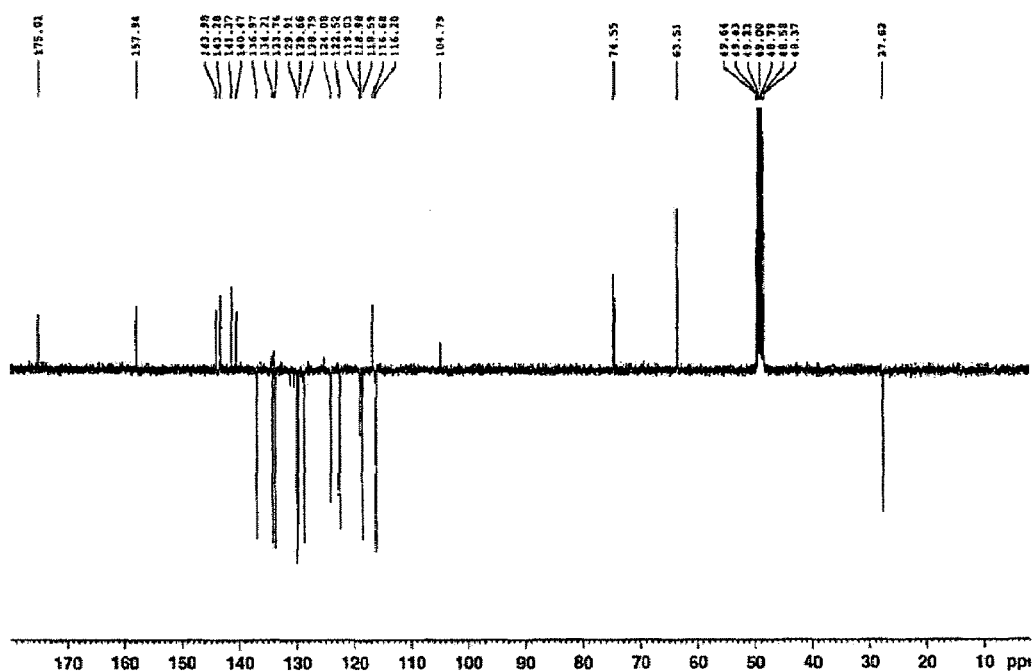
Figure 51:
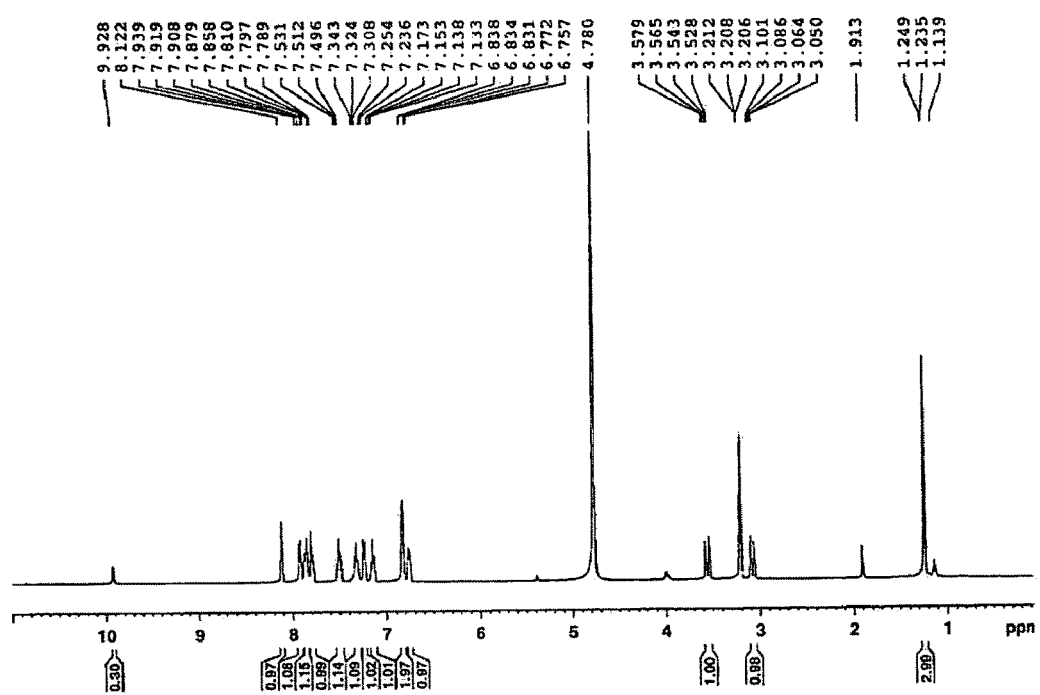
Figure 52:
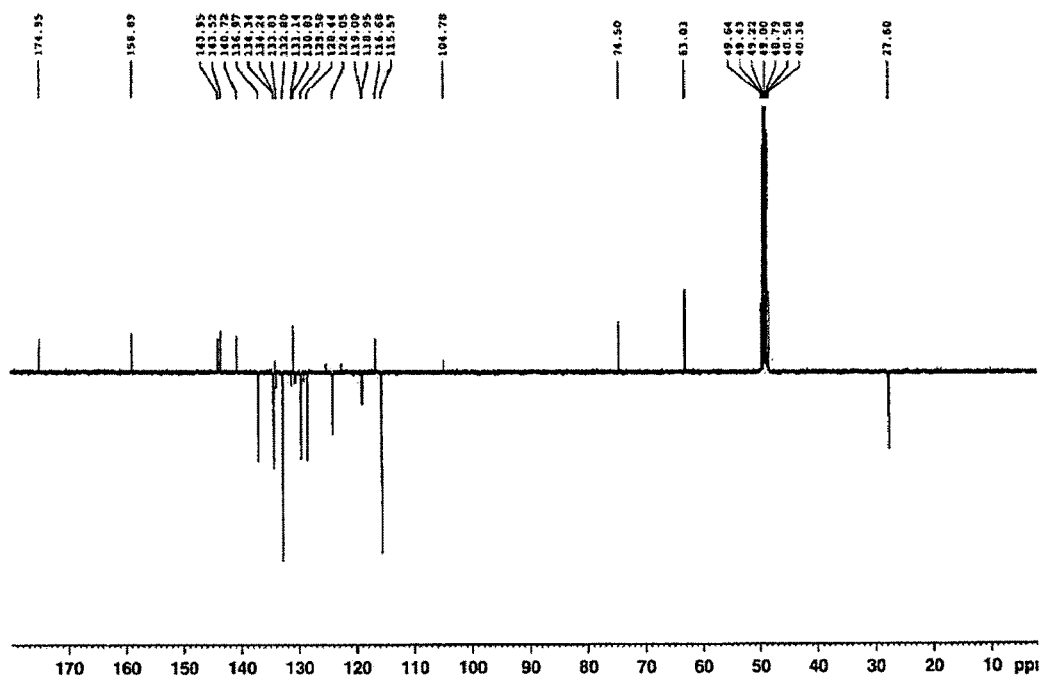
Figure 53:
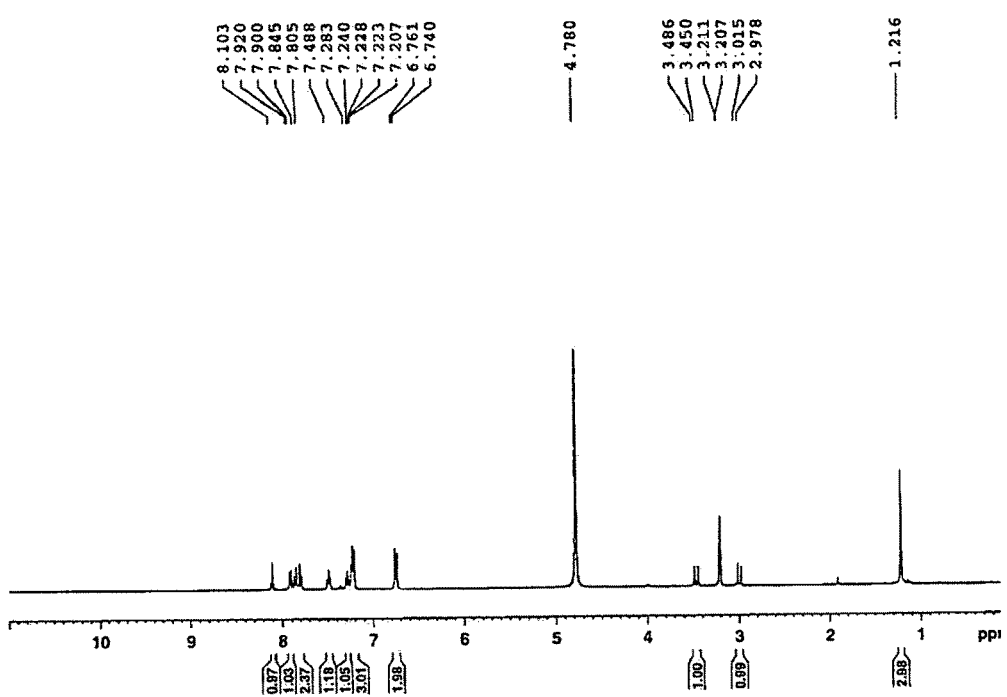
Figure 54:
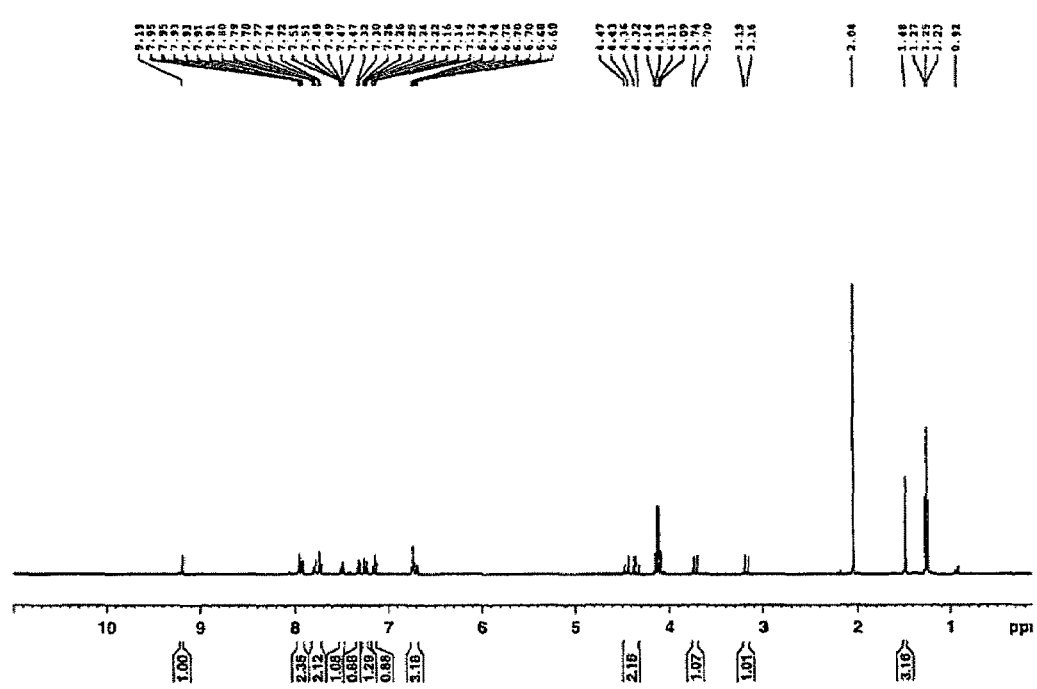
Figure 55:
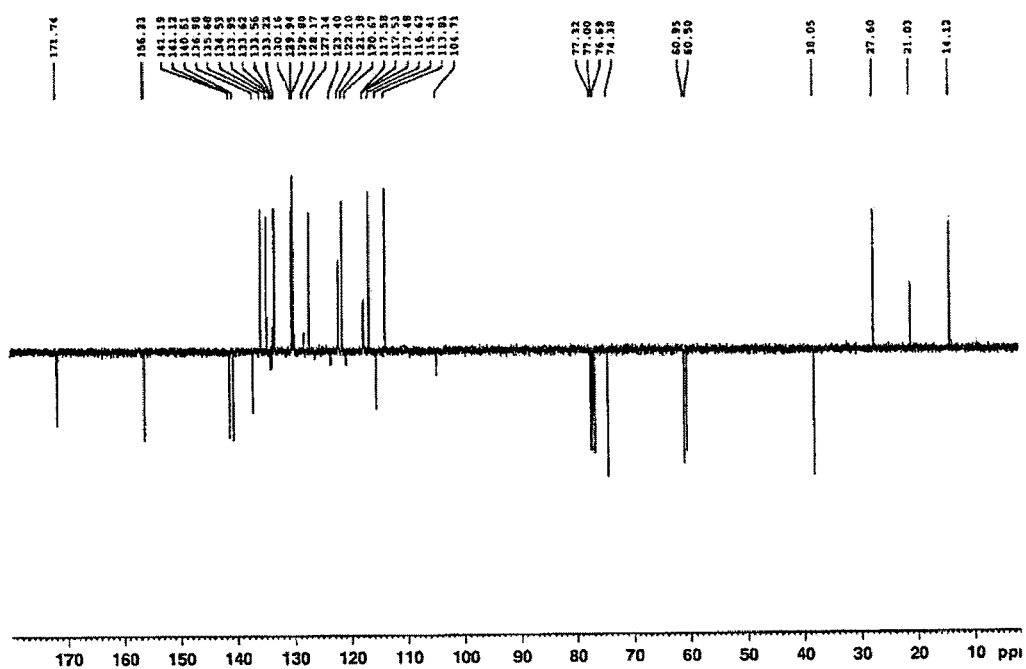
Figure 56:
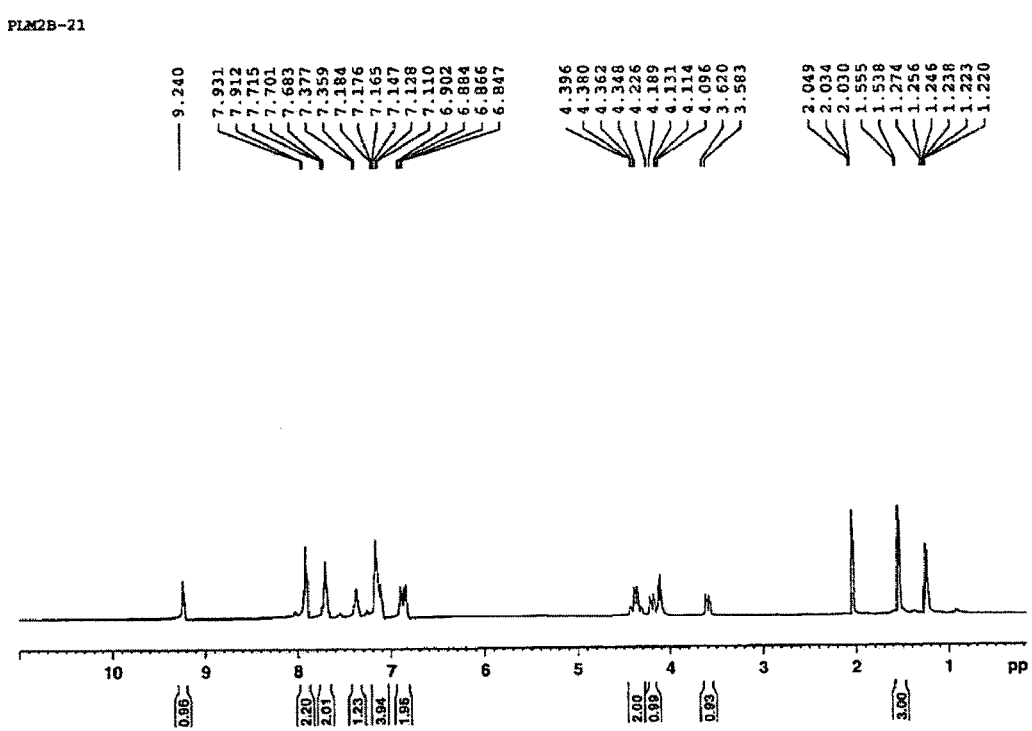
Figure 57:
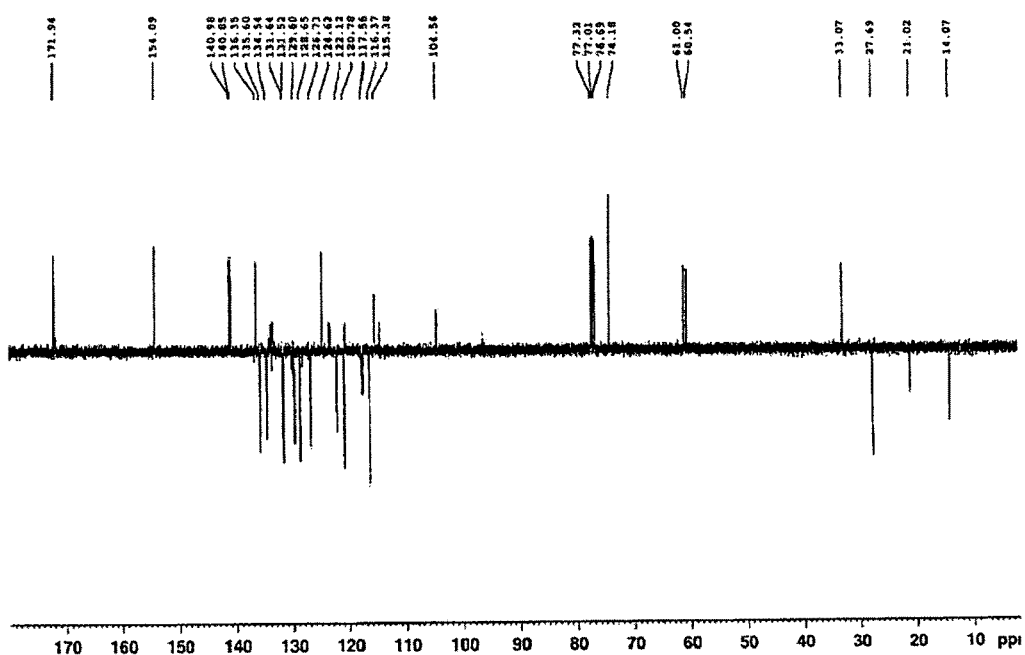
Figure 58:
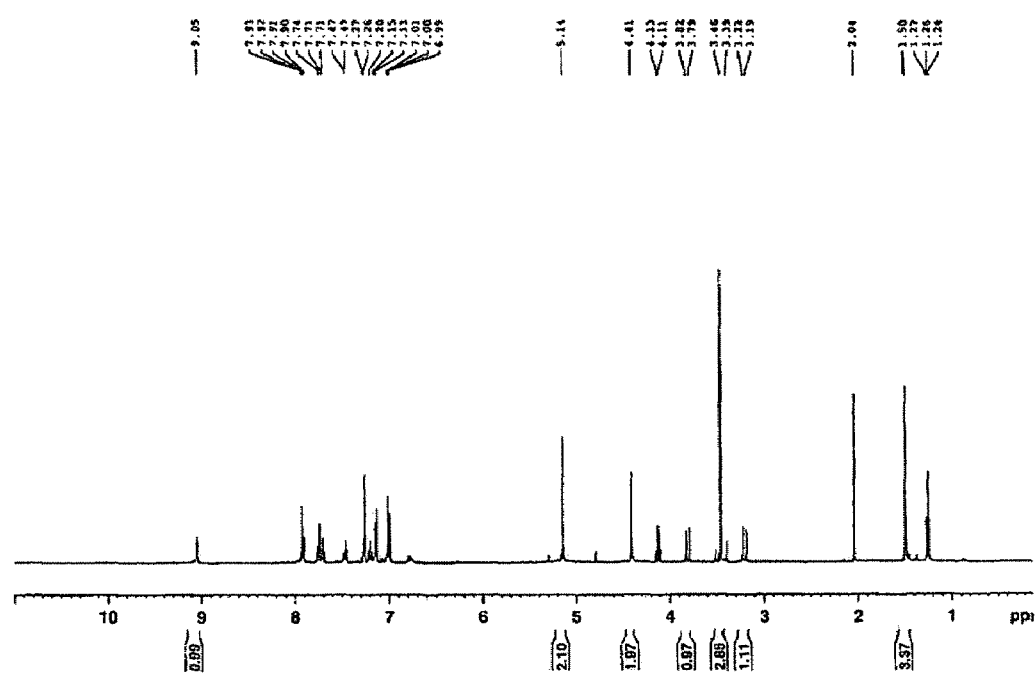
Figure 59:
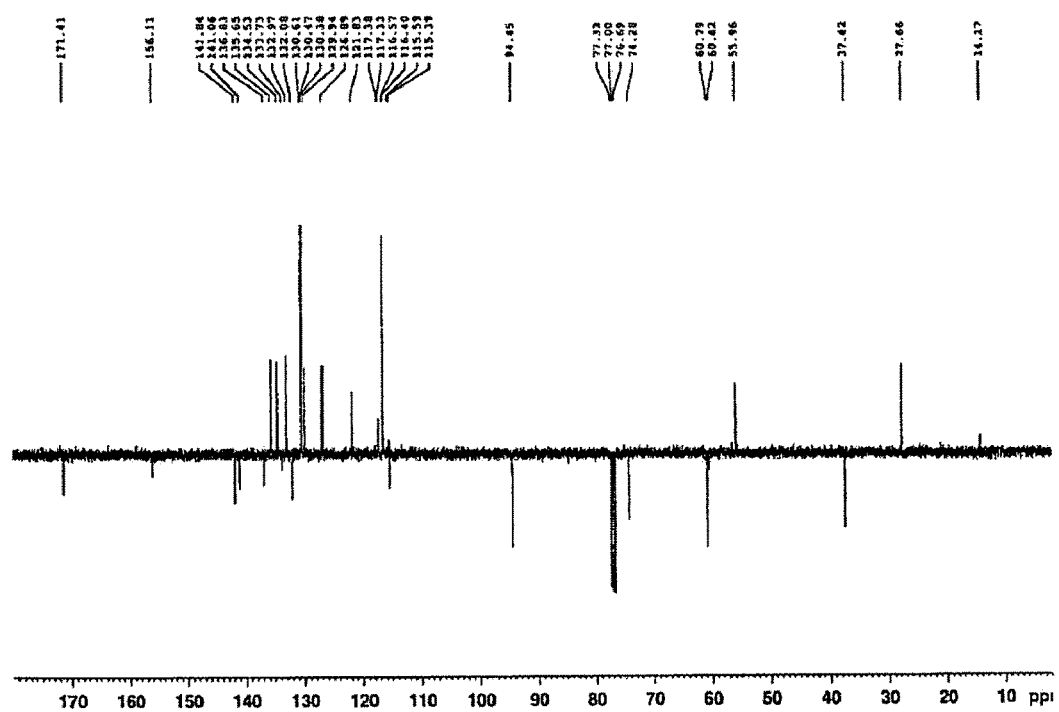
Figure 60:
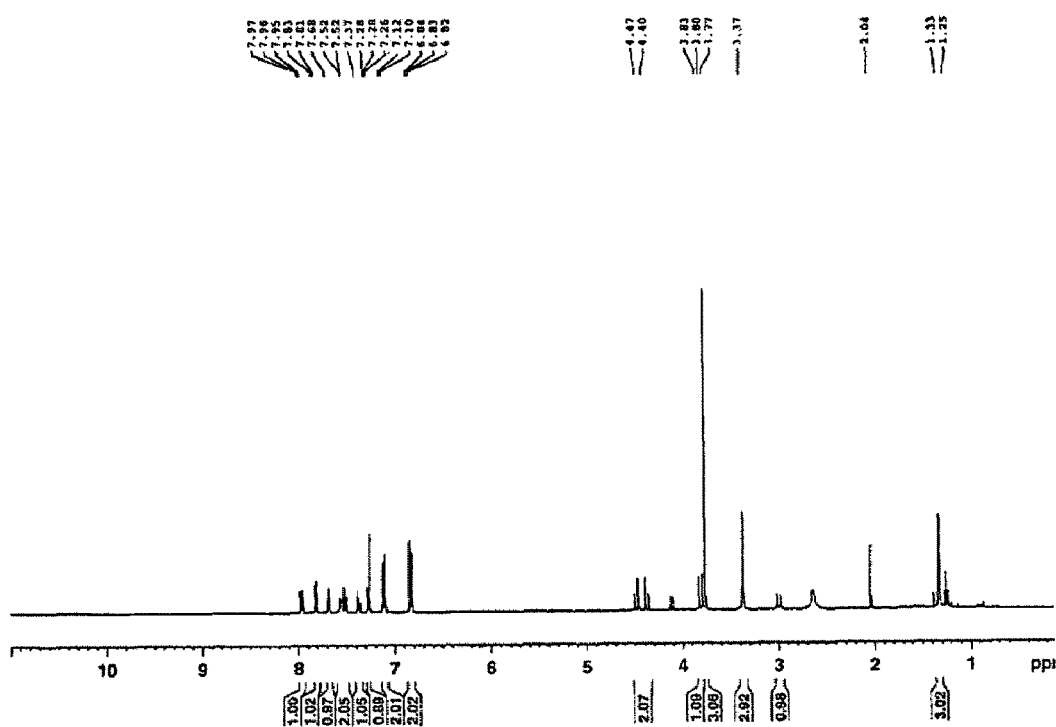
Figure 61:
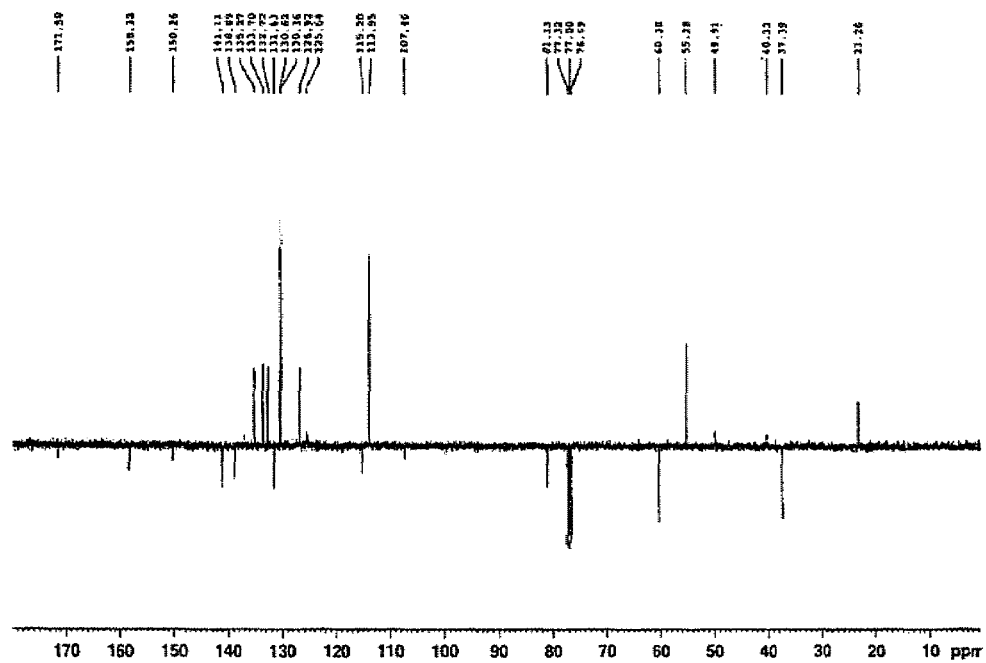
Figure 62:
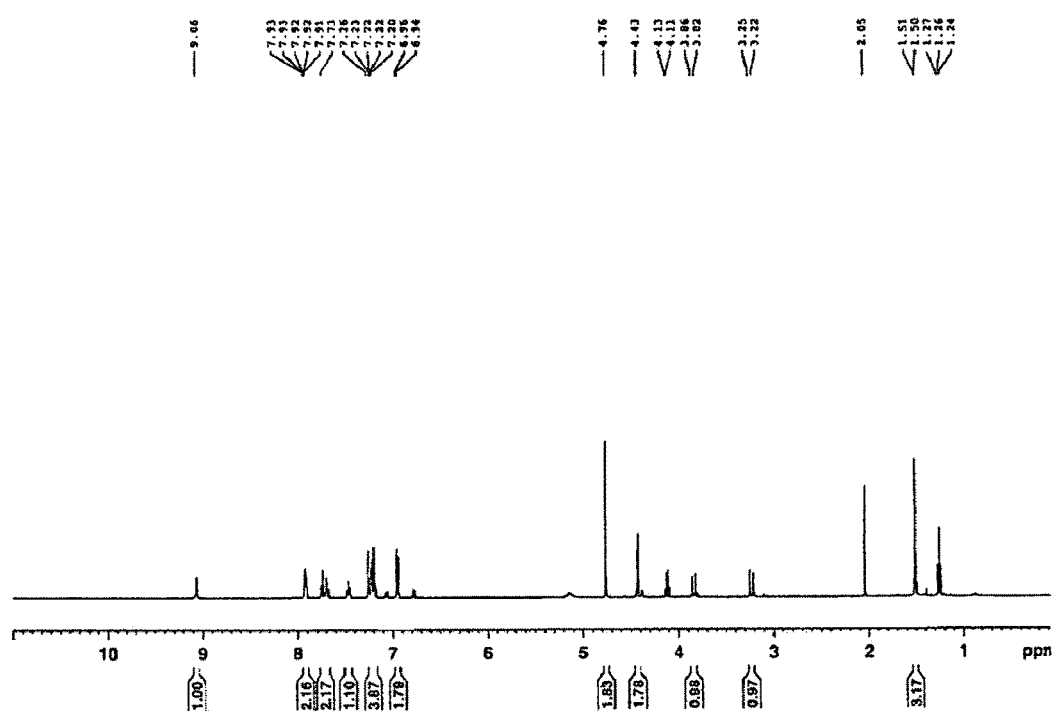
Figure 63:
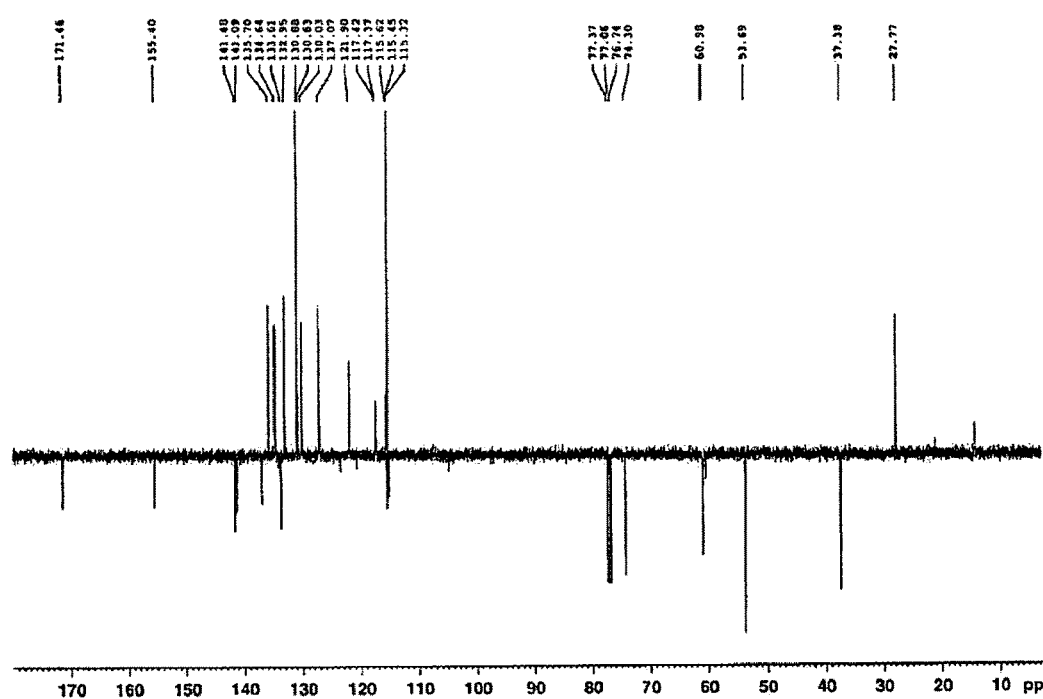
Figure 64:
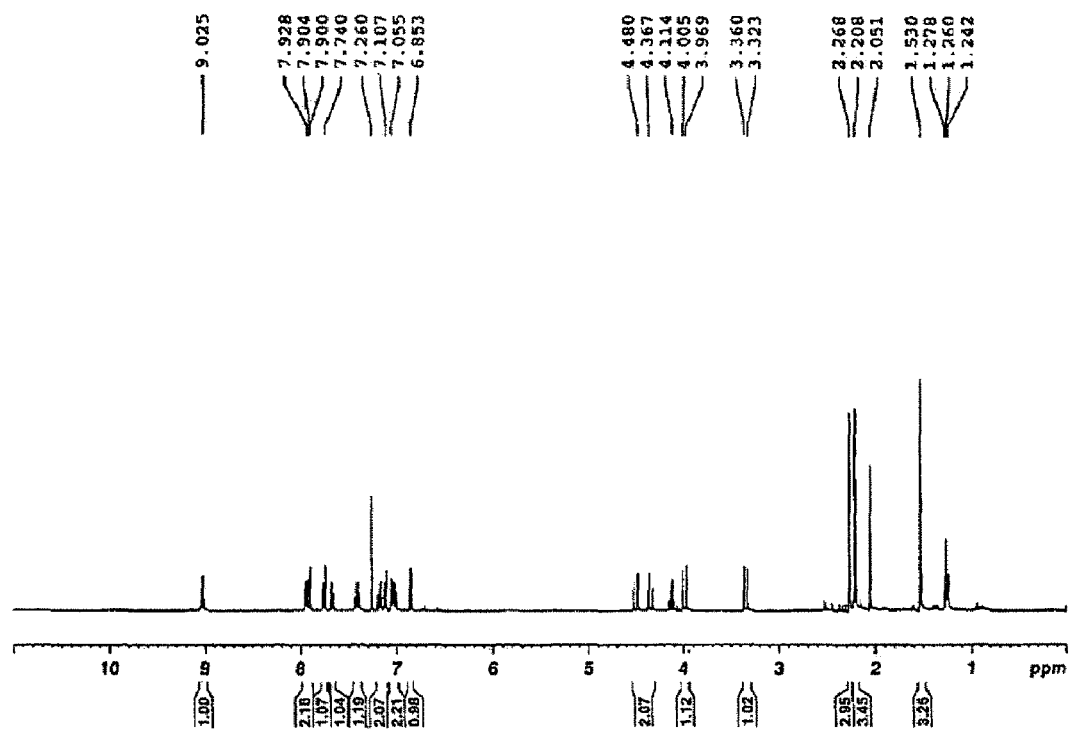
Figure 65:
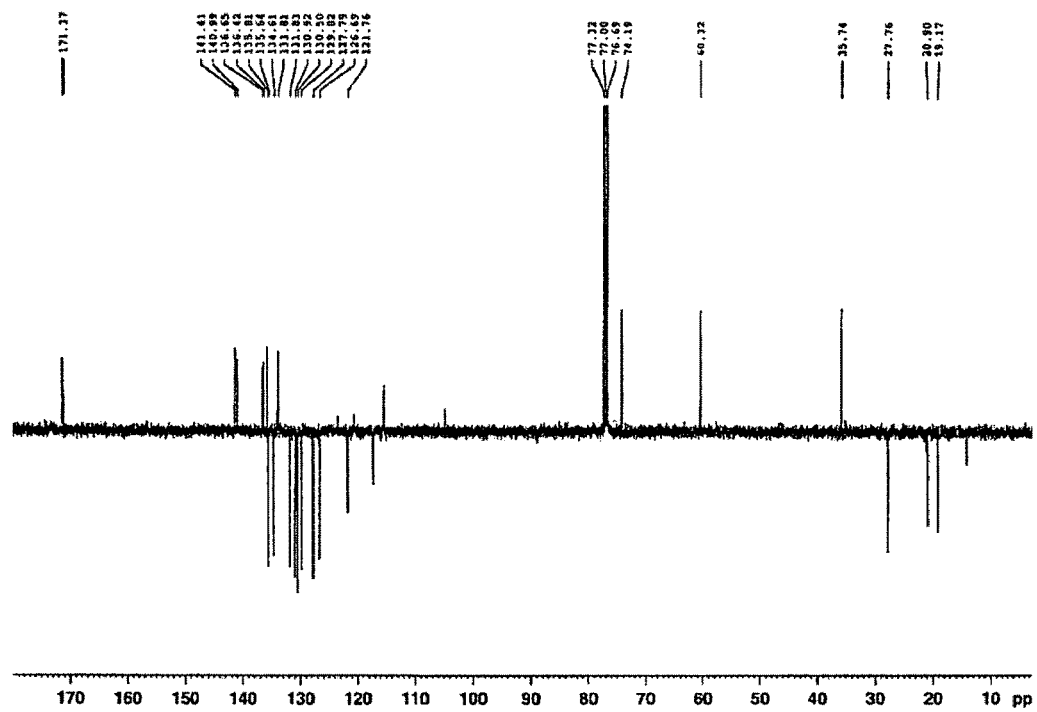

The mixture of 0.51 g 2-(2,5-dimethylbenzyl)benzenethiol (2.24 mmol), 0.609 g N-(4-Cyano-3-(trifluoromethyl)phenyl)-2-methyloxirane-2-Carboxamide (2.24 mmol), 0.5 ml triethylamine, 6 ml ethanol was stirred overnight and concentrated. The residue was dissolved in ethyl acetate, washed with water, brine, dried over magnesium sulfate and concentrated. Without further purification, the residue was mixed with 3.85 g mCPBA (15.5 mmol), 30 ml DCM. The mixture was stirred overnight and concentrated. The residue was dissolved in ethyl acetate, washed with water, brine, dried over magnesium sulfate and concentrated. Purification by chromatography (hexane:ethyl acetate 50:50) yield 0.228 g product (0.43 mmol, 19% yield for two steps). Production of PAN71 was confirmed by 1-H NMR and 13-C NMR. See FIG. 16 for the general PAN71 synthesis strategy.

Example 57

Transcription Assays

Twenty-four hours prior to transfection, CV-1 cells were seeded at a density of 45,000 cells per well in 24-well cell culture plates and grown in phenol red free Dulbecco's Modified Eagle Medium (DMEM) supplemented with 10% cosmic calf serum (CCS). ARE-luciferase reporter and Renilla-Luc as the internal standard and a prokaryotic expression vector encoding the wild-type androgen receptor or mutant androgen receptor were transfected with Lipofectamine (Invitrogen) following manufacturer's protocol. Five hours after transfection, media was added containing the appropriate concentrations of ligands. The cells were allowed to incubate for 38 hours before harvesting by passive lysis buffer. Cell extracts were immediately assayed using the Dual Luciferase Assay (Promega). See FIGS. 1-8 and Table 1 for results.

Example 58

Competitive Binding Assays

Twenty-four hours prior to transfection, COS-7 cells were seeded at a density of 70,000 cells per well in 24-well cell culture plates and grown in phenol red free Dulbecco's Modified Eagle Medium (DMEM) supplement with 10% cosmic calf serum (CCS). The cells were transfected with a prokaryotic expression vector encoding the wild-type androgen receptor or mutant androgen receptor using Lipofectamine (Invitrogen) following manufacturer's protocol. The cells were allowed to grow for 30 hours and then labeled for 2 hours at 37° C. with [$^3$H]DHT and the appropriate concentration of ligands. Cells were washed with PBS and harvested in 2% SDS, 10% glycerol, and 10 mM Tris, pH 6.8, and radioactivity determined by scintillation counting. See Table 1 for results.

TABLE 1

Cellular transcription response (EC50/IC50) and Competitive Binding assays for DHT bicalutamide and analogs as agonists and antagonists of AR(wild-type), AR(W741L), AR(W741L) and AR(T877A).

| | hAR(wt) | | | hAR(W741L) | | | hAR(W741C) | | | hAR(T877A) | |
|---|---|---|---|---|---|---|---|---|---|---|---|
| | IC50 mM | EC50 nM | $K_i$ mM | IC50 mM | EC50 nM | $K_i$ mM | IC50 mM | EC50 nM | $K_i$ mM | IC50 mM | EC50 nM |
| Bic | 1 ± 0.08 | — | 0.4 | — | 52 ± 14.6 82% | 0.2 ± 0 | — | 107 ± 23 74% | 0.7 ± 0.5 | 1.9 ± 0.4 | — |
| PLM1 | 3.8 ± 0.7 | — | 0.5 | 9.7 ± 1.9 | — | 2.1 ± 2.2 | 3.3 ± 1.1 | — | 5.9 ± 6.2 | 6 ± 0.4 | — |
| PLM2 | 12.5 ± 2.2 | — | 6.3 | 23 ± 6.2 | — | 2.9 ± 1.1 | 11.6 ± 1.2 | — | 2.8 ± 1.6 | 16.5 ± 4.6 | — |
| PLM3 | 12.9 ± 3.6 | — | 1.6 | — | — | — | — | 630 ± 67 65% | nd | — | — |
| PLM4 | 7.4 ± 2.5 | — | 2.7 | — | — | — | — | 33 ± 9.8 66% | 2.7 ± 2.9 | — | — |
| PLM6 (PLM54) | 21.4 ± 9.9 | — | 2.1 | 7.9 ± 1.9 | — | 1 ± 0.4 | 7.4 ± 0.9 | — | 0.2 ± 0.03 | 5.4 ± 1.7 | — |
| PLM7 (PLM55) | — | — | — | — | — | — | — | — | — | — | — |
| PLM8 | 4.4 ± 0.7 | — | 1.1 ± 0.6 | — | — | — | — | — | — | 7.7 ± 1.2 | — |
| PLM10 | — | — | — | — | — | — | — | — | — | — | — |
| PLM11 | — | — | — | — | — | — | — | — | — | — | — |
| PLM12 | — | — | — | — | — | — | — | — | — | — | — |
| PLM9 | 7.2 ± 2.3 | — | 1.8 ± 1.1 | 9.5 ± 4.7 | nd | — | — | — | — | 7.6 ± 3.4 | 426 ± 72 48.00% |
| PLM13 | 40.8 ± 15.7 | — | nd | — | — | — | — | — | — | — | — |
| PLM14 | 12 ± 2.4 | — | 3.1 ± 0.4 | — | — | — | — | — | — | 5.5 ± 1.3 | nd |
| PLM15 | 4.4 ± 1.0 | — | 0.7 ± 0.3 | 17 ± 4.5 | nd | — | — | — | — | 4.9 ± 0.9 | nd |
| PLM16 | 8 ± 2.7 | — | 15.8 ± 11 | — | — | — | — | — | — | 15.4 ± 1.8 | nd |
| PLM18 | 8.6 ± 2.4 | — | 4.4 ± 0.8 | — | — | — | — | — | — | — | nd |
| PLM19 | — | — | — | — | — | — | — | — | — | 9 ± 1.6 | nd |
| PAN71 | 3 | — | nd | nd | nd | nd | nd | nd | nd | nd | nd |
| PAN11 | 2.5 | — | nd | nd | nd | nd | 0.18 | 0 | nd | — | 1.9 |
| PAN21 | 1.7 | 1.8 | nd | nd | nd | nd | 2.3 | — | nd | 2.5 | — |
| PAN31 | 8.8 | — | nd | nd | nd | nd | 14 | — | nd | 20 | — |
| PAN32 | 0.6 | — | nd | nd | nd | nd | nd | nd | nd | nd | nd |
| PAN33 | 3.7 | — | nd | nd | nd | nd | nd | nd | nd | nd | nd |
| PAN37 | 11 | — | nd | nd | nd | nd | nd | nd | nd | nd | nd |
| PAN41 | 1.7 | — | nd | nd | nd | nd | nd | nd | nd | nd | nd |
| PAN51 | 10 | — | nd | nd | nd | nd | nd | nd | nd | nd | nd |
| PAN61 | 12 | — | nd | nd | nd | nd | nd | nd | nd | nd | nd |

'bic' = bicalutamide.
$EC_{50}$ = effective concentration for half maximal activation of reporter gene expression.
$IC_{50}$ = 50% inhibitory concentration of cellular reporter gene expression induced by 3 nM, 250 nM, 200 nM or 10 nM DHT for wild-type, W741L, W741C and T877A respectively. Competitive binding assays (Ki) were measured in the presence of 8 nM, 100 nM and 75 nM [$^3$H]-DHT for AR(wild-type), AR(W741L) and AR(W741C) respectively.
'nd' indicates values were not determined, and
'—' indicates no effect.

Example 59

Cell Proliferation Assays

Figure 9:
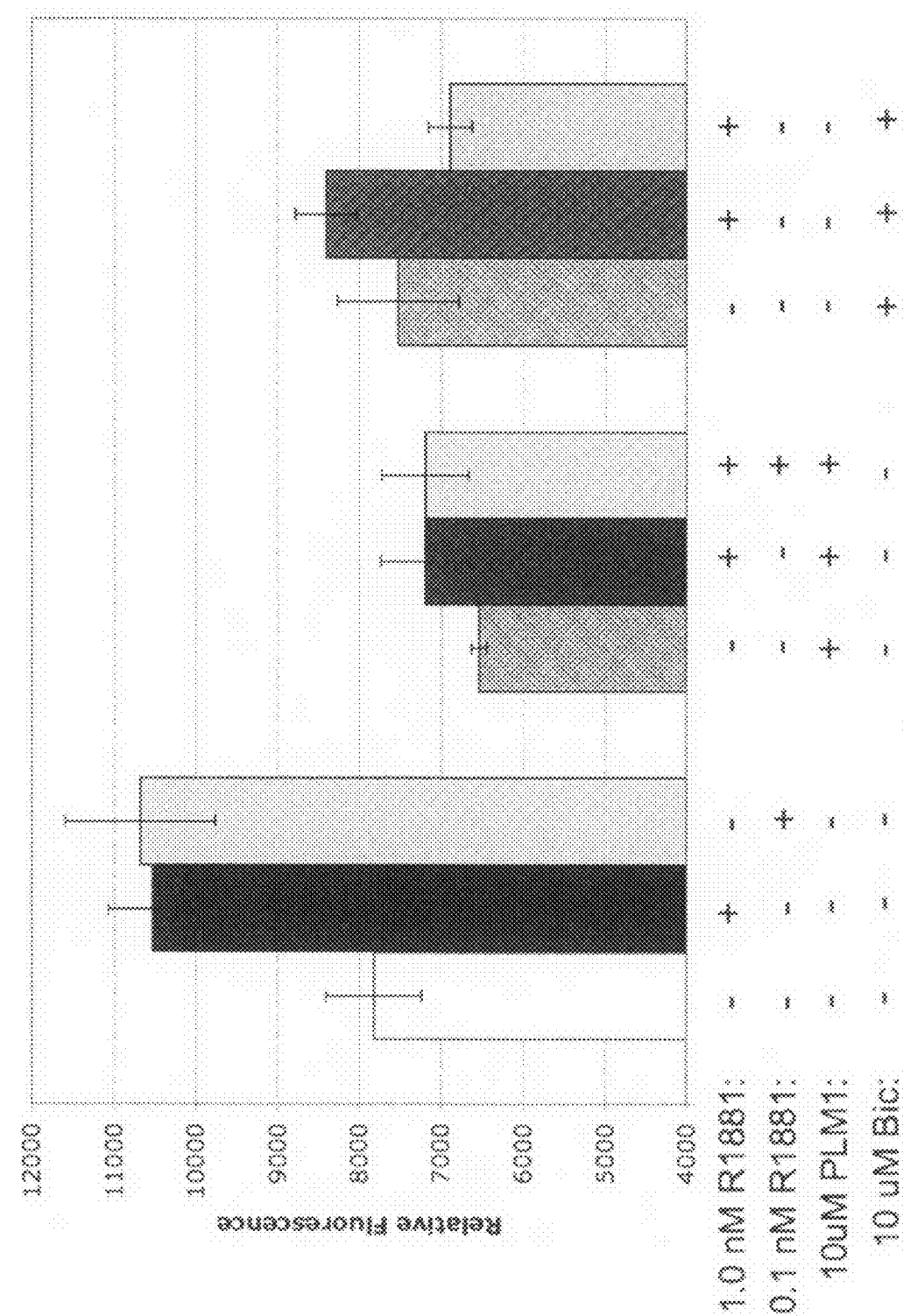
FIG. 9. LNCaP cell proliferation (CyQuant) after 8 day ligand treatment±R1881. Relative Fluorescence ±SEM. (R1881±ligand; $P<0.05$, one-way ANOVA).

Further evidence that formulae such as PLM1 can act to limit androgen dependent proliferation of prostate cells was obtained by cell proliferation assays as determined using CyQuant® assays, according to manufacturer's instructions (Invitrogen). Compounds such as PLM1 were found to be at least as potent as biclutamide itself at inhibiting androgen (R1881) induced proliferation of LNCaP cells (see FIG. 9).

Example 60

In Vitro Selections

Figure 10:
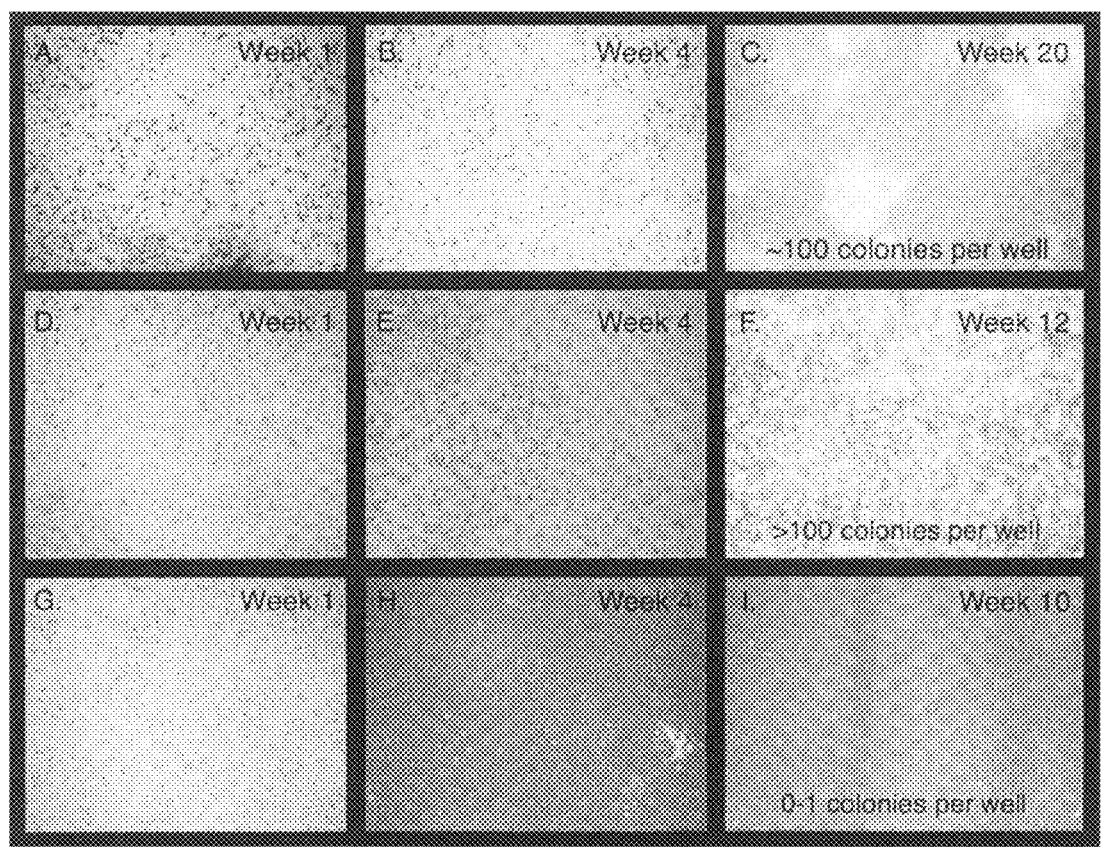
FIG. 10. In vitro selections of LnCaP cells with 20 μM bicalutamide: A. week 1, B. Week 4, C. Week 20; 20 μM Formula III: D. week 1, E. week 4, F. week 12; 20 μM Formula VII: G. week 1, H. Week 4, I. Week 10 (note: no colonies detected in two of three experiments).

Additional evidence that the formulae possess potential to evade anti-androgen withdraw phenotype is demonstrated by in vitro selection assays in LnCAP cells following the method of Hara et al. as described in *Cancer Research*, 63, 149-153 (2003). LnCAP cells grown in the presence of 20 μM bicalutamide result he selection of antagonist resistant colonies in 20 weeks. Parallel studies starting from 40,000 cells per 3.2 cm dishes show that compounds such as Formula VII, reduce the formation of resistant colonies (see FIG. 10).

We claim:
1. A compound of the formula:

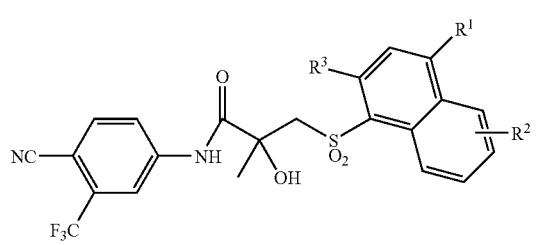

(I)

wherein $R^1$ is hydrogen, fluorine, chlorine, bromine, cyano, hydroxy, methyl acrylate, or $C_1$-$C_6$ alkyl optionally substituted with hydroxy;

$R^2$ is hydrogen, hydroxy, fluoro, chloro, cyano, $C_1$-$C_5$ alkanoate, $C_1$-$C_5$ alkylamino, or $C_1$-$C_6$ alkyl optionally substituted with hydroxy or acrylate; and $R^3$ is hydrogen, $C_1$-$C_6$ alkyl, fluoro, chloro, bromo, or cyano.

2. The compound of claim 1, selected from the group consisting of:

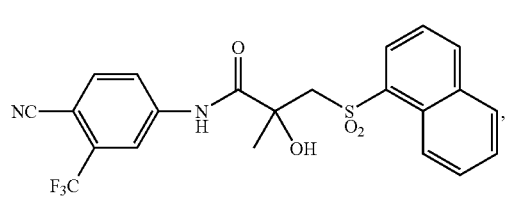
(III)

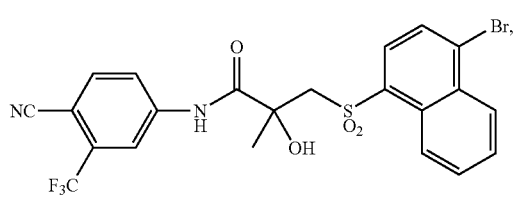
(IV)

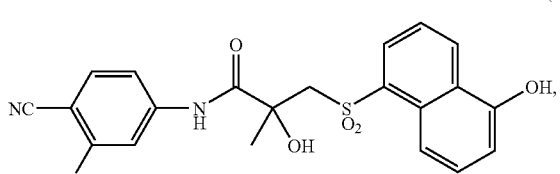
(V)

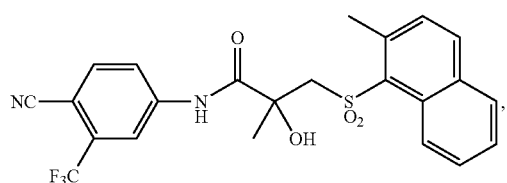
(VI)

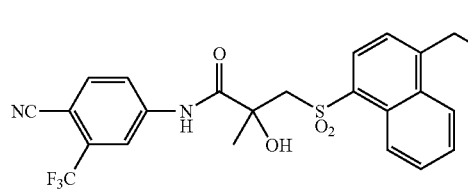
(XII)

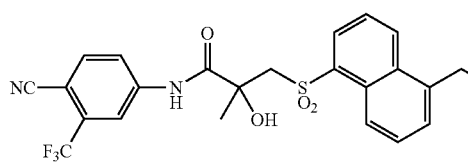
(XIII)

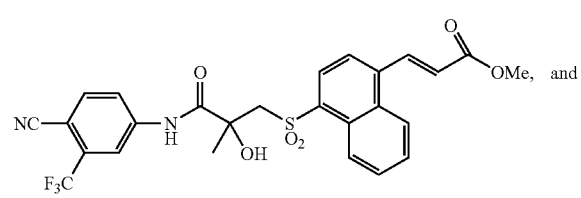
(XIV)

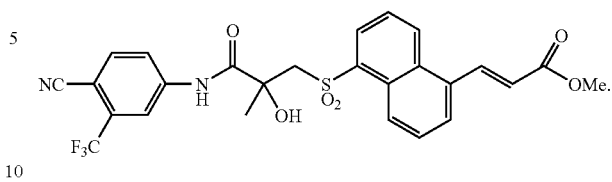
(XV)

3. A compound of the formula:

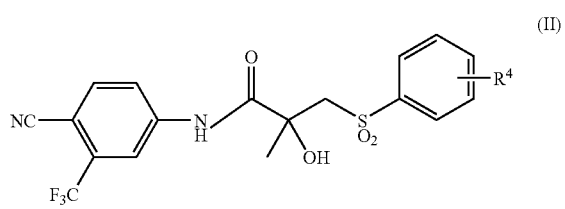
(II)

wherein $R^4$ is phenyl optionally substituted with hydroxy; $C_1$-$C_6$ phenylalkyl; or benzyl optionally substituted with hydroxy, $C_1$-$C_6$ alkoxy optionally substituted with methoxy or cyano, $C_1$-$C_6$ alkyl, $C_1$-$C_5$ alkanoate, or $C_1$-$C_5$ alkylamine.

4. The compound of claim 3, selected from the group consisting of:

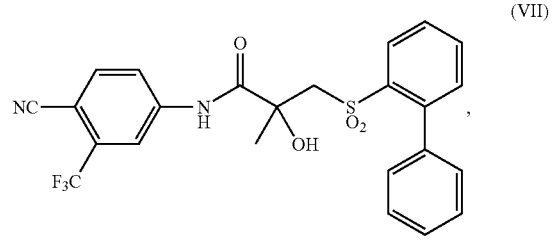
(VII)

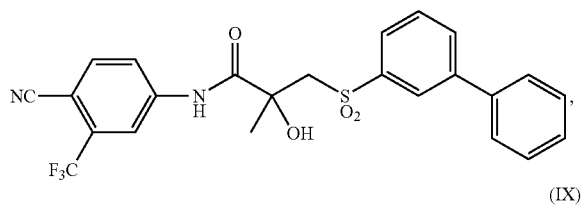
(VIII)

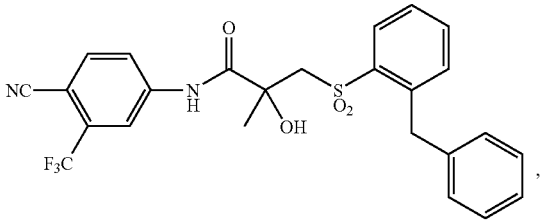
(IX)

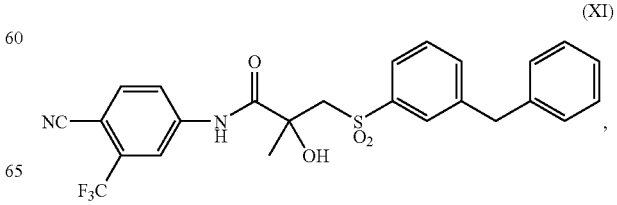
(XI)

-continued
(XVI), (XVII), (XVIII), (XIX), (XX), (XXI), (XXII), (XXIII), (XXIV), (XXV)
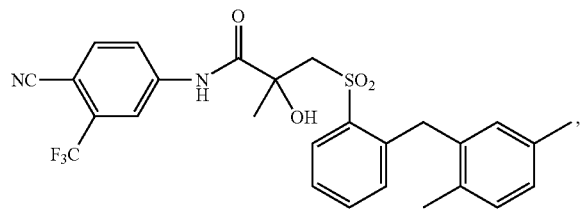
5. A pharmaceutical composition comprising a compound of claim 1 or 3.
6. A pharmaceutical composition comprising a compound of claim 2 or 4.
* * * * *